US011730346B2

(12) United States Patent
Sholev

(10) Patent No.: US 11,730,346 B2
(45) Date of Patent: *Aug. 22, 2023

(54) TWO-PART ENDOSCOPE SURGICAL DEVICE

(71) Applicant: GREAT BELIEF INTERNATIONAL LIMITED, Tortola (VG)

(72) Inventor: Mordehai Sholev, Moshav Amikam (IL)

(73) Assignee: GREAT BELIEF INTERNATIONAL LIMITED, Tortola (VG)

( * ) Notice: Subject to any disclaimer, the term of this patent is extended or adjusted under 35 U.S.C. 154(b) by 777 days.

This patent is subject to a terminal disclaimer.

(21) Appl. No.: 16/663,129

(22) Filed: Oct. 24, 2019

(65) Prior Publication Data

US 2020/0129051 A1 Apr. 30, 2020

Related U.S. Application Data

(60) Continuation of application No. 16/590,268, filed on Oct. 1, 2019, which is a continuation of application
(Continued)

(51) Int. Cl.
*A61B 1/00* (2006.01)
*A61B 1/313* (2006.01)
(Continued)

(52) U.S. Cl.
CPC .......... *A61B 1/00149* (2013.01); *A61B 1/313* (2013.01); *A61B 34/30* (2016.02);
(Continued)

(58) Field of Classification Search
CPC . A61B 1/00149; A61B 1/313; A61B 1/00128; A61B 34/30; A61B 90/50; A61B 90/98; A61B 2034/2051; A61B 2090/508
See application file for complete search history.

(56) References Cited

U.S. PATENT DOCUMENTS

| 4,854,301 A | 8/1989 | Nakajima |
| 5,406,859 A | 4/1995 | Belford |

(Continued)

FOREIGN PATENT DOCUMENTS

| WO | 2003094759 A1 | 11/2003 |
| WO | 2010122563 A1 | 10/2010 |

OTHER PUBLICATIONS

International Search Report and Written Opinion from International Application No. PCT/IL2010/000330 dated Jul. 30, 2010.
(Continued)

*Primary Examiner* — Timothy J Neal
*Assistant Examiner* — William B Chou
(74) *Attorney, Agent, or Firm* — JCIPRNET

(57) ABSTRACT

The present invention provides a two-part robotic device for positioning of a hand tool, comprising:
a. a fixed base unit constantly fix to its position;
b. a detachable body unit reversibly coupled to said fixed base unit, coupled to said current medical instrument;
wherein said fixed base unit is adapted to provide independent movement to said hand tool, said independent movement selected from the group consisting of rotation and translation, and further wherein said detachable body unit is removable and replaceable from said fixed base unit such that upon exchange of said hand tool for a second hand tool, said second hand tool is placed in substantially the same location as the location of said hand tool prior to said exchange.

18 Claims, 50 Drawing Sheets

Related U.S. Application Data

No. 15/086,194, filed on Mar. 31, 2016, now Pat. No. 10,426,321, which is a division of application No. 13/265,206, filed as application No. PCT/IL2010/000330 on Apr. 22, 2010, now abandoned.

(60) Provisional application No. 61/324,324, filed on Apr. 15, 2010, provisional application No. 61/171,848, filed on Apr. 23, 2009.

(51) Int. Cl.
 *A61B 90/50* (2016.01)
 *A61B 34/30* (2016.01)
 *A61B 90/98* (2016.01)
 *A61B 34/20* (2016.01)

(52) U.S. Cl.
 CPC .............. *A61B 90/50* (2016.02); *A61B 90/98* (2016.02); *A61B 1/00128* (2013.01); *A61B 2034/2051* (2016.02); *A61B 2090/508* (2016.02)

(56) References Cited

U.S. PATENT DOCUMENTS

| | | | |
|---|---|---|---|
| 5,878,193 A | 3/1999 | Wang et al. |
| 5,954,586 A | 9/1999 | Kirson |
| 6,451,027 B1 | 9/2002 | Cooper |
| 6,569,084 B1 | 5/2003 | Mizuno et al. |
| 6,714,841 B1 | 3/2004 | Wright et al. |
| 6,723,106 B1 | 4/2004 | Charles |
| 8,123,675 B2 | 2/2012 | Funda et al. |
| 8,435,171 B2 | 5/2013 | Sholev |
| 2002/0151795 A1 | 10/2002 | Palti |
| 2002/0166403 A1 | 11/2002 | Choset et al. |
| 2003/0062858 A1 | 4/2003 | Shimizu et al. |
| 2004/0024387 A1 | 2/2004 | Payandeh et al. |
| 2005/0256371 A1 | 11/2005 | Schara et al. |
| 2006/0100501 A1 | 5/2006 | Berkelman et al. |
| 2006/0217206 A1 | 9/2006 | Thompson |
| 2007/0142701 A1 | 6/2007 | Goldberg et al. |
| 2007/0299427 A1 | 12/2007 | Yeung et al. |
| 2008/0114376 A1 | 5/2008 | Steinberg |
| 2009/0171373 A1 | 7/2009 | Farritor et al. |
| 2010/0185211 A1 | 7/2010 | Herman et al. |
| 2012/0041263 A1 | 2/2012 | Sholev |
| 2013/0123804 A1 | 5/2013 | Sholev et al. |
| 2014/0163359 A1 | 6/2014 | Sholev et al. |
| 2014/0194896 A1 | 7/2014 | Frimer et al. |
| 2014/0221738 A1 | 8/2014 | Sholev et al. |
| 2014/0228632 A1 | 8/2014 | Sholev et al. |
| 2014/0378763 A1 | 12/2014 | Atarot et al. |
| 2015/0031953 A1 | 1/2015 | Atarot et al. |

OTHER PUBLICATIONS

International Preliminary Report on Patentability from International Application No. PCT/IL2010/000330 dated Oct. 23, 2011.

Arshak K. et al.: "A Model for Estimating the Real-Time Positions of Moving an Object in Wireless Telemetry Applications using RF Sensors", Conference Paper, SAS 2007—IEEE Sensors Applications Symposiu, San-Diego, California, USA, Feb. 6-8, 2007, pp. 1-6.

Extended European Search Report issued by the European Patent Office dated Dec. 18, 2013, for corresponding European Application No. EP10766746.1, filed Apr. 22, 2010.

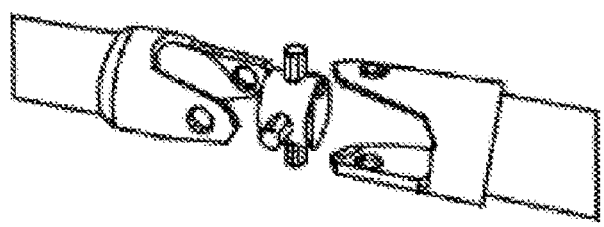
PRIOR ART - FIG. 1A
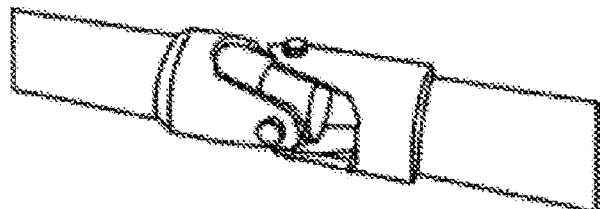
PRIOR ART - FIG. 1B
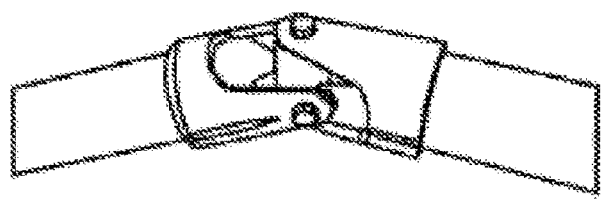
PRIOR ART - FIG. 1C
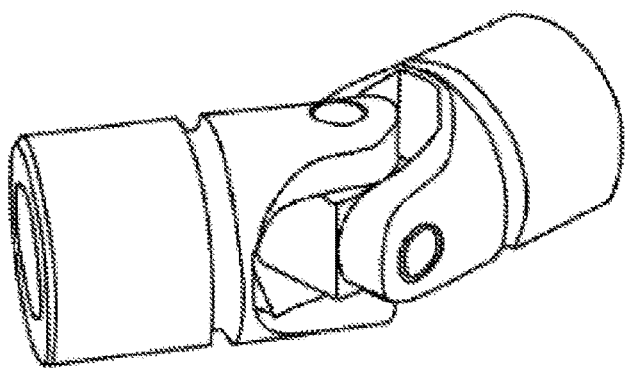
PRIOR ART - FIG. 1D

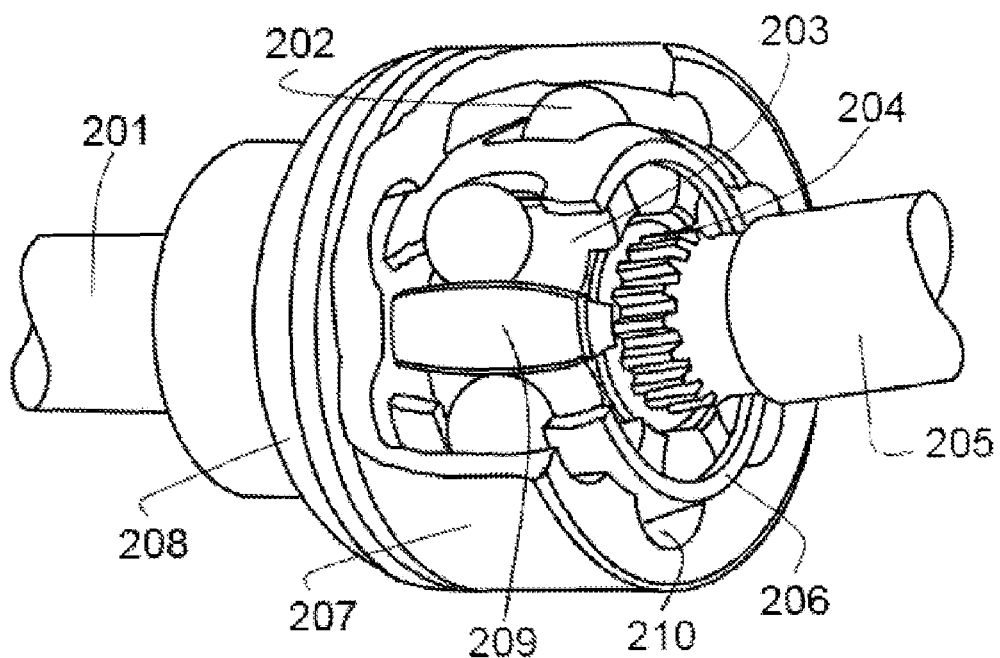
PRIOR ART - FIG. 2A
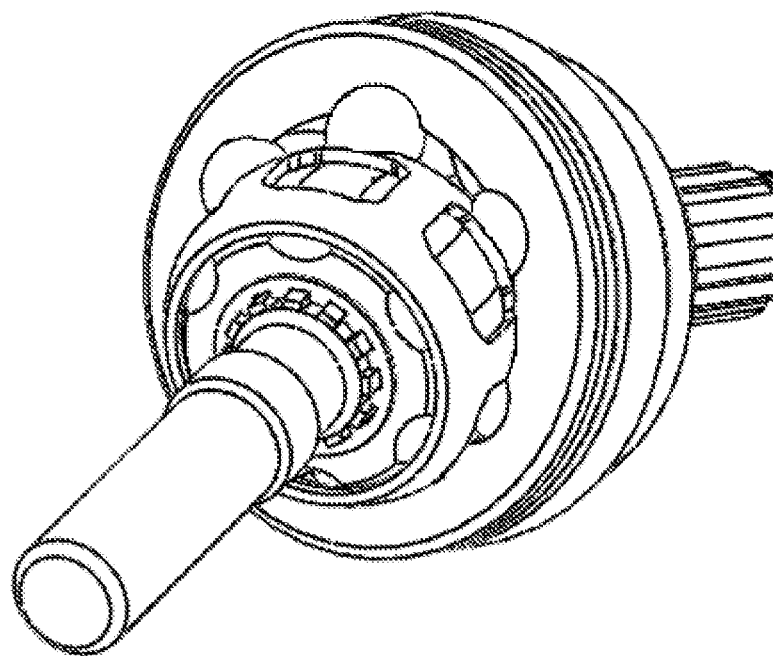
PRIOR ART – FIG. 2B

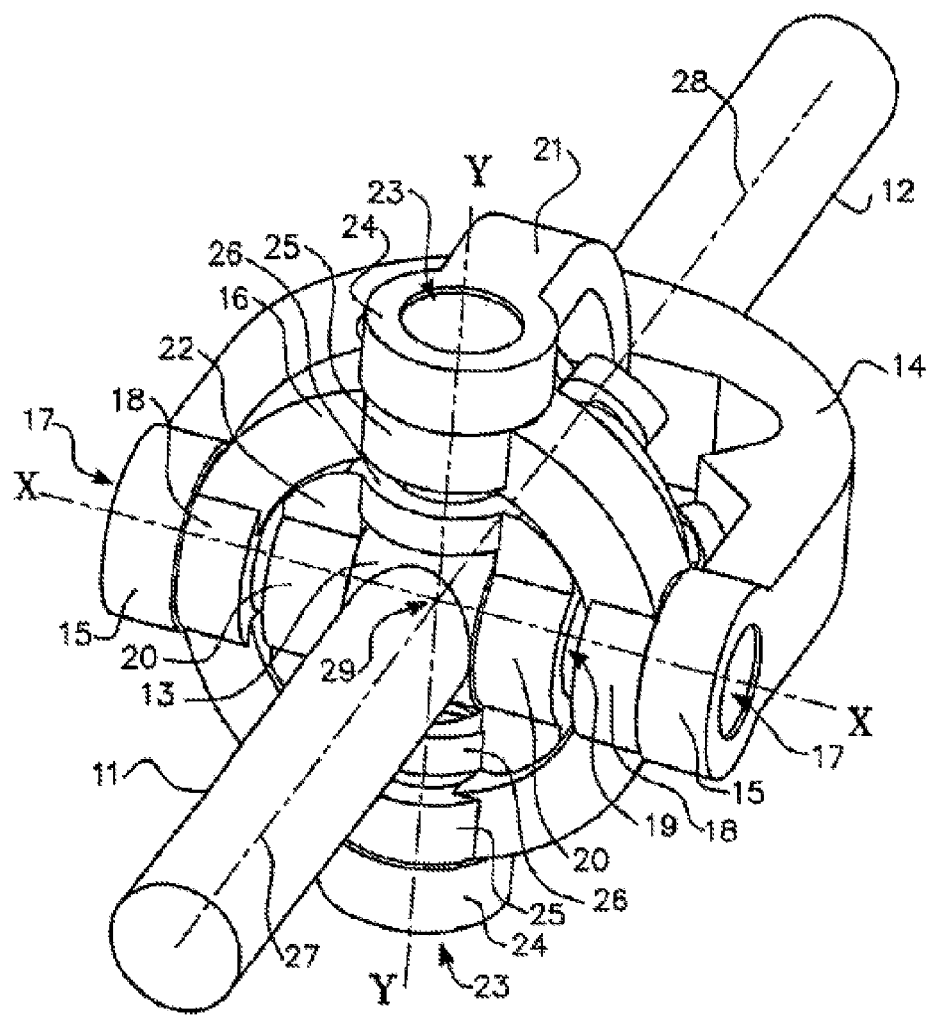
PRIOR ART - FIG. 3

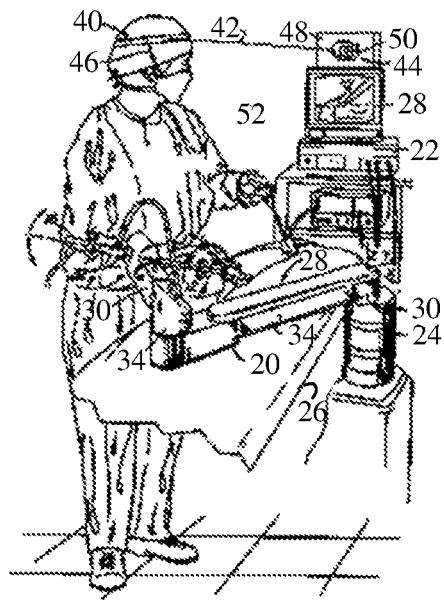
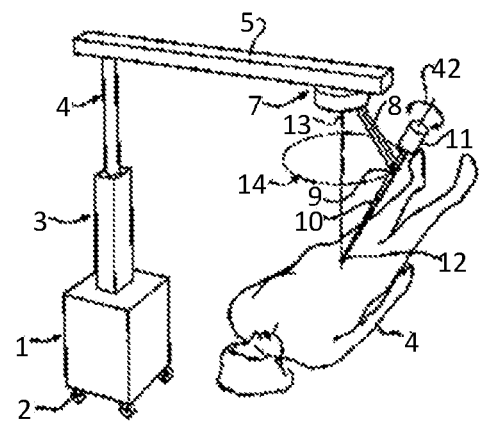
FIG. 14A
FIG. 14B
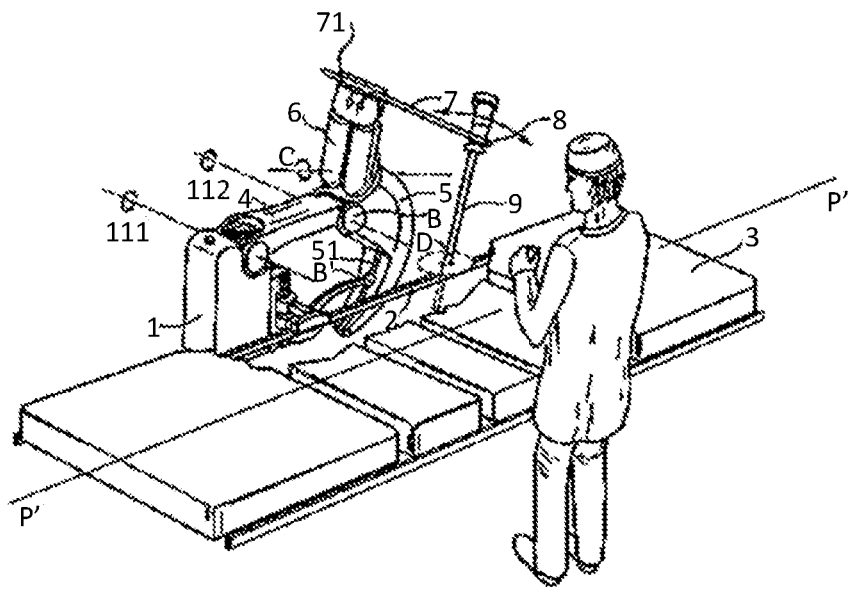
FIG. 14C
PRIOR ART

FIG. 26A
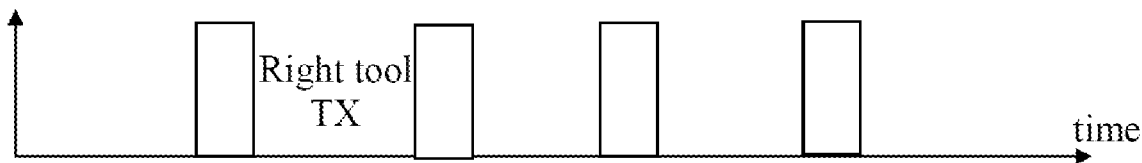
FIG. 26B
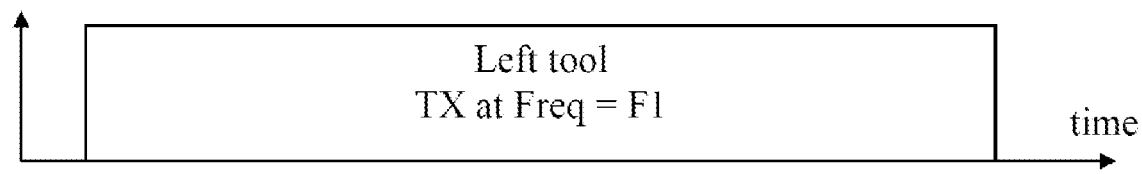
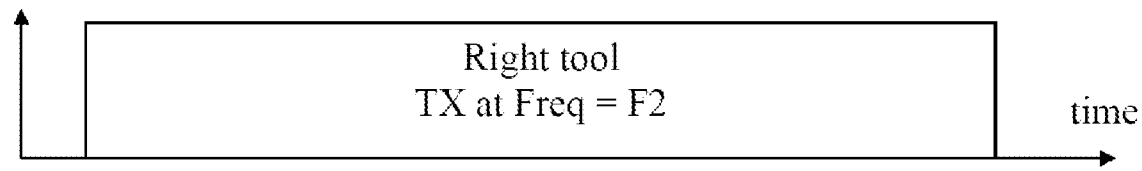
FIG. 26C

TWO-PART ENDOSCOPE SURGICAL DEVICE

CROSS REFERENCE TO RELATED APPLICATIONS

This application is a continuation of U.S. application Ser. No. 16/590,268, filed on Oct. 1, 2019, which is a continuation of U.S. application Ser. No. 15/086,194, filed Mar. 31, 2016, now U.S. patent Ser. No. 10/426,321, issued Oct. 1, 2019, which is a divisional of U.S. application Ser. No. 13/265,206, filed Oct. 19, 2011, which is a U.S. National Stage entry of International PCT Application No. PCT/IL2010/000330, filed Apr. 22, 2010, which claims priority from Provisional Application No. 61/324,324, filed Apr. 15, 2010, and from Provisional Application No. 61/171,848, filed Apr. 23, 2009. All of these applications are hereby incorporated by reference in their entirety.

FIELD OF THE INVENTION

The present invention relates to a method and apparatus for laparoscopic surgery using a two-part device composed of a base unit and a detachable body unit. The invention furthermore relates to the guiding of such laparoscopic instruments and procedures, and in particular to interfaces that allow identification of the spatial position of a laparoscope during endoscopic surgery.

BACKGROUND OF THE INVENTION

In laparoscopic surgery, the surgeon performs the operation through one or more small incisions using long instruments, while observing the internal anatomy with an endoscope camera. The laparoscope is often provided with some form of gantry or holding unit to hold the external portion of the device in place. This gantry is often a somewhat cumbersome apparatus and is in general associated with a particular laparoscopic device. Each form of surgical laparoscope will have its own gantry which must be installed before use.

For example U.S. Pat. No. 5,878,193 provides a robotic system that moves a surgical instrument in response to the actuation of a control panel that can be operated by the surgeon. The robotic system has an end effector that is adapted to hold a surgical instrument such as an endoscope. The end effector is coupled to a robotic arm assembly which can move the endoscope relative to the patient. The system includes a computer which controls the movement of the robotic arm in response to input signals received from the control panel. The robotic system is mounted to a cart which can be wheeled to and from an operating table.

An example of laparoscopic surgery is Functional Endoscopic Sinus Surgery (FESS) used to relieve blockages and discomfort in the nasal sinuses—a commonly performed operation.

During laparoscopic surgery it is often required to shift the spatial placement of the endoscope in order to present the surgeon with an optimal view. Conventional laparoscopic surgery makes use either of human assistants who manually shift the instrumentation or alternatively of robotic automated assistants. Automated assistants utilize interfaces that enable the surgeon to direct the mechanical movement of the assistant, achieving a shift in the camera view. U.S. Pat. No. 6,714,841 discloses an automated camera endoscope in which the surgeon is fitted with a head mounted light source that transmits his head movements to a sensor, forming an interface that converts said movements to directions for the mechanical movement of the automated assistant. Alternative automated assistants incorporate a voice operated interface, a directional key interface, or other navigational interfaces. The main disadvantage of the above interfaces is that they are based on cumbersome operations for starting and stopping movement directions that requires the surgeon's constant attention.

Arshak's article "A Model for Estimating the Real Time Positions of a Moving Object in Wireless Telemetry Applications Using RF Sensors" (Arshak, K.; Adepoju, F. Sensors Applications Symp. 2007, 1-6) relates to a method for locating a transmitting object using multiple receiving antenna sensors located at various place surrounding the transmitting device. The receiver antennas are assumed to be omni-directional and the location of the transmitter is achieved through distance estimation (i.e., triangulation) from each of the receiving antennae.

The distance from the transmitter is estimated by measuring the received signal strength (RSS) of the received signal, where the estimated RSS (in dB) is given by the following equation:

$$RSS = PT - PL(do) - 10 ri \log io(d/do) + X,$$

where PT is the transmitted power, PL(do) is the path loss for a reference distance do, ri is the pass loss exponent, d is the distance between the transmitter and the receiver, and X, is a Gaussian random variable.

Therefore, the signal received is proportional to PT and the $n^{th}$ power of distance to the transmitter. In free space, ri is normally equal to 2. The location of the transmitter can thus be determined by using the above equation to calculate the distance to each of the receiving antennas and triangulating. Arshak states in the article that other methods such as time of arrival, time differences of arrival and angle of arrival are not feasible in dense, multipath environments. If, however, the transmission power is unknown, unstable or inaccurate, or if the propagation factor is unknown, then Arshak's method cannot be used. An efficient method for enabling the relative position of the transmitter (and thus the medical instrument) to be determined therefore remains a long-felt need.

Research has suggested that these systems divert the surgeon's focus from the major task at hand. Therefore technologies based on various kinds of positioning systems have been developed to simplify interfacing control. These technologies still fail to address another complicating interface aspect of laparoscopic surgery, however, as they do not allow the surgeon to signal both to the automated assistant and to surgical colleagues on which surgical instrument his attention is focused.

Hence, a system for laparoscopic surgery providing multiple laparoscopic tools while employing a single external holding device is a long felt need, especially in the field of sinus surgery. Additionally there is a further long-felt need for a device that would allow the surgeon to identify to the laparoscopic computing system as well as to surgical colleagues to which surgical instrument attention is to be directed, thereby directing the view provided by the endoscope to the selected area of interest.

BRIEF DESCRIPTION OF THE DRAWINGS

In order to understand the invention and to see how it may be implemented in practice, a plurality of embodiments will now be described, by way of non-limiting example only, with reference to the accompanying drawings, in which FIGS. 1A-D presents a Universal Joint, also known as the U-joint or Cardan joint;

FIGS. 2A-B presents a constant-velocity or CV joint;

FIG. 3 presents a Thompson joint, this being a type of double Cardan joint;

FIGS. 14A-14C presents laparoscopic positioning systems of the prior art;

FIGS. 26A-C schematically illustrates methods of operation, with FIG. 26A schematically illustrating sequential transmit operation, FIG. 26B schematically illustrating periodic transmit operation, with unequal rates for left and right transmitters and FIG. 26C schematically illustrating simultaneous transmit operation with different frequencies;

SUMMARY OF THE INVENTION

Figure 4:
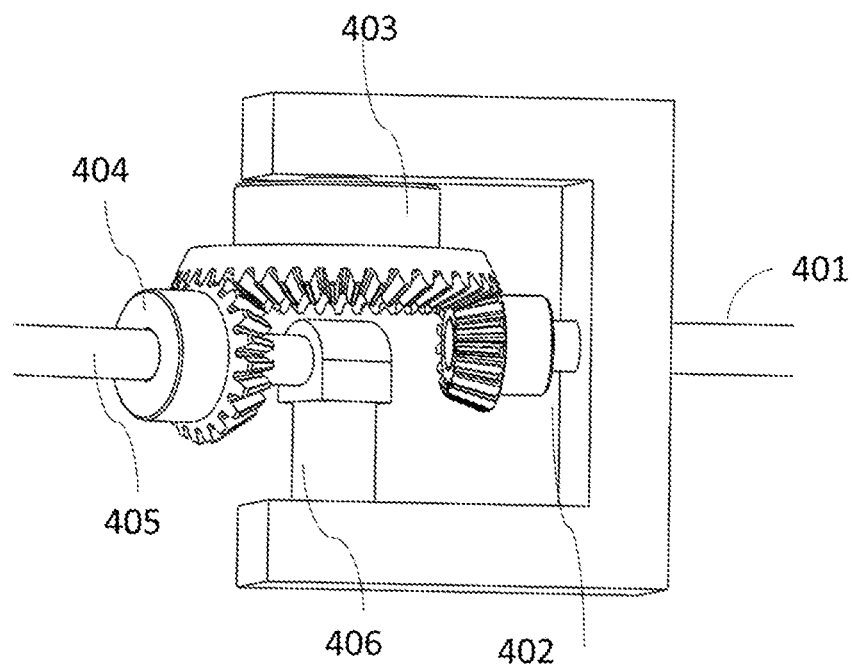
FIG. 4 presents a isometric view of an embodiment of the variable coupling of the present invention.

It is an object of the invention to provide a laparoscope composed of a set of detachable parts. A base unit attaches to a fixed location such as the floor, the side of an operating table, or the like. A body unit attaches to this base unit and is provided with a laparoscope and associated devices, such as surgical tools, camera, fiber optics, light sources, and the like. The body unit attaches easily to the base unit and is supported by it during surgery. It may be detached and replaced with another body unit suitable for different procedures. The device utilizes a novel torque-transmitting joint that allows a large number of degrees of freedom to be transmitted while allowing the several sections of the device to be rotated and translated through additional degrees of freedom. In this way a simple and modular means for performing a wide variety of surgical procedures is attained.

It is thus an object of the present invention to disclose a two-part robotic device for positioning of a hand tool, comprising (a) a fixed base unit constantly fix to its position; and (b) a detachable body unit reversibly coupled to said fixed base unit, coupled to said current medical instrument.

It is within the essence of the invention wherein said fixed base unit is adapted to provide independent movement to said hand tool, said independent movement selected from the group consisting of rotation and translation, and further wherein said detachable body unit is removable and replaceable from said fixed base unit such that upon exchange of said hand tool for a second hand tool, said second hand tool is placed in substantially the same location as the location of said hand tool prior to said exchange.

It is a further object of the present invention to disclose such a two-part robotic device, wherein said hand tool is a medical instrument.

It is another object of the present invention to provide the two-part robotic device as defined above, wherein said medical instrument is selected from a group consisting of endoscope, laparoscope, forceps, or any combination thereof.

It is another object of the present invention to provide the two-part robotic device as defined above, wherein said detachable unit is an endoscope positioning device adapted to provide said endoscope at least 7 DOF selected from a group consisting of at least 6 rotation movements (1007, 1009, 1010, 1011, 1012, 1013, 1601, 1602), at least 1 translation movement (1008) or any combination thereof.

It is another object of the present invention to provide the two-part robotic device as defined above, wherein said detachable unit comprises:
a. k consecutive arm sections, each comprising n coaxial input shafts adapted to be rotated around an input axis of rotation by m sources of torque, where n and m and k are positive integers; said current instrument is coupled to one of said k consecutive arm sections;
b. at least k−1 constant velocity couplers coupling each two of said k consecutive arm sections together, each of said constant velocity coupler comprising:
  i. n coaxial input transmission means, each of which is coupled to one of said n input shafts; said input transmission means defining a first plane substantially perpendicular to said input axis of rotation;
  ii. n coaxial second transmission means rotatably connected to said n input transmission means; said second transmission means rotating in a second plane, such that said second plane is substantially perpendicular to said first plane;
  iii. n coaxial output transmission means rotatably connected to said n second transmission means; said output transmission means rotating in a third plane; said third plane being substantially perpendicular to said second plane;
c. n coaxial output shafts, each of which is coupled to one of said n output transmission means, said n output shafts being adapted to rotate around an output axis of rotation; such that (i) turning a given input shaft at a constant velocity will provide a constant velocity at the corresponding output shaft; and, (ii) the angle between said input axis of rotation and said output axis of rotation varies in said second plane in an angular range of about 0 to about 360 degrees.

It is another object of the present invention to provide the two-part robotic device as defined above, wherein said fixed base unit comprises:
a. k consecutive arm sections, each comprising n coaxial input shafts adapted to be rotated around an input axis of rotation by m sources of torque, where n and m and k are positive integers; said current instrument is coupled to one of said k consecutive arm sections;
b. at least k−1 constant velocity couplers coupling each two of said k consecutive arm sections together, each of said constant velocity coupler comprising:
  i. n coaxial input transmission means, each of which is coupled to one of said n input shafts; said input transmission means defining a first plane substantially perpendicular to said input axis of rotation;
  ii. n coaxial second transmission means rotatably connected to said n input transmission means; said second transmission means rotating in a second plane, such that said second plane is substantially perpendicular to said first plane;
  iii. n coaxial output transmission means rotatably connected to said n second transmission means; said output transmission means rotating in a third plane; said third plane being substantially perpendicular to said second plane;
c. n coaxial output shafts, each of which is coupled to one of said n output transmission means, said n output shafts being adapted to rotate around an output axis of rotation; such that (i) turning a given input shaft at a constant velocity will provide a constant velocity at the corresponding output shaft; and, (ii) the angle between said input axis of rotation and said output axis of rotation varies in said second plane in an angular range of about 0 to about 360 degrees.

It is another object of the present invention to provide the two-part robotic device as defined above, wherein said input transmission means, second transmission means, and said output transmission means are selected from a group consisting of gearwheels, wheels, crown gears, bevel gears, spur gears, belts, or any combination thereof.

It is another object of the present invention to provide the two-part robotic device as defined above, additionally comprising
a. an axial support member (601) adapted to provide axial support to said n output shafts in said third plane; and,
b. a circular track (618) centered on the axis of rotation of said second transmission means, said axial support member being adapted to fit into said track and slide within it.

It is another object of the present invention to provide the two-part robotic device as defined above, additionally comprising a radial support member (604) adapted to provide radial support to said n output shafts, said radial support member being adapted to rotate in said second plane.

It is another object of the present invention to provide the two-part robotic device as defined above, wherein the gear ratio between said input and output shafts is between about 10 and about 0.1.

It is another object of the present invention to provide the two-part robotic device as defined above, additionally comprising n coaxial auxiliary shafts in rotating communication with said n second transmission means, said n coaxial auxiliary shafts rotating in said second plane, and said n coaxial auxiliary shafts capable of either being driven by said input shafts or driving said input shafts.

It is another object of the present invention to provide the two-part robotic device as defined above, additionally comprising locking means adapted for preventing relative movement between one or more of said input axis shafts and said constant velocity joint, wherein said constant velocity joint is caused to rotate as a body with said locked input axis shafts.

It is another object of the present invention to provide the two-part robotic device as defined above, additionally comprising locking means for preventing relative movement between one or more of said output axis shafts and said constant velocity joint, wherein said constant velocity joint is caused to rotate as a body with said locked output axis shafts.

It is another object of the present invention to provide the two-part robotic device as defined above, adapted for use in sinus surgery.

It is another object of the present invention to provide the two-part robotic device as defined above, wherein said sinus surgery is FESS.

It is another object of the present invention to provide a method for altering a current medical instrument in use whilst performing a laparoscopic surgery. The method comprises steps of:
a. providing a two-part robotic device comprising:
  i. a fixed base unit, constantly fix to its position;
  ii. a detachable body unit reversibly coupled to said fixed base unit, comprising said current medical instrument;
b. coupling said detachable body unit to said fixed base;
c. providing independent movements to said current medical instrument selected from a group consisting of rotation and translation; thereby performing said laparoscopic surgery;
d. detaching said detachable body unit from said fixed base unit; and,
e. replacing said current medical instrument in said detachable body unit thereby altering said current medical instrument.

It is a further object of the present invention to provide a method of altering the modality of a laparoscopic surgery. The method comprises steps of:
a. providing a two-part robotic device comprising:
  iii. a fixed base unit, constantly fix to its position;
  iv. a first detachable body unit reversibly coupled to said fixed base unit, comprising said current medical instrument; said first detachable body unit is adapted for laparoscopic surgery of a first modality;
b. coupling said first detachable body unit to said fixed base;
c. providing independent movements to said current medical instrument selected from a group consisting of rotation and translation; thereby performing said laparoscopic surgery of said first modality with said first detachable body unit;
d. providing a second detachable body unit adapted for laparoscopic surgery of a second modality;
e. decoupling said first detachable body unit from said fixed base;
f. coupling said second detachable body unit for laparoscopic surgery of a second modality;
g. performing laparoscopic surgery of said second modality with said second detachable body unit; thereby altering the modality of said laparoscopic surgery.

It is a further object of the present invention to disclose an interface between a surgeon and an automated assistant, comprising (a) at least one array comprising N RF transmitters, where N is a positive integer; (b) one RF receiver, provided with at least one directional antenna; (c) means for attaching said RF transmitter array to at least one surgical tool; and, (d) a computerized operating system adapted to record the received signal strength (RSS) received by said RF receiver and to calculate therefrom the position of each of said N RF transmitters, and further adapted to provide automatically the results of said calculation to the human operator of said interface. It is within the essence of the invention wherein said computerized operating system calculates at least one of the parameters chosen from the group consisting of
(a) the angle from which the signal had been received; (b) the spatial location of said at least one surgical tool; (c) the path of said at least one surgical tool; (d) the spatial location of the point of insertion of said at least one surgical tool into the body of a patient; (e) the spatial location of the tip of said at least one surgical tool; (f) matching each RF transmitter code with each calculated spatial location of said at least one surgical tool and/or said tip of said at least one surgical tool, and further wherein said computerized operating system provides automatically the results of said calculation to the human operator of said interface.

It is a further object of this invention to disclose such an interface, further comprising an endoscopic device.

It is a further object of this invention to disclose such an interface, wherein said endoscopic device comprises optical imaging means, and further wherein said computerized operating system calculates at least one of the parameters chosen from the group consisting of (a) the spatial location of said at least one surgical tool; (b) the path of said at least one surgical tool; (c) the spatial location of the point of insertion of said at least one surgical tool into the body of a patient; (d) the spatial location of the tip of said at least one surgical tool; (e) matching each RF transmitter code with each calculated spatial location of said at least one surgical tool and/or said tip of said at least one surgical tool; (f) the predicted appearance of said at least one surgical tool within said optical image; (g) if more than one of said at least one surgical tools appears simultaneously in said optical image, distinguishing among said more than at least surgical tools appearing in said optical image, and further wherein said computerized operating system provides automatically the results of said calculation to the human operator of said interface.

It is a further object of this invention to disclose such an interface, further comprising (a) a automated assistant for said endoscopic device; and (b) means for interfacing said computerized operating system to said automated assistant. It is within the essence of the invention wherein said computerized operating system calculates at least one of the parameters chosen from the group consisting of (a) the spatial location of said at least one surgical tool; (b) the path of said at least one surgical tool; (c) the spatial location of the point of insertion of said at least one surgical tool into the body of a patient; (d) the spatial location of the tip of said at least one surgical tool; (e) matching each RF transmitter code with each calculated spatial location of said at least one surgical tool and/or said tip of said at least one surgical tool; (f) a desired new location for said endoscopic device; (g) command protocol means for directing said automated assistant via said interface to maneuver said endoscopic device to a desired new location, and further wherein said computerized operating system provides automatically the results of said calculation to the human operator of said interface.

It is a further object of this invention to disclose such an interface, wherein said endoscopic device comprises optical imaging means, and further wherein said computerized operating system calculates at least one of the parameters chosen from the group consisting of (a) the spatial location of said at least one surgical tool; (b) the path of said at least one surgical tool; (c) the spatial location of the point of insertion of said at least one surgical tool into the body of a patient; (d) the spatial location of the tip of said at least one surgical tool; (e) matching each RF transmitter code with each calculated spatial location of said at least one surgical tool and/or said tip of said at least one surgical tool; (f) the predicted appearance of said at least one surgical tool within said optical image; (g) if more than one of said at least one surgical tools appears simultaneously in said optical image, distinguishing among said more than at least surgical tools appearing in said optical image; (h) a desired new location for said optical imaging means; (i) a command protocol for directing said automated assistant via said interface to maneuver said endoscopic device to a desired new location, and further wherein said computerized operating system provides automatically the results of said calculation to the human operator of said interface.

It is a further object of this invention to disclose such an interface, wherein said computer controller additionally transmits a command protocol to said automated assistant via said interface to maneuver said endoscopic device to a desired new location.

It is a further object of this invention to disclose such an interface, wherein said interface is adapted for manual operation, whereby each of said N transmitters transmits in response to a command signal from the human operator of the interface.

It is a further object of this invention to disclose such an interface, wherein said interface is adapted for automatic operation, whereby each of said N transmitters transmits continuously.

It is a further object of this invention to disclose such an interface, wherein said interface is adapted for automatic operation, whereby each of said N transmitters transmits continuously and further wherein said computer transmits said calculated parameters for each of said N transmitters in response to a command signal from the human operator of the interface.

It is a further object of this invention to disclose such an interface, wherein said antenna array comprises at least one directional antenna.

It is a further object of this invention to disclose such an interface, wherein said transmitters transmit in the 430 MHz ISM band.

It is a further object of this invention to disclose such an interface, wherein M=1, and further wherein said receiver array is adapted to determine the angle whose vertex is the location of said antenna array and which is subtended by the line connecting any two of said N transmitters.

It is a further object of this invention to disclose such an interface, wherein said interface comprises M receivers, M is an integer higher than 1; and further wherein said M receivers are adapted to determine the location of each of said N transmitters by triangulation.

It is a further object of this invention to disclose such an interface, wherein said transmitters transmit a modulated signal, said modulation chosen from the group consisting of (a) frequency modulation, (b) amplitude modulation.

It is a further object of this invention to disclose such an interface, wherein said modulation occurs at a frequency of about 1.5 kHz.

It is a further object of this invention to disclose such an interface, wherein each of said N RF transmitters is modulated at a different frequency.

It is a further object of this invention to disclose such an interface, wherein said N modulation frequencies are chosen from the band of frequencies spanning the range of from about 1.0 kHz to about 1.5 kHz.

It is a further object of this invention to disclose such an interface, wherein receiver is a single conversion receiver.

It is a further object of this invention to disclose a method for calculating positional parameters of a laparoscopic surgical tool, comprising the steps of (a) obtaining an interface for a laparoscope, said interface comprising (i) at least one array comprising NRF transmitters, where N is a positive integer, (ii) one RF receiver provided with at least one directional antenna; (iii) a computerized operating system adapted to record the received signal strength RSS received by each antenna of said RF receiver and to calculate therefrom the position of each of said N RF transmitters, and further adapted to provide automatically the results of said calculation to the human operator of said interface; (b) obtaining a surgical tool; (c) attaching said RF transmitter array to said surgical tool; (d) measuring the received signal strength (RSS) from said N RF transmitters received at each of said directional antenna of said RF receivers; and (e) calculating spatial parameters relating to each of said N transmitters according to a predetermined protocol. It is in the essence of the invention wherein said step of calculating said parameters of each of said N transmitters yields positional parameters of said laparoscope surgical tool, said positional parameters is selected from a group consisting of (a) the angle from which the signal had been received; (b) the spatial location of said at least one surgical tool; (c) the path of said at least one surgical tool; (d) the spatial location of the point of insertion of said at least one surgical tool into the body of a patient; (e) the spatial location of the tip of said at least one surgical tool; (f) matching each RF transmitter code with each calculated spatial location of said at least one surgical tool and/or said tip of said at least one surgical tool, and further wherein said computerized operating system provides automatically the results of said calculation to the human operator of said interface.

It is a further object of this invention to disclose a method for controlling the position of an endoscopic device, comprising the steps of (a) obtaining an interface between a surgeon and an automated assistant, said interface comprising (i) at least one array comprising NRF transmitters, where N is a positive integer, (ii) one RF receiver provided with at least one directional antenna; (iii) a computerized operating system adapted to record the received signal strength RSS received by each antenna of said RF receiver and to calculate therefrom the position of each of said NRF transmitters, and further adapted to provide automatically the results of said calculation to the human operator of said interface; (iv) an automated assistant for said endoscopic device; and, (v) means for interfacing said computerized operating system to said automated assistant; (b) obtaining a surgical tool; (c) attaching said RF transmitter array to said surgical tool; (d) measuring the received signal strength (RSS) from said N RF transmitters received at each of said directional antenna of said RF receivers; (e) calculating spatial parameters relating to location of each of said N transmitters; (f) calculating a desired new position for said endoscopic device; (g) sending a command from said computerized operating system to said automated assistant via said interfacing means to maneuver said endoscopic device to said desired new location; and, (h) maneuvering said endoscopic device to said desired new location It is in the essence of the invention wherein said step of calculating said parameters of each of said N transmitters yields positional parameters of said laparoscope surgical tool, said positional parameters is selected from a group consisting of (a) the angle from which the signal had been received; (b) the spatial location of said at least one surgical tool; (c) the path of said at least one surgical tool; (d) the spatial location of the point of insertion of said at least one surgical tool into the body of a patient; (e) the spatial location of the tip of said at least one surgical tool; (f) matching each RF transmitter code with each calculated spatial location of said at least one surgical tool and/or said tip of said at least one surgical tool, and further wherein said computerized operating system provides automatically the results of said calculation to the human operator of said interface.

It is a further object of this invention to disclose such an interface, wherein said endoscopic device comprises optical imaging means, and further comprising the additional steps of (a) determining said position of said surgical tool relative to the image frame; and (b) maneuvering said optical imaging means such that said surgical tool appears at a predetermined location within said image frame.

It is a further object of this invention to provide such a method, wherein each of said N transmitters transmits in response to a signal from the human operator of said interface.

It is a further object of this invention to provide such a method, wherein each of said N transmitters transmits continuously.

The device of the present invention has many technological advantages, among them simplification of the communication interface between surgeon and automated assistants; seamless interaction with conventional computerized automated endoscope systems; simplicity of construction; reliability; and user-friendliness. Additional features and advantages of the invention will become apparent from the following drawings and description.

DETAILED DESCRIPTION OF THE PREFERRED EMBODIMENTS

The following description is provided to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a two-part endoscopic surgical device which is composed of a positioning section (namely the endoscope/laparoscope) and a fixed section (e.g., tubular arm) coupled to the bed of the patient. The core concept of the present invention lies in the fact that the positioning section may be removed entirely from the fixed section e.g. for replacement, repair, cleaning, etc. It will be apparent to one skilled in the art that there are several embodiments of the invention that differ in details of construction, without affecting the essential nature thereof, and therefore the invention is not limited by that which is illustrated in the figures and described in the specification, but only as indicated in the accompanying claims, with the proper scope determined only by the broadest interpretation of said claims.

The present invention provides a two-part robotic device used for exchanging the current medical instrument in used during laparoscopic surgery. The device comprises (a) a fixed base unit; and (b) a detachable body unit reversibly coupled to said fixed base unit, comprising said current medical instrument.

It is emphasized that the detachable body unit is removable and replaceable from said fixed base unit such that said current medical instrument is altered.

The present invention provides a method for exchanging a current medical instrument in used whilst performing a laparoscopic surgery. The method comprises steps of:

(a) providing a two-part robotic device comprising:
  (i) a fixed base unit;
  (ii) a detachable body unit reversibly coupled to said fixed base unit, comprising said current medical instrument;
(b) coupling said detachable body unit to said fixed base;
(c) performing said laparoscopic surgery;
(d) detaching said detachable body unit from said fixed base unit; and,
(e) replacing said current medical instrument in said detachable body unit thereby exchanging said current medical instrument.

In the following detailed description, numerous specific details are set forth in order to provide a thorough understanding of embodiments of the present invention. However, those skilled in the art will understand that such embodiments may be practiced without these specific details. Reference throughout this specification to "one embodiment" or "an embodiment" means that a particular feature, structure, or characteristic described in connection with the embodiment is included in at least one embodiment of the invention.

As used herein, the term "gear ratio" in a transmission with an input shaft and an output shaft refers to the ratio of angular velocity of the output shaft to that of the input shaft.

As used herein, the term "transmission means" refers to means for transferring torque from one rotating element to another, such as gearwheels, wheels, crown gears, and the like.

As used herein, the terms "endoscope" and "laparoscope" refer interchangeably to a fiber optical device that consists of a flexible tube. Glass or plastic filaments allow total internal reflection of light for viewing. This medical device is used in laparoscope, endoscope, laparoscopic and endoscopic surgeries. It is also in the scope of the invention wherein the terms refer also to any means for looking within body cavities, especially inside the human body and mammalian body for medical reasons using an instrument; and especially to means for minimally invasive diagnostic medical procedure, such as rigid or flexible endoscopes, fiberscopes, means for robotic surgery, trocars, surgical working tools and diagnosing means etc.

As used herein, the terms "endoscopic surgery" and "laparoscopic surgery" interchangeably refer to a modern surgical technique in which operations upon the body of a patient, e.g., within the abdomen, are performed through small incisions (usually 0.5 to 1.5 cm) as compared to larger incisions needed in traditional surgical procedures. Laparoscopic surgery includes e.g., operations within the abdominal, pelvic or joint cavities. Endoscopic surgery involves, inter alia, operations in the gastrointestinal tract, e.g., in the esophagus, stomach and duodenum (esophagogastroduodenoscopy), small intestine, colon (colonoscopy, proctosigmoidoscopy), bile duct, endoscopic retrograde cholangiopancreatography (ERCP), duodenoscope-assisted cholangiopancreatoscopy, intraoperative cholangioscopy, the respiratory tract, the nose (rhinoscopy), the lower respiratory tract (bronchoscopy), the urinary tract (cystoscopy), the female reproductive system, the cervix (colposcopy), the uterus (hysteroscopy), the Fallopian tubes (falloscopy), normally closed body cavities (through a small incision), the abdominal or pelvic cavity (laparoscopy), the interior of a joint (arthroscopy) organs of the chest (thoracoscopy and mediastinoscopy), the amnion during pregnancy (amnioscopy), the fetus (fetoscopy), plastic surgery, panendoscopy, laryngoscopy, esophagoscopy; and various nonmedical uses for endoscopy. The term also refers to any manipulation of laparoscopes and endoscopes as defined above into the body of a patient.

As used herein, the term "degrees of freedom" (DOF) refers hereinafter to a set of independent displacements that specify completely the displaced position of the endoscope or laparoscope as defined above. In three dimensional space, there are six DOF, three DOF of linear displacement and three rotational DOFs, namely, moving up and down, moving left and right, moving forward and backward, tilting up and down, turning left and right, tilting side to side. The present invention refers to a system essentially comprising means for providing a total of at least seven DOF (i.e. DOF for components of a multiple-component system, wherein at least a portion of the DOF of a given component are independent of those of the other components of the system) selected from any of those that will be described hereinafter.

As used herein, the term "distal portion" refers to the end of the endoscope designed to be located within the body of the patient while the endoscope is in use, and the term "proximal portion" to the end of the endoscope designed to be located outside the body of the patient while the endoscope is in use.

As used herein, the term "base unit" refers to a rigid unit attached to a fixed point in space such as the floor, ceiling, surgical table, or the like. The base is adapted to attach to a laparoscope and transmit various necessary elements to and from it including torques, light, voltages, video signals, and fluids.

As used herein, the term "body unit" refers to a laparascopic surgical instrument adapted to attach to a base unit. The base unit provides physical support to the body unit, which must be able to maneuver in several dimensions and with several degrees of freedom. The base unit transmits various necessary elements to the body unit such as torques, voltages, fluids, etc. The body unit generally comprises a laparoscopic instrument and various positioning devices used to change its position and direction.

As used herein, the term "automated assistant" refers to any mechanical device (including but not limited to a robotic device) that can maneuver and control the position of a surgical or endoscopic instrument, and that can in addition be adapted to receive commands from a remote source.

As used herein, the term "antenna gain" refers to the ratio of the radiation intensity of an antenna in a given direction to the intensity that would be produced by a hypothetical ideal antenna that radiates equally in all directions (isotropically) and has no losses.

As used herein, when referring to transmission of information to a human, the term "provide" refers to any process (visual, tactile, or auditory) by which an instrument, computer, controller, or any other mechanical or electronic device can report the results of a calculation or other operation to a human operator.

As used herein, the term "automatic" or "automatically" refers to any process that proceeds without the necessity of direct intervention or action on the part of a human being.

Laparoscopic surgery, also called minimally invasive surgery (MIS), bandaid surgery, keyhole surgery, or pinhole surgery is a modern surgical technique in which operations in the abdomen are performed through small incisions (usually 0.5-1.5 cm) as compared to larger incisions needed in traditional surgical procedures. The key element in laparoscopic surgery is the use of a laparoscope, which is a device adapted for viewing the scene within the body, at the distal end of the laparoscope. Either an imaging device is placed at the end of the laparoscope, or a rod lens system or fiber optic bundle is used to direct this image to the proximal end of the laparoscope. Also attached is a light source to illuminate the operative field, inserted through a 5 mm or 10 mm cannula or trocar to view the operative field. The abdomen is usually insufflated with carbon dioxide gas to create a working and viewing space. The abdomen is essentially blown up like a balloon (insufflated), elevating the abdominal wall above the internal organs like a dome. Within this space, various medical procedures can be carried out. Thus more advanced laparoscopes perform more than visual inspection, for instance performing various surgical procedures such as hernia repair, prostatectomy, liver resection, gastrectomy, and the like.

Generally the laparoscope is held fixed in some fashion, either by an assistant, or on a mechanical support such as a gantry, stand, or the like. For each laparoscopic procedure, in general a different laparoscope is required. Due to the specialized nature of these instruments, the support fixture for the device is generally specific to the device and provided with it as a unit. In order to save space, expense, and complexity, the present invention provides a base unit that is rigidly supported. This base unit in turn provides rigid support to the laproscope. The laparoscope is detachable from the base unit in a modular fashion. Thus other laparoscopic instruments can be attached to the same base station for carrying out different surgeries. The base station is provided with the necessary fixtures to allow operation of a variety of laparoscopes, as will be detailed in the following.

For the performance of increasingly complex medical procedures, a system for transmitting a large number of mechanical degrees of freedom to the proximal end of a laparoscope is desirable. The present invention solves this problem within the constraints dictated by the nature of laparoscopic surgery, namely a small incision diameter, a large distance between actuators (outside the body) and actuated elements (within the body), and the desire to provide the laparoscope with as many independent degrees of freedom as possible.

The present invention provides a rigidly mounted base station and a detachable body unit comprising a laparoscopic surgical device. The main advantage in such a detachable body unit lies in the fact that the fixed unit remains in place while the detachable body (comprising the medical tool to be used) can be altered quickly and easily.

Another key problem to be solved in laparoscopic surgeries is providing the laparoscope with sufficient degrees of freedom. In the device of the current invention this is solved using a novel N-DOF (n degrees of freedom) torque transmitter based on a coaxial constant-velocity joint. This joint will be described in the following.

First we'll describe the coaxial constant-velocity joint and then the coupling of such joint in a laparoscope for providing said N-DOF. Lastly, the two-part robotic device comprising a medical instrument (e.g. an endoscope integrated within it said coaxial constant-velocity joints).

The N-DOF torque transmitter is provided with a series of arms that contain multiple coaxial cylinders, each of which can rotate independently. A novel joint allows two such cylindrical devices to be mated while transmitting the rotations of the coaxial members, allowing the two cylindrical devices to be pivoted with respect to one another. The notion of concentric cylindrical members is simple enough to forego detailed discussion, and thus in the following we concentrate on the design of the joint joining two such cylindrical members.

In many mechanical systems there arises the need to transfer torque from an input shaft to an output shaft. A wide variety of gear systems have been devised for this purpose.

In a number of important cases the output shaft must vary the direction of its axis with respect to the input shaft. This is the case for example in a front-wheel-drive car. The engine must provide torque to the wheels, to move the car forward. However the front wheels must also be allowed to change their axis of rotation, to allow steering of the car.

The so-called universal joint, aka U-joint, Cardan joint, Hardy-Spicer joint, or Hooke's joint is often employed for purposes of allowing variation of the output axis direction. This is a joint in a rigid rod that allows the rod to bend', and is commonly used in shafts that transmit rotary motion. It consists of a pair of ordinary hinges located close together, but oriented at 90° relative to each other. See FIG. 1A-1D for illustrations of this common joint. The concept of the universal joint is based on the design of gimbals, which have been in use since antiquity.

There are several known drawbacks to the simple U-joint. When the two shafts are at an angle other than 180° (straight), the driven shaft does not rotate with constant angular speed in relation to the drive shaft; as the angle approaches 90° the output rotation gets jerkier (and furthermore, when the shafts reach the 90° perpendicular situation, they lock and will not operate at all). We note that our measurement of angle between output and input shaft is consonant with standard mathematical practice. Namely, when the input and output shaft are parallel in the 'unbent' configuration, the angle between them is 180°. As the output shaft is bent, this angle decreases until reaching 90° when the shafts are perpendicular, and 0° when the output shaft is bent back upon the input shaft.

Joints have been developed utilizing a floating intermediate shaft and centering elements to maintain equal angles between the driven and driving shafts, and the intermediate shaft. This overcomes the problem of differential angles between the input and output shafts.

The CV joint or constant velocity joint finds actual use in automotive applications. As shown in FIG. 2A this is a joint connecting the input axle 201 to the output axle 205. The splines 204 spin the spokes 209 which in turn spin the plurality of ball bearings 202 on the inner ball race 203. These balls are confined between the ball cage 206 and the outer socket 207, which has depressions 210 into which the balls fit. Since the balls are confined by both axles, they transfer the torque from the input axle 201 to the output axle 205. An isometric view is given in FIG. 2B. The two main failures are wear and partial seizure. Furthermore it will be appreciated that extreme angles between input and output shafts of around 90 or less will not be capable of transferring torque at all, and in practice a continuous angle of about 100° degrees is the highest deviation from the straight 100° configuration obtainable with a CV joint.

The double Cardan or double U-joint allows for a constant velocity to be attained at the output shaft, unlike the single U-joint. An improvement on this is two Cardan joints assembled coaxially where the cruciform-equivalent members of each are connected to one another by trunnions and bearings which are constrained to continuously lie on the homokinetic plane of the joint. This is the basis of US patent application 20060217206. Therein is disclosed a constant velocity coupling and control system therefore, the so-called 'Thompson coupling', as shown in FIG. 3. A recent innovation, the Thompson coupling is a further development of the double Cardan-joint, which doesn't rely on friction or sliding elements (as the CV joint does) to maintain a strict geometric relationship within the joint, and which is capable of transmitting torque under axial and radial loads with low frictional losses. This coupling has all loads carried by roller bearings, with no sliding or skidding surfaces whatsoever. It can tolerate axial and radial loads without degradation, with no wearing components except replaceable bearings and trunnions, and is less bulky than a double Cardan joint. However as will be appreciated from FIG. 3, this is a rather complex affair.

Furthermore the maximum allowable angles are still restricted to a small range around 180°, e.g. to an instantaneous minimum allowable angle of 155° and minimum continuous angle of 168°.

According to a preferred embodiment of the present invention, a method is provided that allows the transfer of torque from an input shaft to an output shaft, whose axis of rotation may be varied continuously from nearly 0 degrees to nearly 360 degrees with respect to the axis of rotation of the input shaft.

With reference to FIG. 4 a representative embodiment of the invention is detailed. The input shaft 401 is rotated due to torque from some external source. This torque is transmitted to spur gear 402. Spur gear 402 engages crown gear 403, which therefore rotates and transmits torque to spur gear 404. It will be appreciated by one skilled in the art that the spur and crown gears could be replaced with bevel gears. This simple arrangement is well known in the form of the bevel gear reversing mechanism. The key inventive step of the present invention is to allow the output shaft 405 to rotate not only about its own longitudinal axis but also about the axis 406. This is accomplished in the embodiment shown by coupling the output shaft 405 to axis 406 with a coupling that allows relative rotation of the output shaft 405 around axis 406. It will be appreciated that with this device, the output shaft 405 can be rotated in nearly a full circle around the axis 406 with no variation in the torque provided.

Figure 5:
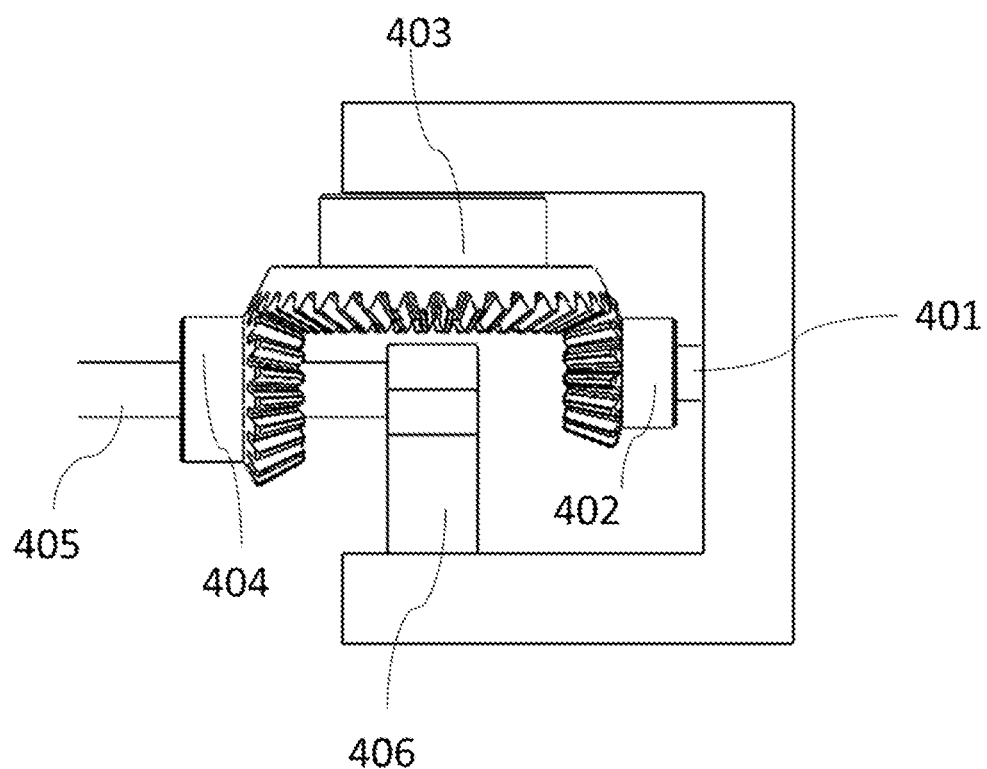
FIG. 5 presents a plan view of an embodiment of the variable coupling of the present invention.

In FIG. 5 the same embodiment is shown in plan view. Torque is transmitted from an external source to input shaft 401 and from there to gearwheel 402. Gearwheel 402 engages crown gear 403, which therefore rotates and applies torque to gearwheel 404. The output shaft 405 is thus caused to rotate. The crux of the invention lies in the extra degree of freedom allowed to the output shaft 405, namely that it may also rotate about the axis of the crown gear 403, this being the key provision of the invention. Axis 406 is preferentially but not necessarily largely collinear with the rotational axis of the planetary gear 403. Since the sizes of the gearwheels 402, 404 may be varied, the coupling as a whole can be made to provide a gear reduction or enlargement, with correspondingly greater or smaller output torque, and correspondingly smaller or greater rate of angular rotation.

It should be noted that due to the symmetry of the device, torque can also be transmitted in the opposite direction, from what we have called the output shaft to what we have called the input shaft. The terms 'output' and 'input' are therefore somewhat misleading since either can be used for output or input. Furthermore it will be appreciated that the change of the axis of rotation of output with respect to input is a relative one, and that therefore the input axis of rotation can be moved instead of the output axis of rotation, or both may be allowed to rotate with respect to a stationary coordinate system. This is more than simply a matter of nomenclature; the effect can be used for instance to transmit feedback. For example, an actuator can be used to move a certain object, and a sensor can be attached to this object such that the degree of movement achieved is transmitted back to the operator of the device. A felicitous coaxial arrangement for such an implementation requiring several simultaneous degrees of freedom is described in the following.

Figure 6:
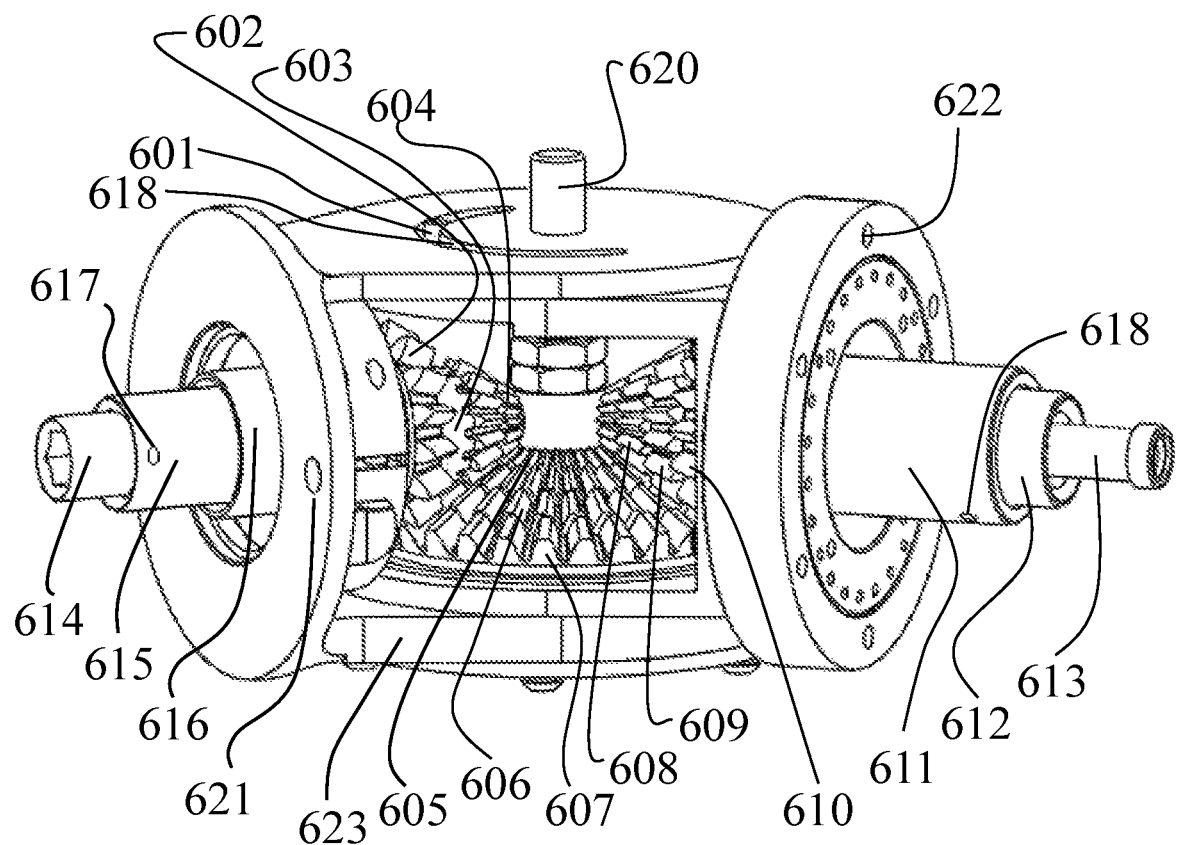
FIG. 6 presents an isometric view of a second embodiment of the variable coupling of the present invention.

It is within the scope of the invention to allow for multiple coaxial input and output shafts to be employed simultaneously. With reference to FIG. 6 an example of such an embodiment is given in isometric view. The input shafts 611,612,613 are all collinear. They may be independent or dependent, as will be determined by the configuration of keyways and shafts such as 617,618 that can couple two input shafts or two output shafts such that they rotate together. The output shafts 614,615,616 are rigidly coupled to output couplings 604,603,602 respectively and therefore rotate with them. These output couplings are caused to rotate by means of crown couplings 605,606,607 respectively. The crown couplings are caused to rotate by means of input couplings 608,609,610 respectively. These input couplings are rigidly attached to input shafts 611,612,613 and therefore rotate with them. The key provision of the invention lies in the 'extra' degree of freedom available to the output shafts 614,615,616 which can rotate along with output couplings 604,603,602 around the axis 620. The axial support pin 601 fits into track 618 and travels with the output shafts, supporting them against axial loading. The radial support pin 621 supports the output shafts against radial loading.

A further provision of the invention is for locking of individual axes. In FIG. 6 one sees that bolts 622 have been introduced which lock the outermost input shaft to the body of the coupling. Therefore any attempt to rotate this input shaft will result in a rotation of the entire coupling. Similar bolts can be added to the output shafts as well, allowing the coupling to be rotated around the axis of the output shaft. Finally, the crown couplings 605,606,607 can also be locked to the base 623 of the device. By so doing, the direction of the output shafts can be changed, as can the disposition (in the sense of angular orientation) of the entire joint itself.

It is within provision of the invention that the aforementioned bolts be replaced with coupling elements such as linear actuators, electromagnets, and the like. It will be obvious to one skilled in the art that such coupling elements can be so constructed that they couple or decouple electronically, allowing a further level of control over the device.

Figure 7:
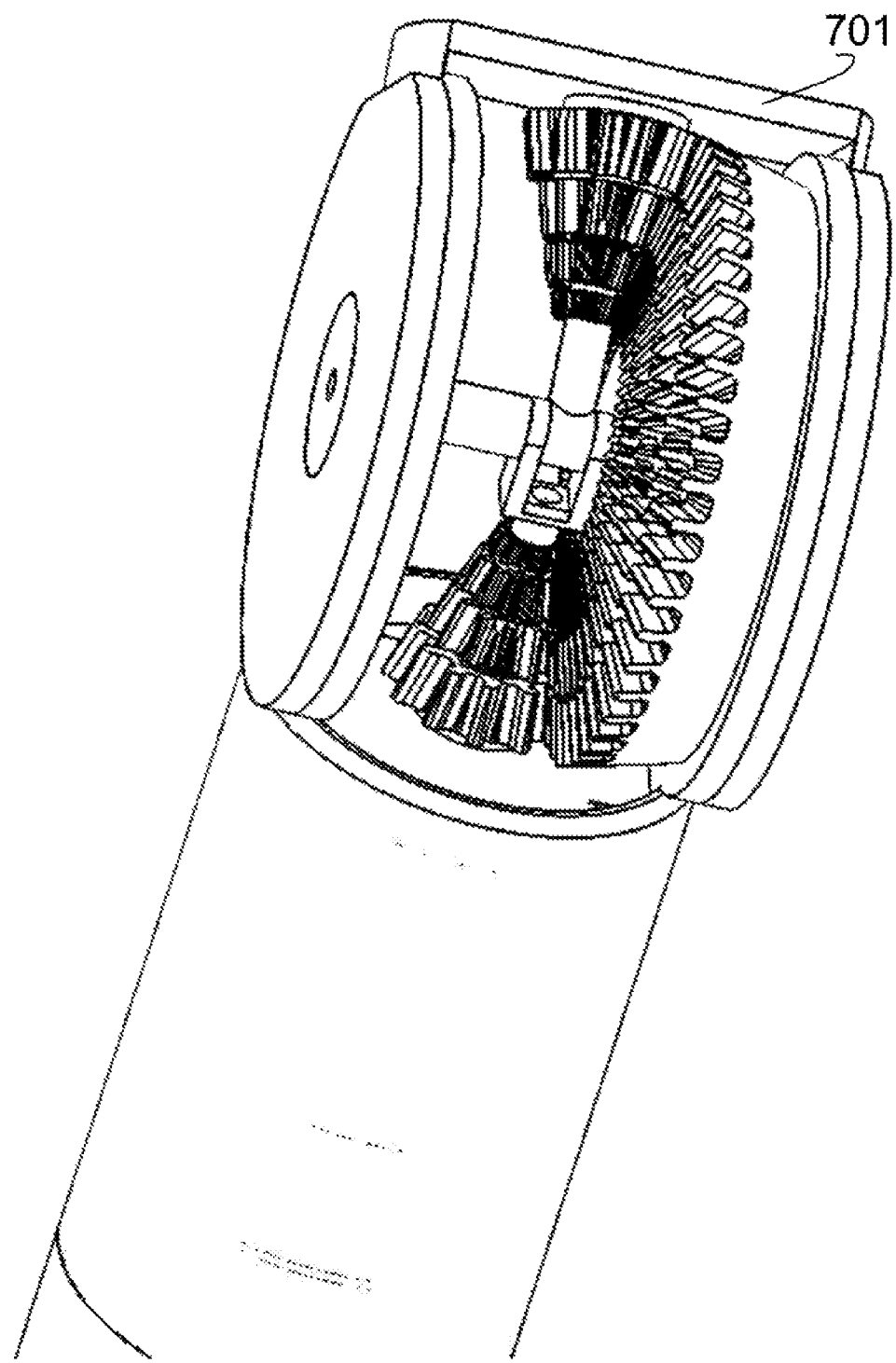
FIG. 7 presents a view of an embodiment of the variable coupling of the present invention.
Figure 8:
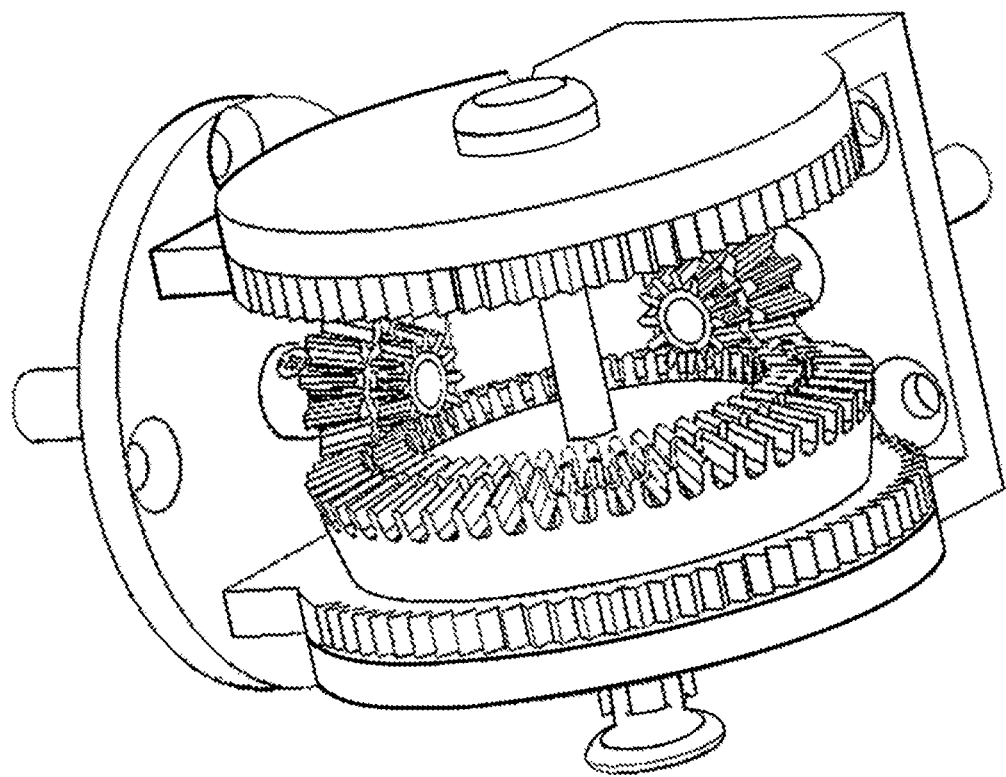
FIG. 8 presents an embodiment of the variable coupling of the present invention where both input and output shafts have been removed.

In FIG. 7 one sees and alternative embodiment of the device with modified mechanical dimensions. In this figure the modularity of the coupling is evident; the output shafts have been removed from the device and can now be replaced by a different output shaft (suitable for a different surgery, for instance). The output shaft (not seen) attaches to the output flange 701. A similar embodiment is shown in FIG. 8, where both input and output shafts have been removed. This would allow (for instance) the coupling as a whole to be cleaned.

Figure 9A:
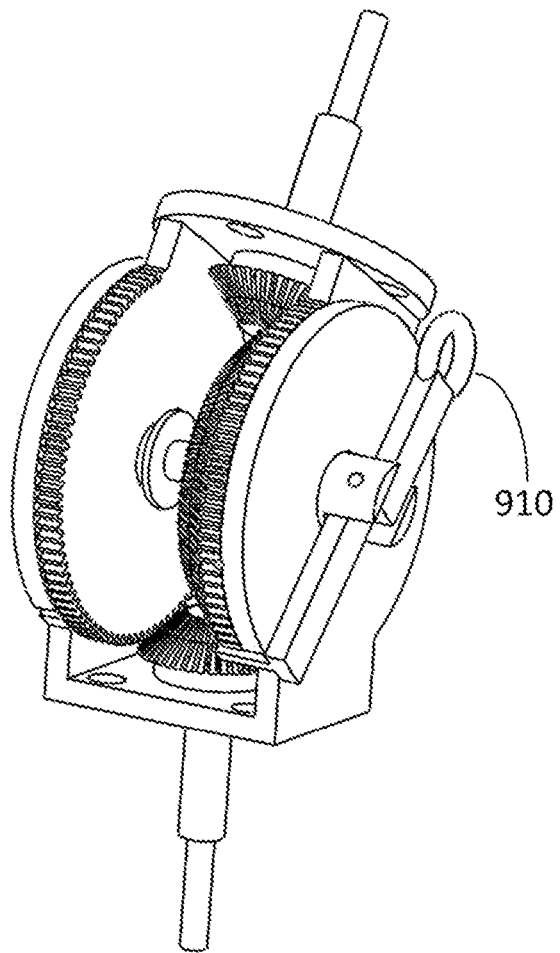
FIGS. 9A-B presents isometric views of an embodiment of the coupling of the instant invention.
Figure 9B:
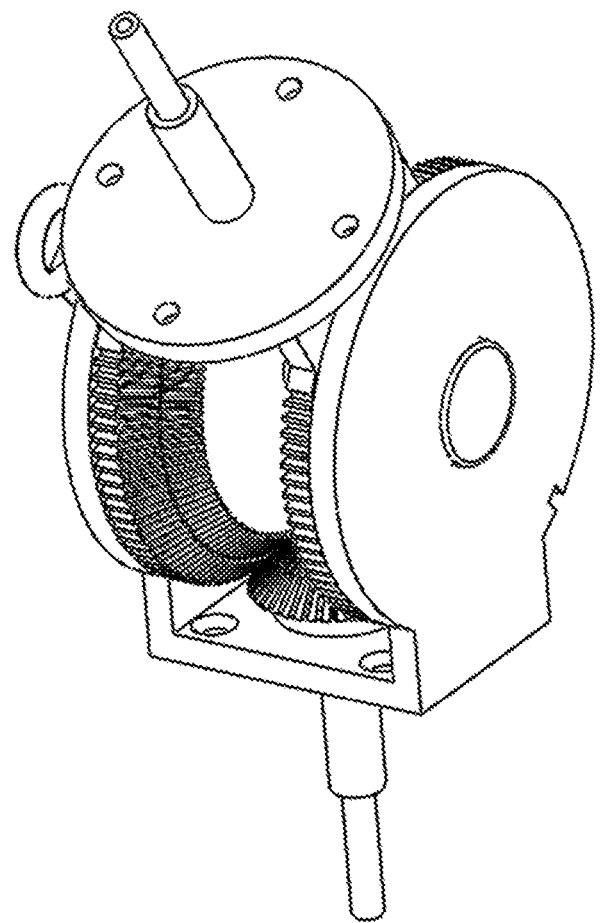

In FIG. 9 A, B isometric views of an embodiment of the joint are shown. A gear lock bar 910 is seen. This gear lock bar serves to lock certain gears of the device in place, in place of the bolt 622 of FIG. 6. The gear lock bar allows (for example) a surgeon to lock the output shaft into a desired direction.

Figure 10:
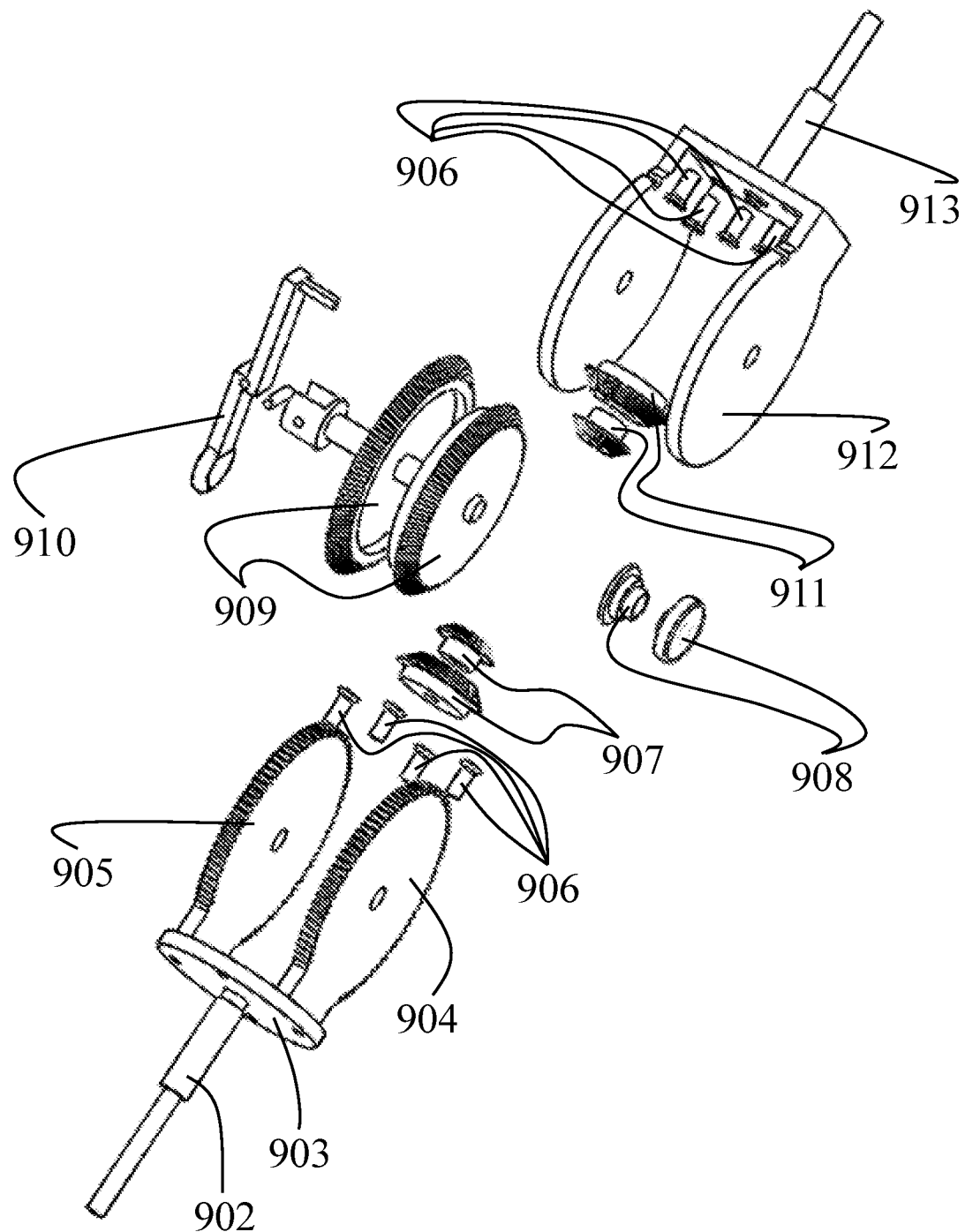
FIG. 10 presents an exploded view of the coupling of the current invention.

In FIG. 10 an exploded view of the joint of a joint of the device of the current invention is shown. Input concentric cylinders 902 attach to the input flange 903. This flange is rigidly coupled to coupling orientation gears 904, 905. Bolts 906 can be used to couple the flange to a rigid surface. The input bevel gears 907 communicate torque to the crown gears 909, which in turn communicate this torque to the output bevel gears 911. These output bevel gears 911 are in communication with the output concentric cylinders 913. Bearing/stay 908 keep the crown gears 909 in place. The gear lock 910 allows the angle of the output shaft with respect to the input shaft to be locked. It should be emphasized that the input and output shafts 902, 913 can be detached from their respective flanges (902,912) if necessary, allowing different sections of the device to be removed or replaced.

Figure 11A:
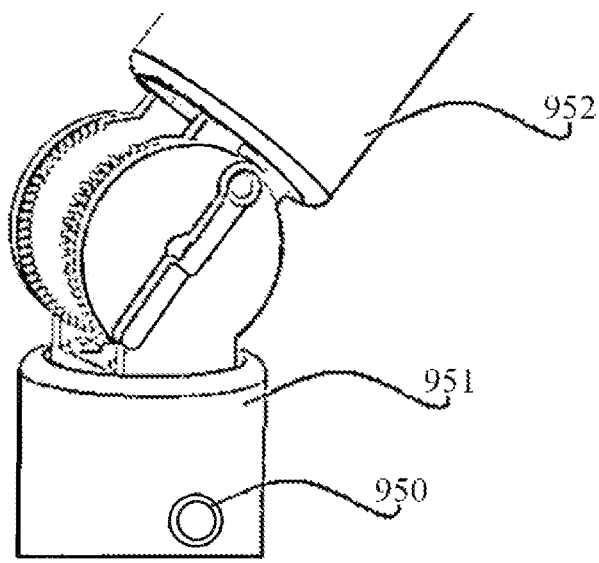
FIGS. 11A-B presents a gear lock release for the coupling of the current invention.
Figure 11B:
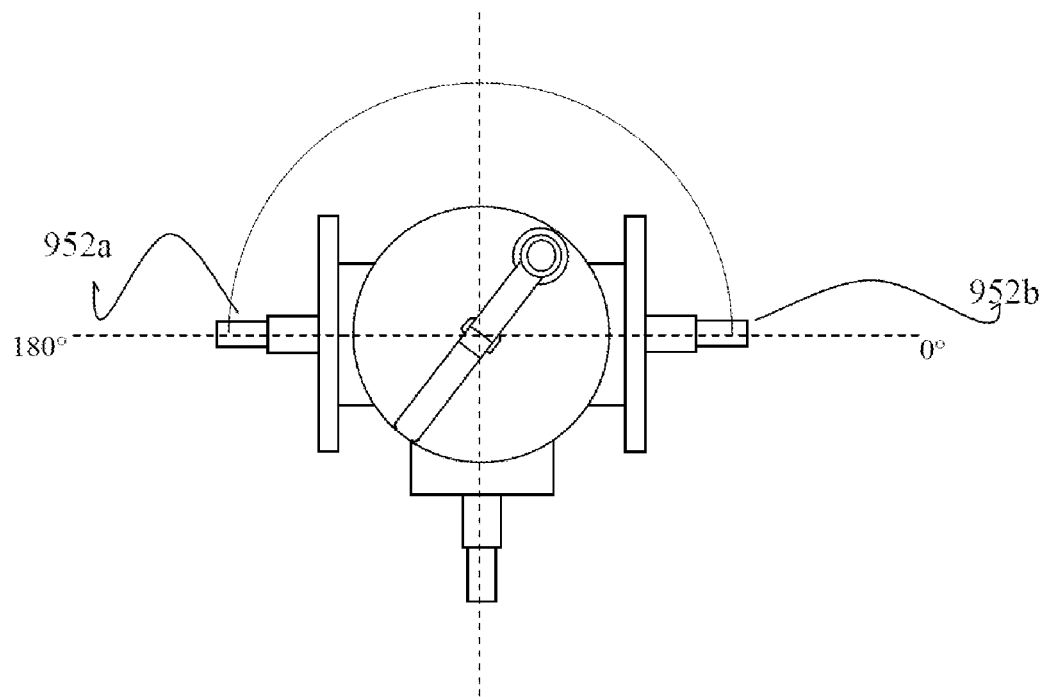
Figure 12A:
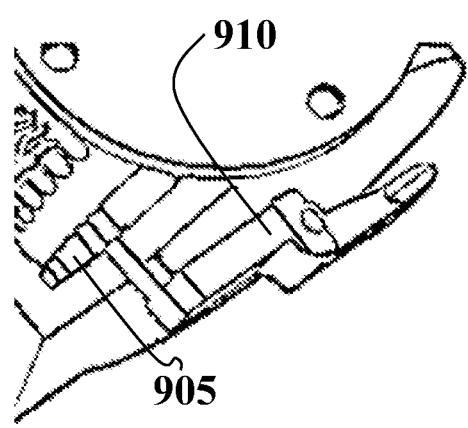
FIGS. 12A-D presents views of an embodiment of a shaft lock.
Figure 12B:
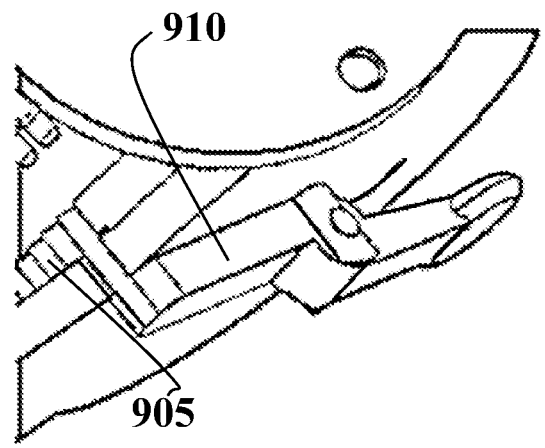
Figure 12C:
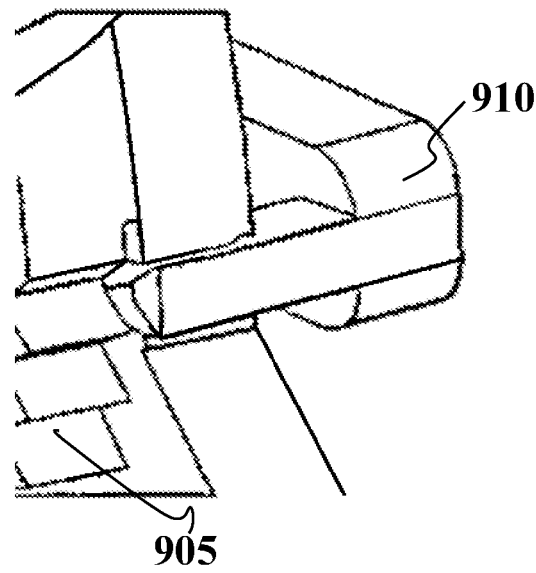
Figure 12D:
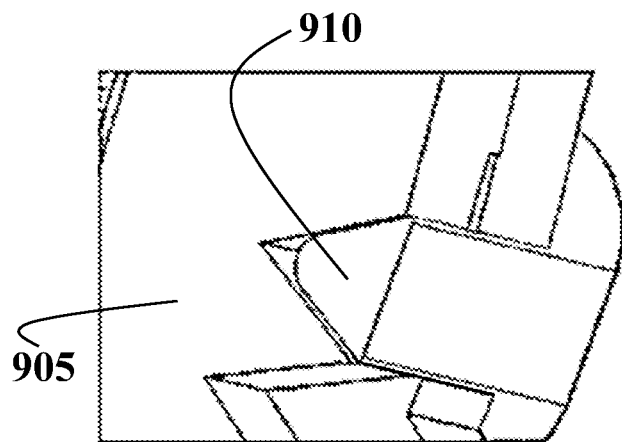

In FIG. 11A the gear lock release is seen; a button 950 is depressed to release the gear lock and allow the output shaft 952 to be rotated with respect to the input shaft 951. In FIG. 11B another view is given allowing one to note the large angular range of the output shaft, moving from position 952a to position 952b.

In FIG. 12A-D the shaft lock is shown in greater detail. The shaft lock 910 can either allow or disallow free rotation of the shaft gear 905, thereby allowing or disallowing repositioning of output axis with respect to the input axis.

Figure 13:
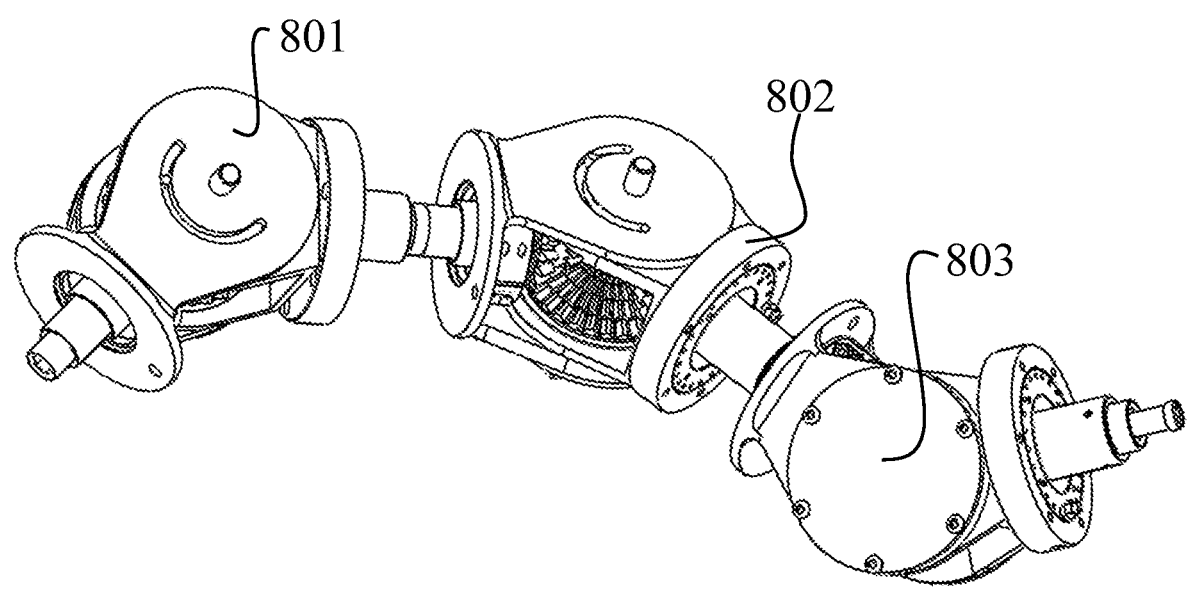
FIG. 13 presents three of the variable couplings of the present invention in series.

It will be noted by the astute observer that the output axis of rotation of the instant invention can rotate in a single plane only if one does not use the aforementioned provision of bolts or output shaft lock(s) to allow for rotation of the coupling mechanism itself. However as will be clear to one versed in the art, this restriction can be removed by the simple expedient of providing one or more further identical joints of the instant invention in series with the first, as shown in FIG. 13, where three joints 801,802,803 have been coupled in series. An embodiment with two or more joints in series provides a nearly full range of motion of the output shaft, in all directions relative to the input shaft. The only restriction on the angles is that the various shafts cannot physically overlap any other shaft, thus eliminating certain configurations from the realm of possibility. It will be appreciated however that the disallowed positions form a small proportion of the total universe of possibilities. This is especially relevant when considering that the possible input-output angles of e.g. single or double Cardan joints are restricted to small angles of around 168 degrees or less.

It will be appreciated that the gear ratio between input and output shafts can be varied by variation of the size of the wheels or gearwheels of the couplings. In particular, if the input and output gearwheels have radii ri, $r_3$ then the total gear ratio will be $ri/r_3$.

The constant velocity joint of the instant invention comprises:
  i. An input shaft adapted to be rotated around an input axis of rotation (the longitudinal axis of the shaft) by a sources of torque.
  ii. An input transmission means, coupled to one of said input shaft, said input transmission means defining a first plane substantially perpendicular to said input axis of rotation. The input transmission means may for instance be a spur gear.
  iii. A second transmission means rotatably connected to said input transmission means; said second transmission means defining a second plane, such that said second plane is substantially perpendicular to said first plane. The second transmission means may comprise for instance a crown gear meshing with the first spur gear.
  iv. An output transmission means rotatably connected to said second transmission means; said output transmission means defining a third plane; said third plane being substantially perpendicular to said second plane. The output transmission means may comprise for instance a spur gear meshing with the second transmission crown gear.
  v. An output shaft, coupled to said output transmission means, adapted to rotate around an output axis of rotation, said axis of rotation being free itself to rotate.

It will be noted that the angle between said first input axis of rotation and said final output axis of rotation may vary in an angular range of about 0 to about 360 degrees.

The transmission means may be selected from a group consisting of gearwheels, wheels, crown gears, bevel gears, or other means for transmitting rotational motion, or combinations thereof.

In one embodiment of the invention an axial support member (601) is provided, to provide axial support to the output shafts. Also a circular track (618) centered on the axis of rotation of said second transmission means is provided, said axial support member being adapted to fit into said track and slide within it.

In one embodiment of the invention a radial support member (604) is further provided to provide radial support to the output shaft, said radial support member being adapted to rotate in said second plane.

In one embodiment of the invention several coaxial input shafts are coupled individually to several coaxial output shafts, allowing independent transmission of torque from input to output on several shafts simultaneously.

It should be appreciated that the output shafts may be coupled to a wide variety of devices, such as graspers, cutters, splicers, welders, force-feedback devices, robotic hands, and the like. In particular the use of force-feedback devices to provide a 'return signal' by means of one or more shafts will be found especially useful in microsurgery, robotics, and the like wherein it is desirable to have some feedback concerning the 'feel' of the work being done.

It should be pointed out that amongst other advantages of the instant invention is the fact that the torque-providing elements that turn the input shafts may be located rather distant from the location where the torque is applied. This is especially important in such fields as arthroscopy, microsurgery, and robotics, wherein it is generally desirable that the point at which delicate operations occur are as compact as possible. Also the presence of motors on or near joints can cause unwanted extra weight, moments of inertia, and the like. The instant invention allows many sources of torque to be transmitted in parallel in a minimum of space limited only by the shaft wall thicknesses, and at a distance from the actual operations of the output shafts that is in principle unlimited. No motors are required at the location of the joint itself, as in many current applications.

It should be further appreciated that the instant invention allows for the actuating motors to be located in a central protected location such as the abdomen of a robot, the center portion of a tank, etc. This further allows for a single motor to activate several input shafts independently. If for example it is discovered that in a particular application certain actions requiring rotation of shaft A preclude other actions requiring rotation of shaft B, a single motor can be used to provide the torque necessary for these actions, and switched from input shaft A to input shaft B by a suitable gearbox as will be obvious to one skilled in the art.

In one embodiment of the invention access is given to the crown gears of the device, in effect changing the device into a three-terminal or 'T' or 'Y' device. In particular the central or crown gears 605, 606, 607 (FIG. 6) may be connected to input/output shafts of their own. Now more complex operations may be allowed, wherein further couplings are connected to this center shaft, or further torque sources, or further output devices such as graspers, cutters, and the like, or sensors.

We now turn to the incorporation of this coupling device into a laparoscopic instrument of improved design. In the prior art one finds a large number of laparoscopic positioning systems such as those shown in FIGS. 14A-14C. These will in general allow a small number of degrees of freedom, the maximum found in a search of the patent literature being five degrees of freedom.

Figure 15A:
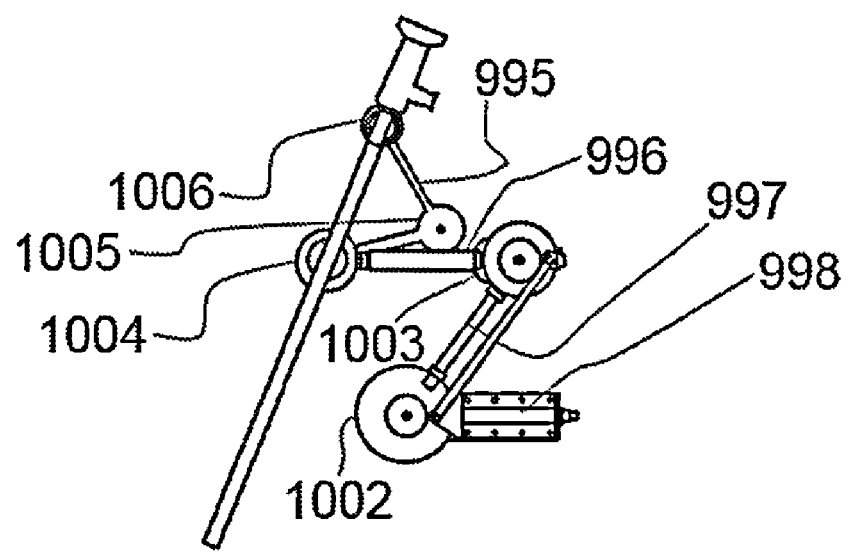
FIGS. 15A-B presents a laparoscopic instrument based on the coupling of the current invention.
Figure 15B:
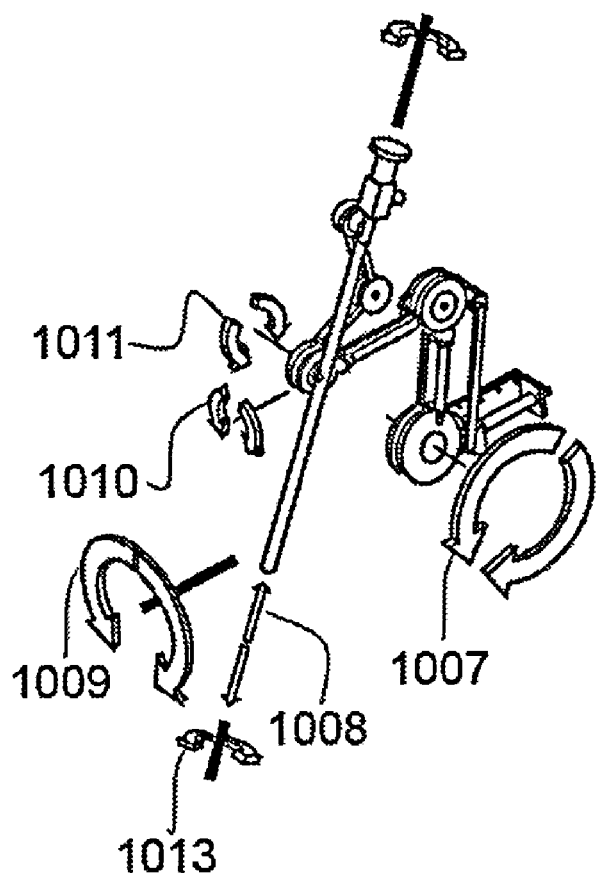

To improve upon this situation while keeping the simple tubular design of the laparoscope intact, we incorporate the aforementioned coupling device into an endoscope/laparoscope maneuvering system as shown in FIG. 15A, B.

The cylindrical members (consecutive arm sections) 995, 996, 997 and 998 contain a plurality of concentric cylinders, each able to rotate independently and thereby activate an independent degree of freedom. By means of these concentric cylindrical members, the couplings (i.e., the constant velocity couplers) 1002, 1003, 1004, 1005 and 1006 serve to rotate/translate the device (namely the endoscope/laparoscope 1001b or the camera 1001a) in the directions $DOF_1$ (1007), $DOF_2$ (1008), $DOF_3$ (1009), $DOF_4$ (1010), $DOF_5$ (1011), DOF6 (1012) and $DOF_7$ (1013), in which $DOF_1$ represents the ability of the system to move the endoscope or laparoscope forward and backwards in direction represented by numerical reference 1007, DOF2 represents the ability of the system to move the endoscope or laparoscope in a zoom movement i.e. in and out of the patient body through the penetration point (represented by numerical reference 1008), DOF3 represents the ability of the system to move the endoscope or laparoscope to the right and left in direction represented by numerical reference 1009, DOF4 represents the ability of the system to fine tune the endoscope or laparoscope movements to the right and to the left in direction represented by numerical reference 1010, DOF5 represents the ability of the system to fine tune the endoscope or laparoscope movements forward and backwards in direction represented by numerical reference 1011, $DOF_6$ represents the ability of the system to rotate the camera 1001b with respect to the endoscope's 1001a long axis. This degree of freedom is necessary to keep the horizon of the image when using endoscope with "angled edge," and $DOF_7$ represents the ability of the robot to rotate the endoscope 1001b about its long axis.

Figure 16A:
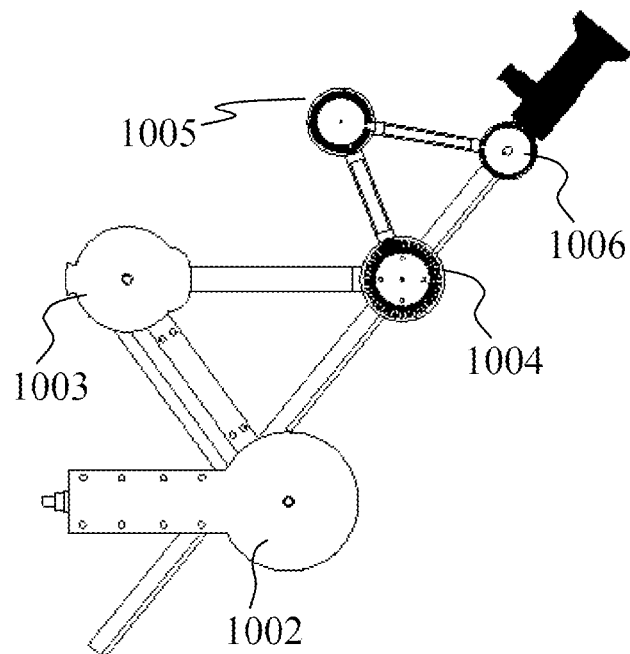
FIGS. 16A-B presents a laparoscopic instrument based on the coupling of the current invention.
Figure 16B:
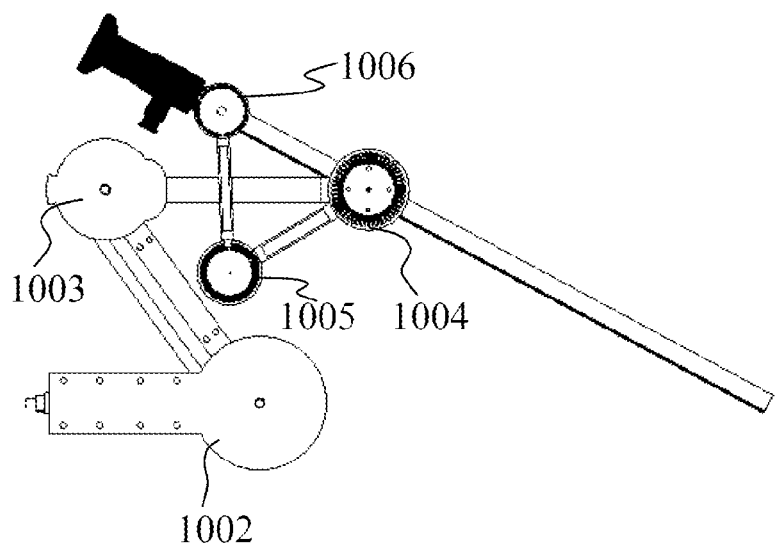
Figure 17A:
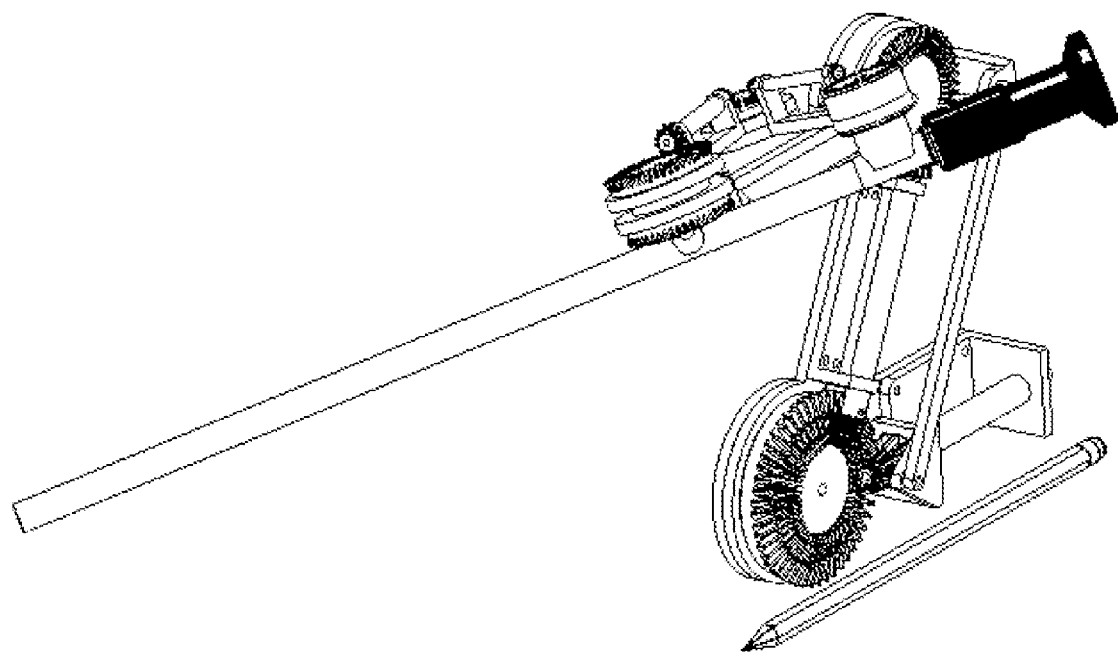
FIGS. 17A-B and 18A-B present a laparoscopic instrument based on the coupling of the current invention.
Figure 17B:
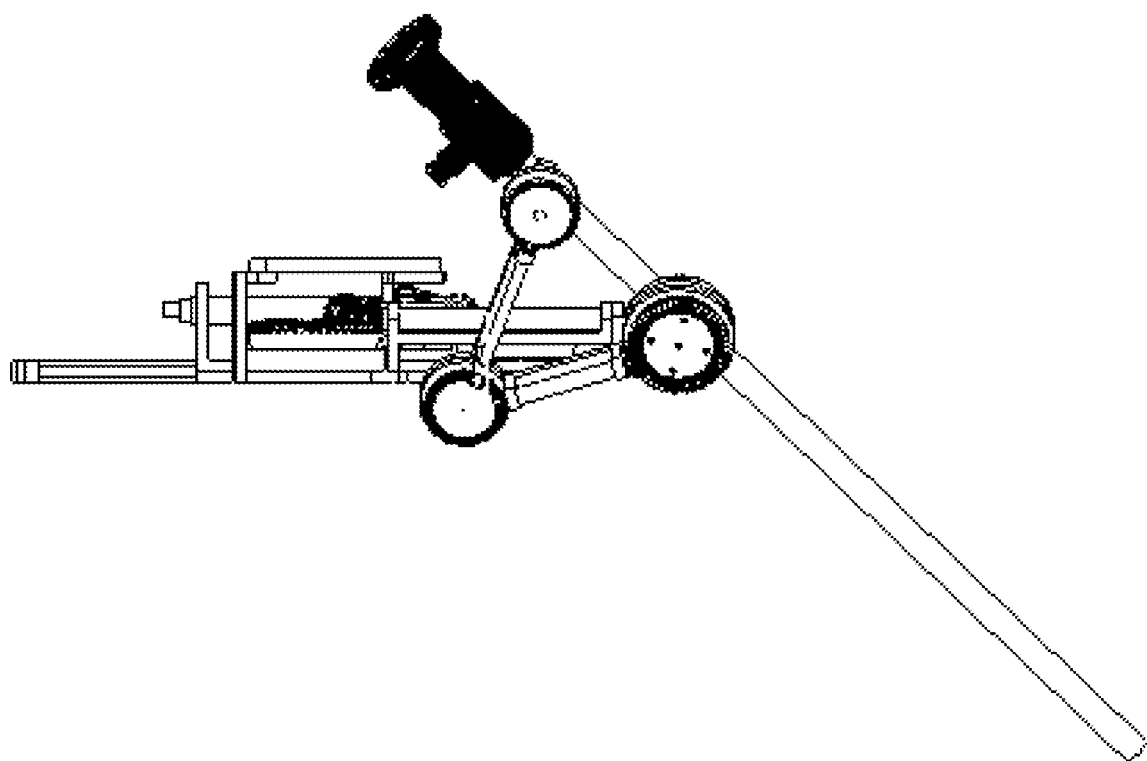
Figure 18A:
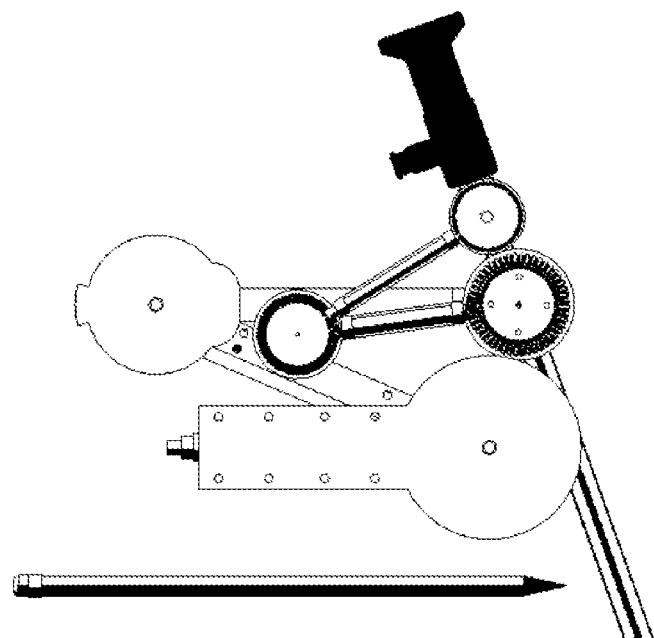
Figure 18B:
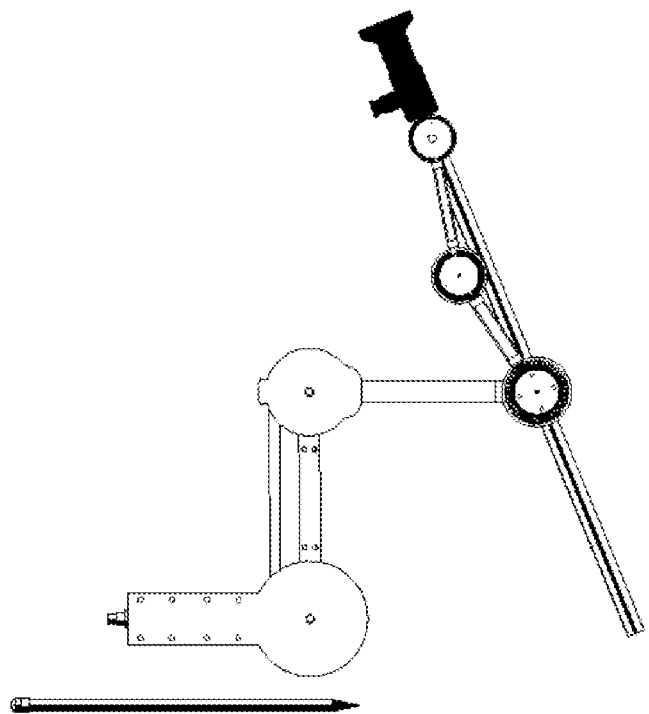

Views of the same device from the opposite direction are shown in FIGS. 16A,B. Isometric views are shown in FIGS. 17A,B. Further side views are shown in FIG. 18A,B with a pencil included for scale.

Figure 19:
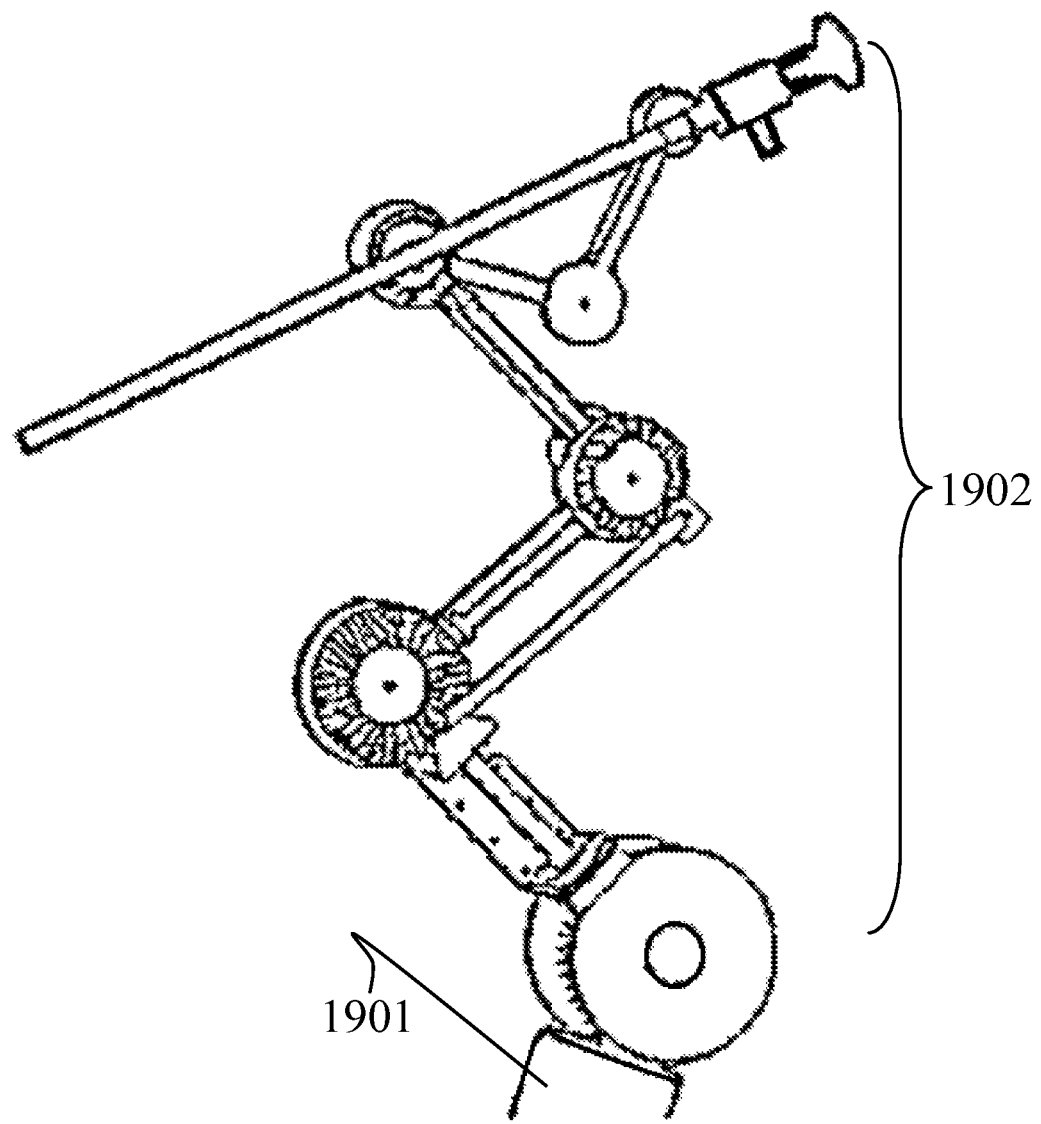
FIG. 19 shows a preferred embodiment of the present invention which incorporates the positioning elements of FIGS. 15A-18B.

FIG. 19 shows the main and the preferred embodiment of the present invention which incorporates the positioning elements of FIGS. 15-18 upon a standardized tubular arm 1901. As described above, the core concept of the present invention lies in the fact that the positioning section 1902 may be removed entirely from the fixed section (tubular arm) 1901 e.g. for replacement, repair, cleaning, etc.

Figure 20:
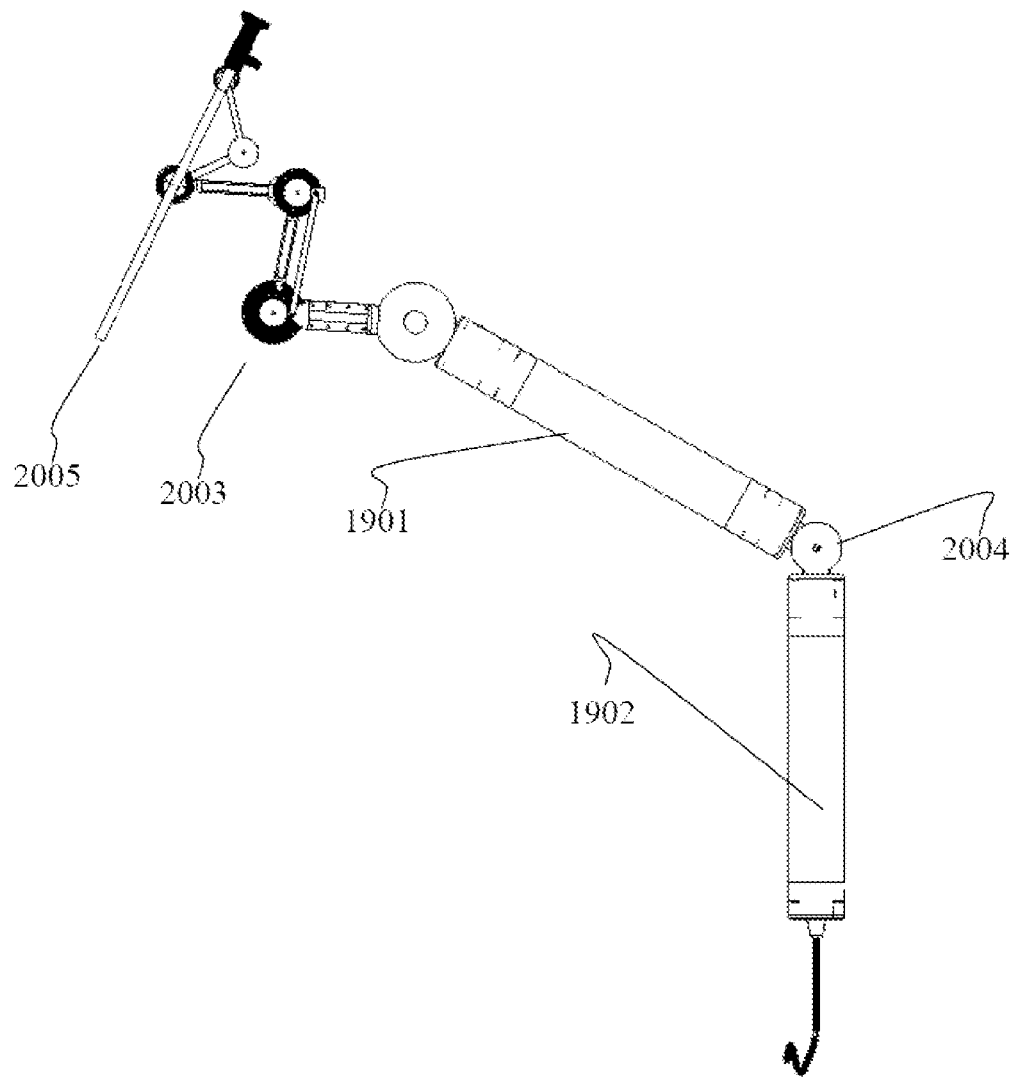
FIG. 20 illustrates a second embodiment of the present invention in which two consecutive tubular members are employed.

In FIG. 20 illustrates a more complete embodiment, where two consecutive tubular members 1901, 1902 are employed. The lower tubular member 1902 may for instance be fixed to the floor, ceiling, surgical table, or the like. This tubular member is in certain embodiments endowed with one or more cylindrical motors (which will be further explained in FIG. 22) within the body of the cylinder, adapted to turn a set of the concentric torque-transmitting elements described above.

The second tubular member 1901 transmits these torques to the medical tool to which he is coupled. It is within provision of the invention that one of these multiple torques can be used to rotate the upper tubular member 1901 about the coupling element 2004. It is also within provision of the invention that these two arms may be detached from one another. The upper tubular member 1901 may also be provided with one or more internal cylindrical members such as shafts or motors to power the various operations of the laparoscope, including the various possible movements of the laparoscope positioning section 2003, and any surgical instruments attached to the end of the laparoscope tube 2005.

Figure 21:
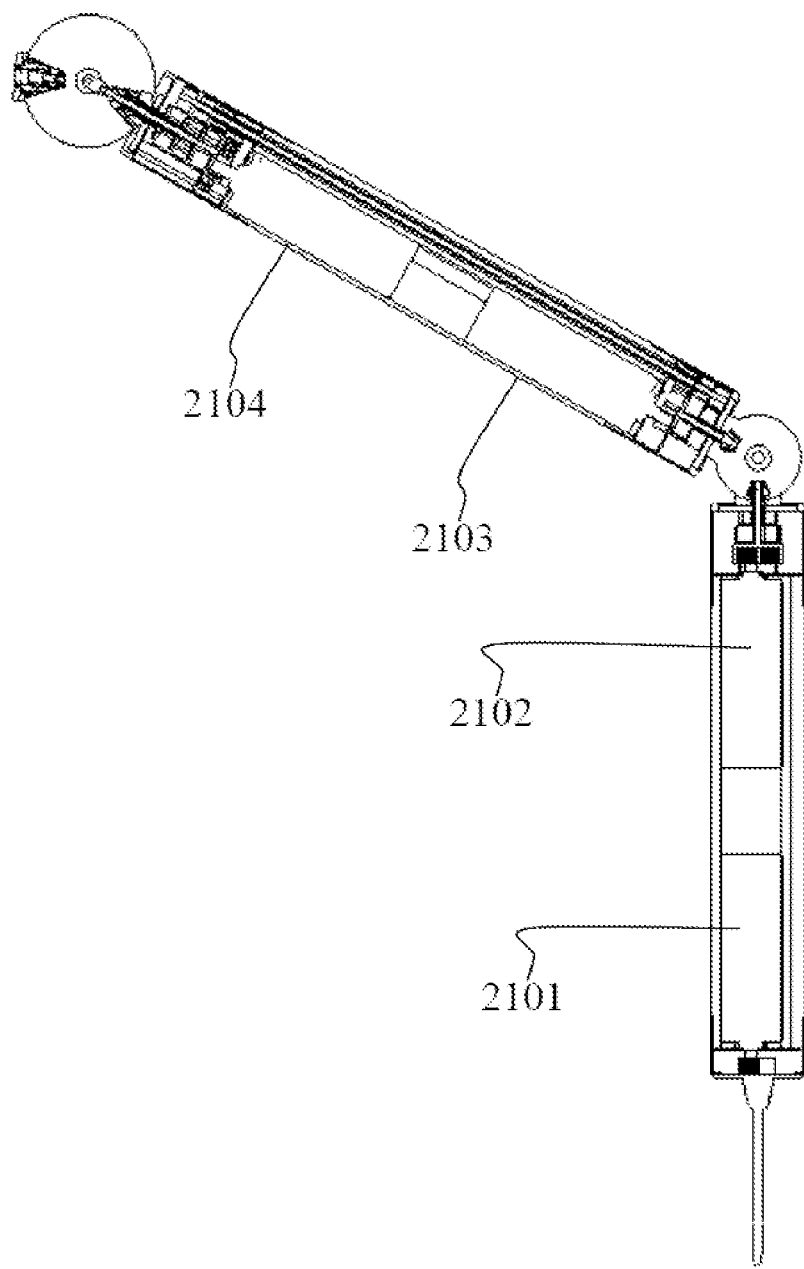
FIG. 21 shows a cross section of the tubular sections shown in FIG. 20.

It is emphasized that the number of the consecutive tubular members is not limited to two. In FIG. 21 a cross section of the tubular sections shown in FIG. 20 is shown. In the cross section of FIG. 21 one can see the two motors 2101, 2102 of the lower arm and the two motors 2103, 2104 of the upper arm. Each of the motors is adapted to provide movement in a specific direction. For example, motor 2104 may be adapted to provide left and right movement; motor 2103 may be adapted to provide forward and backwards movement; motor 2102 may be adapted to provide zoom in and zoom out movements; and, motor 2101 may be adapted to provide rotational movements.

Figure 22A:
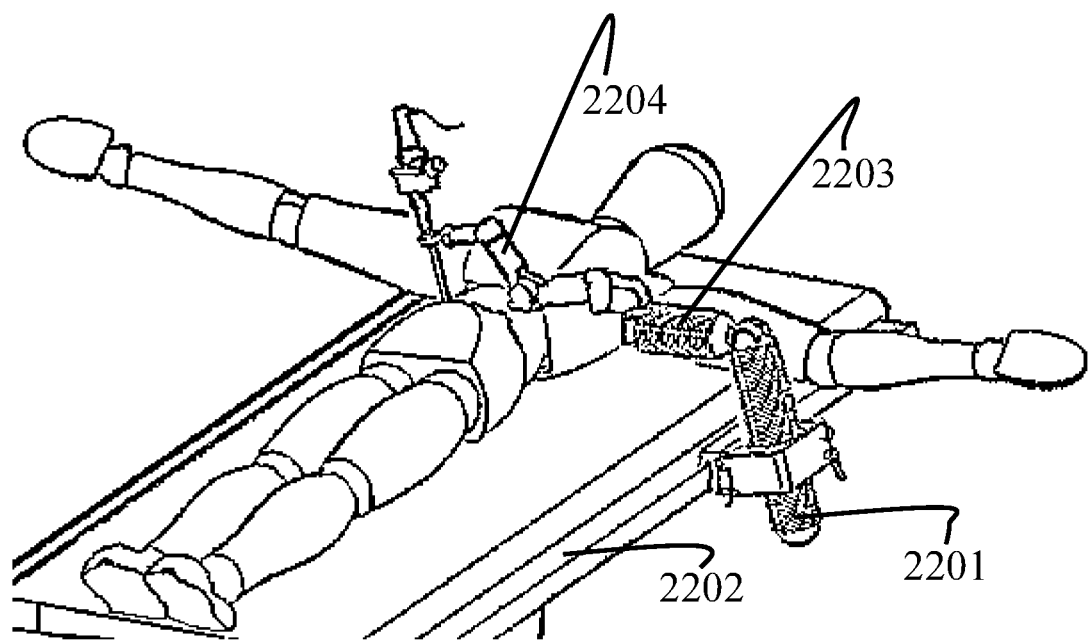
FIGS. 22A-C illustrates an embodiment of the device in use.
Figure 22B:
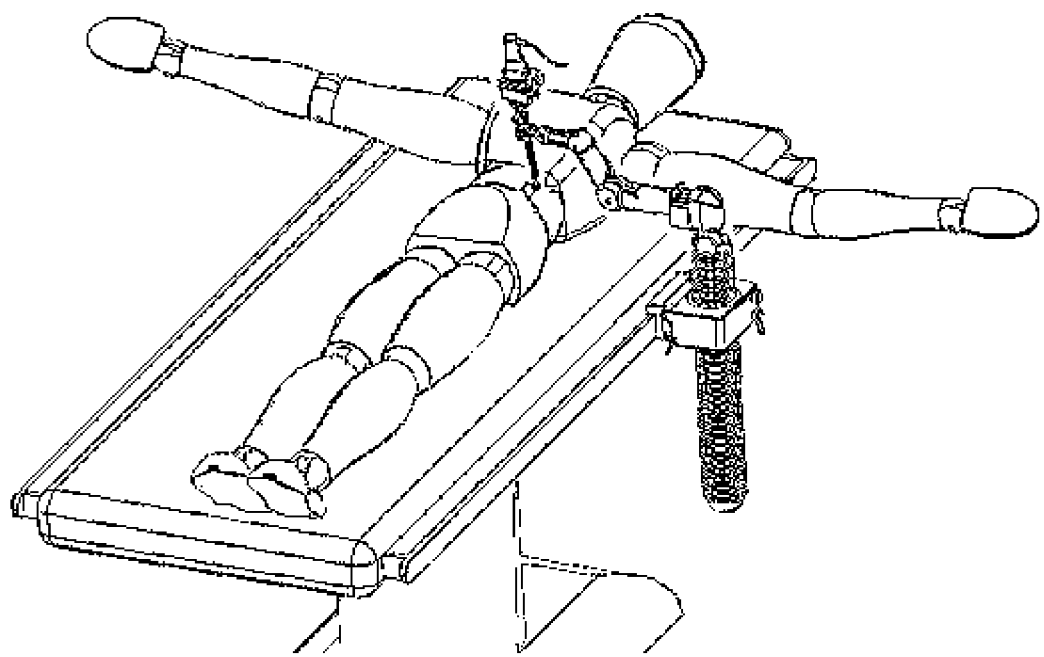
Figure 22C:
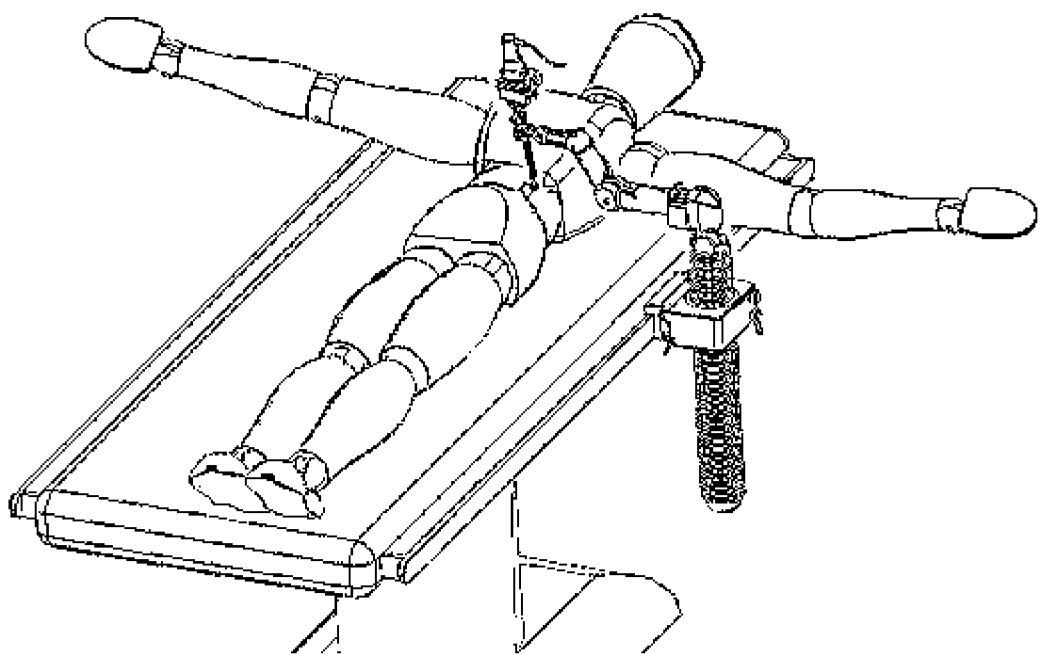

In FIG. 22 an embodiment of the device is shown in use. The lower arm 2201 is shown fixed to the operating table 2202. The upper arm 2203 may rotate about the coupler between the upper and lower arms, while the seven degrees of freedom of the laparoscope positioning section 2204 allow the laparoscope 2205 to be moved controllably in many ways, as may be required during surgical procedures.

Figure 23A:
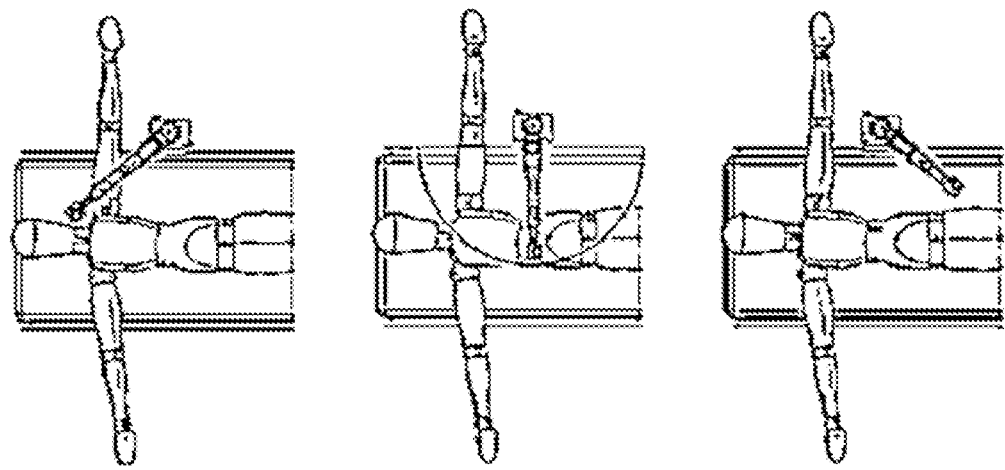
FIGS. 23A-C illustrates various possible motions of the device.
Figure 23B:
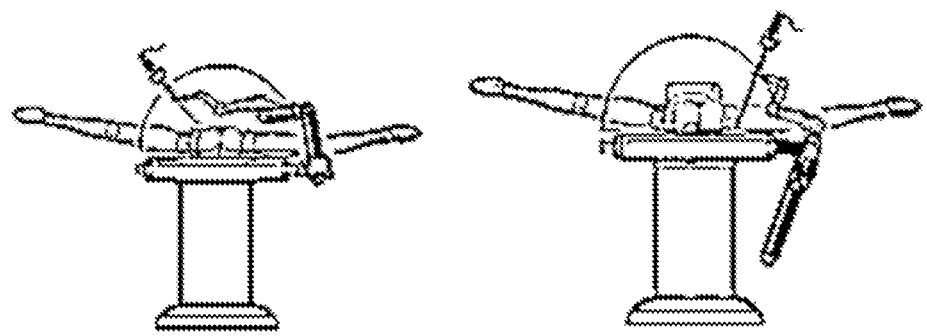
Figure 23C:
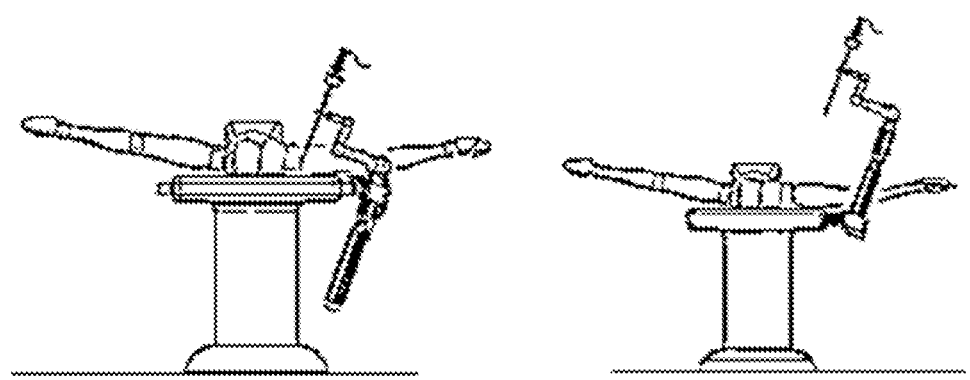

In actual use such a laparoscope as described above may be operated either manually by a human being, or robotically, according to a programmed set of instructions, by a robotic mechanism obeying human commands, remotely, or the like. A robotic mechanism is shown in FIG. 23A,B, In FIG. 23A,B, various possible motions of the device are illustrated.

Figure 24A:
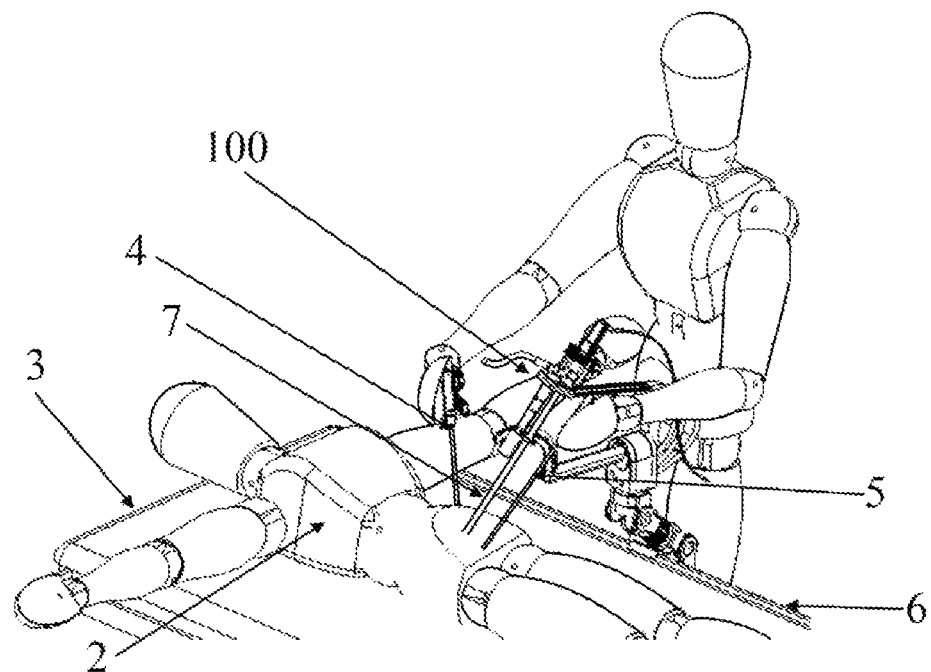
FIGS. 24A-B illustrates various possibilities for operation of the device.
Figure 24B:
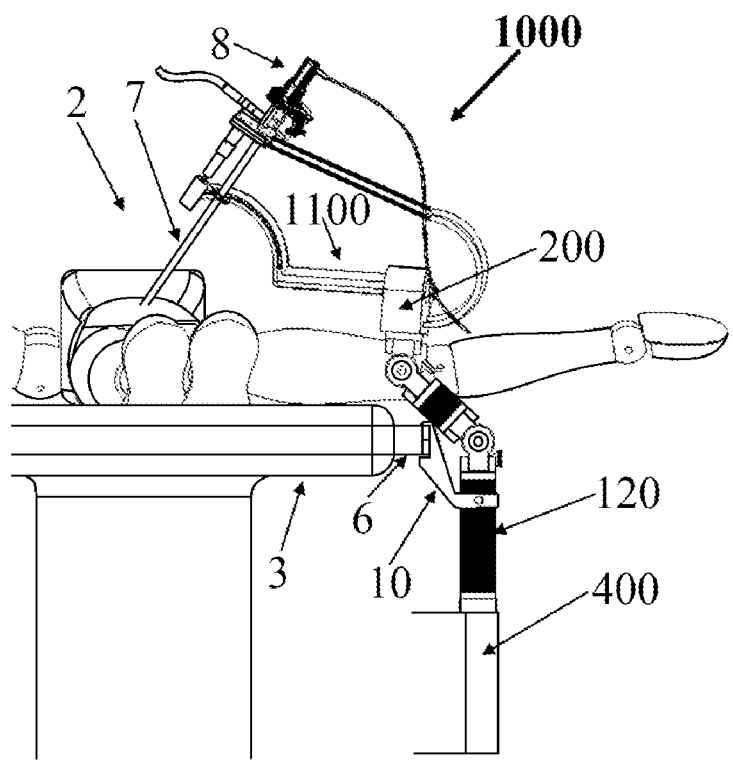

In FIGS. 24A and 24B various possibilities for operation of the device are shown. In FIG. 24A a surgeon is shown operating using the device. As will be obvious to one skilled in the art the actuation may be carried out using a variety of means such as joystick control, keyboard control, voice control, manual control, power-assisted control, or the like. In FIG. 24B the device is shown without a surgeon, who may in principle control the movements of the device remotely, or in principle the device may be operated entirely algorithmically.

It is within the scope of the invention that the base and body units of the invention provide various desirable elements to allow complex surgical procedures to be carried out, such as one or more fluid channels, one or more electrical conductors, one or more fiber optic channels, and the like. The fluid channels may provide e.g. CO2 for inflating a body cavity, saline solution for flushing, vacuum for aspirating blood, pus, or other bodily fluids, and the like. The electrical conductors may conduct voltages to operate various motors or actuators, conduct information from sensors such as video cameras or piezoelectric gauges, and the like. The fiber optic channels may conduct visual information from the body or may provide light within the body cavity. It is within provision of the invention that these various elements be conducted in tubes threaded within the tubular structures of the current invention, or attached to the outsides thereof.

One skilled in the art will realize that the device described above has the potential to facilitate surgery by freeing one hand of the surgeon that would otherwise have to grip the laparoscope.

It is further within the scope of the present invention to provide a two-part robotic laparoscopic device useful for functional endoscopic sinus surgery (FESS). If the nasal sinuses become blocked for example by nasal polyps, growths, allergies or infection, causing great discomfort. The first line of treatment for sinus blockages is medical therapy, however in some cases this is unsuccessful and surgery is required. Sinus blockages are a common problem and sinus surgery is one of the most frequently performed, failure to treat sinus blockages can result in facial pain, headaches and rarely, complications. Reference is now made to FIGS. 36 A-C, 37 and 41, illustrating several embodiments of sinus surgery. FESS, allows the procedure to be performed as day operation, accessing the sinuses by inserting an endoscope through the nose and removing blockages in a relatively non-invasive manner, resulting in easier and quicker recovery and lower risks than traditional sinus surgery. Thus FESS is a precise, minimally invasive way to open your sinuses and treat chronic sinus infections. The present invention is provided to enable access of all areas of the sinus and naval cavity with the endoscope, ensuring better treatment of the blockages.

As described above, according to another embodiment of the present invention to improve upon the interface between surgeon and automated assistants by communicating the surgeon's current instrument of choice, supplying location data to the image processing computing software thereby directing the endoscope to focus on said choice. The technology relies on marrying a conventional laparoscopic system with data obtained from small RF transmitters attached to a surgical tool.

The present invention provides an interface between a surgeon and an automated assistant, comprising (a) at least one array comprising N RF transmitters, where N is a positive integer; (b) one RF receiver, said receiver provided with at least one directional antenna; (c) means for attaching said RF transmitter array to at least one surgical tool; and, (d) a computerized operating system adapted to record the relative signal strength received by said RF receiver and to calculate therefrom the position of each of said N RF transmitters, and further adapted to provide automatically the results of said calculation to the human operator of said interface. It is within the essence of the invention wherein said computerized operating system calculates at least one of the parameters chosen from the group consisting of (a) the spatial location of said at least one surgical tool; (b) the path of said at least one surgical tool; (c) the spatial location of the point of insertion of said at least one surgical tool into the body of a patient; (d) the spatial location of the tip of said at least one surgical tool; (e) matching each RF transmitter code with each calculated spatial location of said at least one surgical tool and/or said tip of said at least one surgical tool, and further wherein said computerized operating system provides automatically the results of said calculation to the human operator of said interface.

In one of the preferred embodiments of the invention, any desired surgical instrument is fitted with an RF transmitter, and selection is achieved by depressing its button.

The invention discloses two methods of operation: a manual method, in which a transmitter emits an RF signal only when the surgeon presses a button located e.g., on one of the arms (either left or right—but not both simultaneously), the system then indicating the direction of that arm, and an automatic method, in which all transmitters continuously emit RF signals and the system tracks the direction of all transmitters simultaneously. When the surgeon presses a button of one of the transmitters, the system output is the direction and location of the specific transmitter.

The automatic mode has some advantages over the manual mode because the system can make use of history track files in order to filter the data and apply prediction algorithms. The continuous stream of data also allows the software to compute additional important data such as the insertion point of each tool, and the predicted tools location on the image.

System operation will be explained for both MANUAL (sequential), and AUTOMATIC (periodic or simultaneous) modes. In order to simplify the explanation a system used to locate the positions and directions of only 2 surgical tools is described, but the method described can be used with minor changes to locate the position of any number of surgical tools used in any laparoscopic surgeries.

Figure 25A:
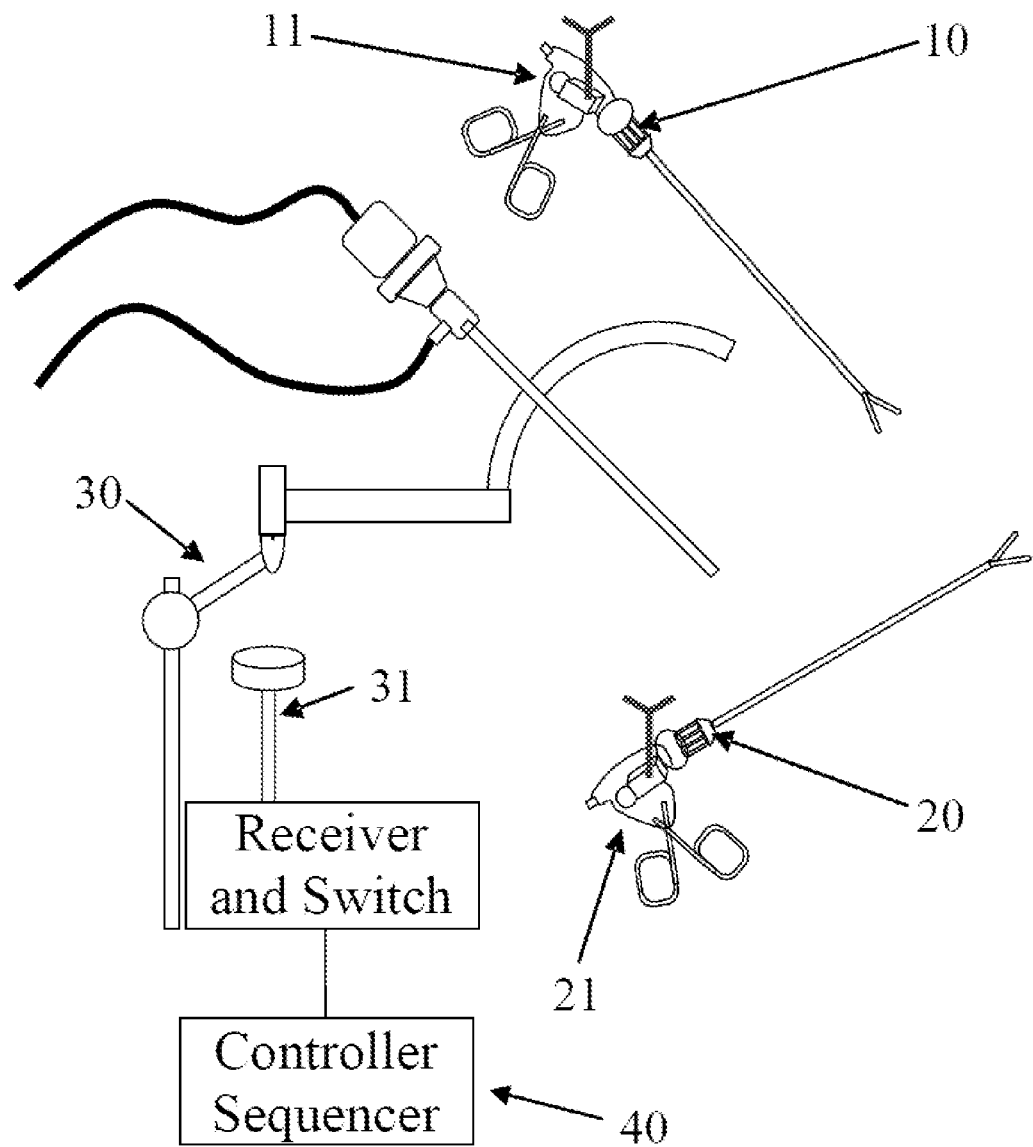
FIGS. 25A-B illustrates a general schematic views, with FIG. 25A schematically illustrating a surgical tool positioning system that detects the location of a surgical tool at the time the surgeon activates the surgical tool transmitter (manual mode) and FIG. 25B schematically illustrating a surgical tool positioning system that detects the location of surgical tools continuously (continuous automatic mode)

Reference is now made to FIG. 25A which schematically describes the surgical tool positioning MANUAL system according to one embodiment of the invention. An antenna 31 is set and a receiver is preferably mounted on, or near, the robotic camera holder. Two identical transmitters, i.e., (i) transmitter 11 mounted on surgical tool 10; and (ii), transmitter 21 mounted on surgical tool 20 are provided. A control and processing function controller 40 is further provided, being either a laptop PC or an embedded controller.

As described above, in the MANUAL system the transmitter emits RF signal only when the surgeon presses upon the surgical instrument the surgeon desires to track. Once the transmitter transmits a signal, the receiver communicates with the controller and instructs the tracking of the medical instrument desired by the surgeon.

Figure 25B:
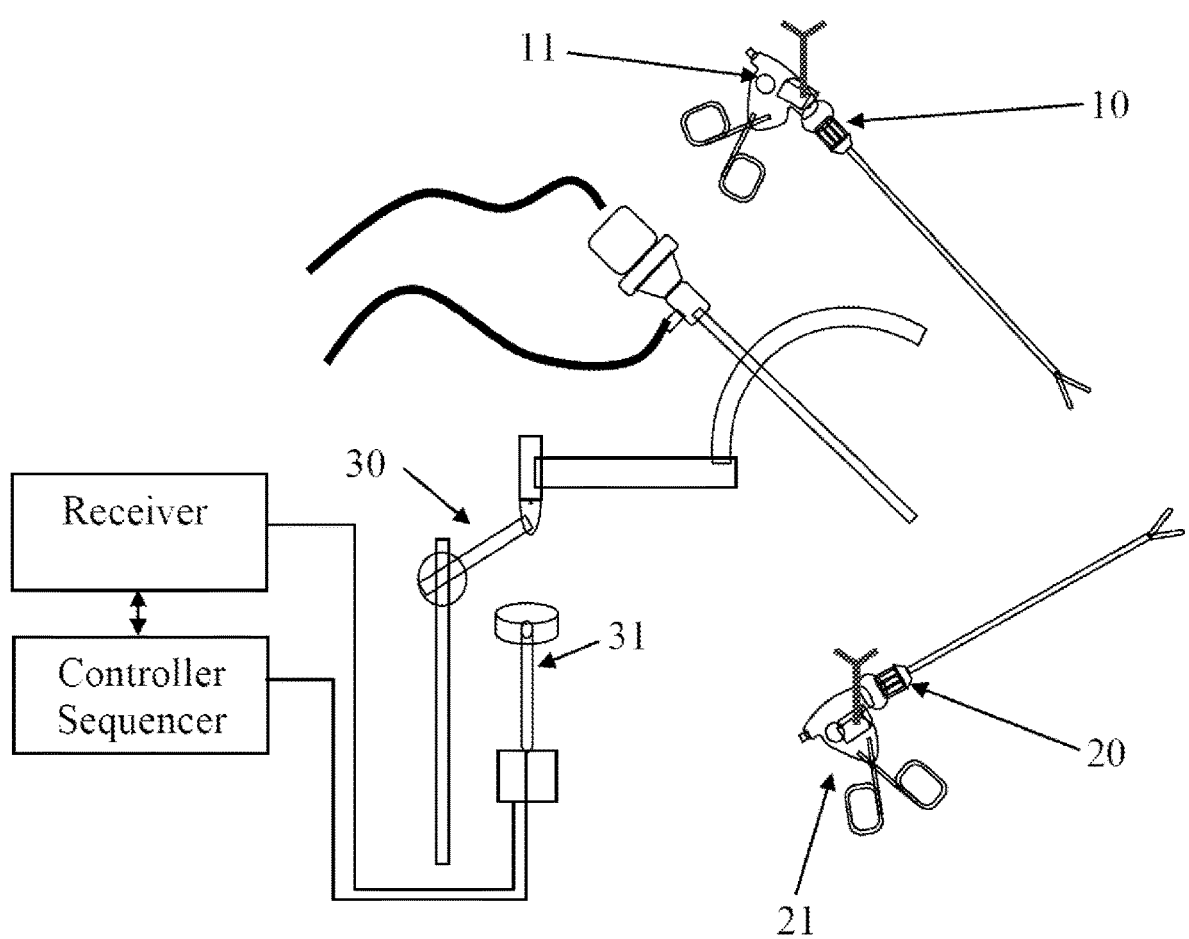

Reference is now made to FIG. 25B which schematically describes the surgical tools positioning AUTOMATIC system according to yet another embodiment of the invention.

As described above, in the AUTOMATIC system the transmitter continuously emits RF signals. Therefore, the receiver constantly communicates with the controller.

The transmitters 11 and 21 can operate in one of three modes: (a) sequential/manual mode, as shown in FIG. 26a, upon the surgeon's pressing an appropriate button (manual mode); (b) periodic/automatic mode as shown in FIG. 26b, in which the transmitters attached to the two tools provide pulsed signals at different pulse rates; or (c) simultaneous/automatic mode, as shown in FIG. 26c, in which the two transmitters transmit simultaneously and continuously, but at different radio frequencies. In all three modes, the receiver can detect and process individual reception from any one of the two tools and identify which transmission belongs to which tool.

Figure 27A:
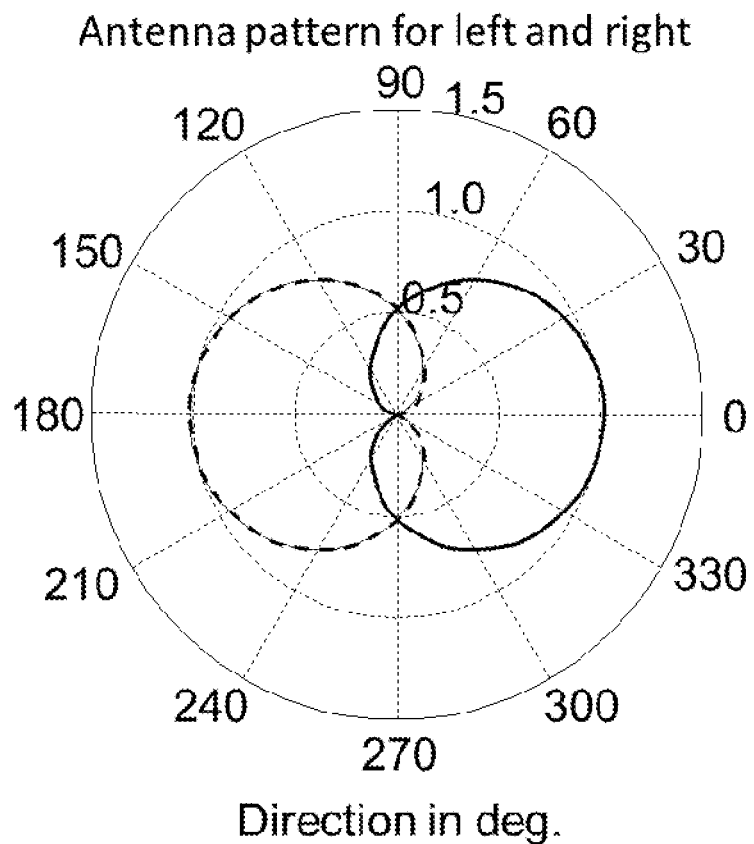
FIGS. 27A-B schematically illustrates a view of the antenna pattern.
Figure 31A:
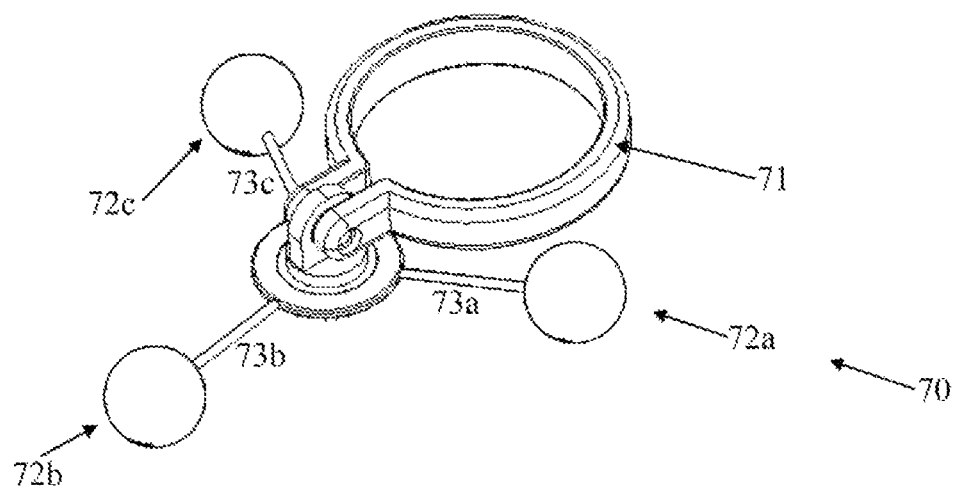
FIGS. 31A-C shows examples of planar and spatial antenna structures.
Figure 32A:
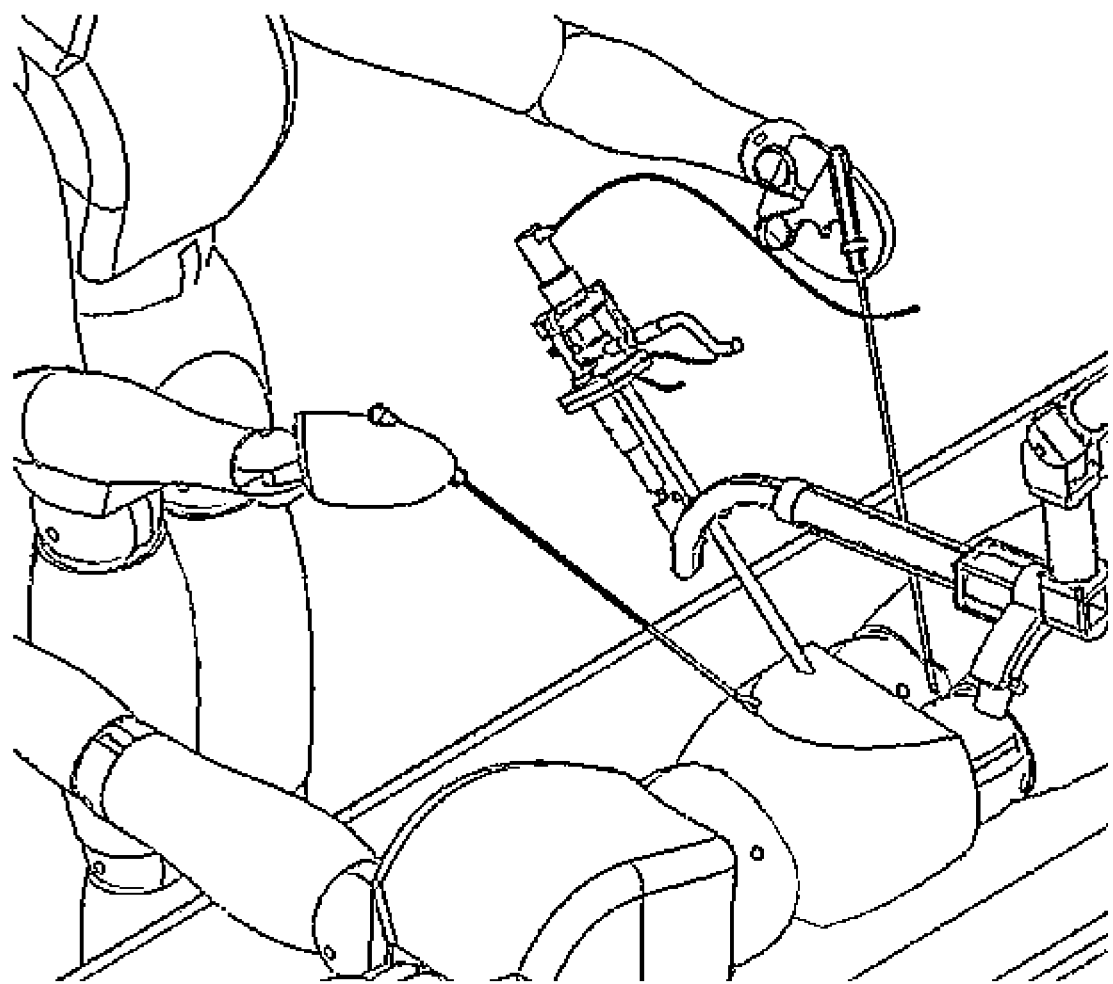
FIGS. 32A-B shows examples of the use of the location system, with FIG. 32A schematically illustrating use of the location system in abdominal laparoscopic surgery and FIG. 32B schematically illustrating use of the location system in knee endoscopic surgery.

Reference is now made to FIGS. 27A, B, 28A through 28D, and 29, in which further details of the system operation are illustrated. The receiver receives sequentially the signal of each tool through the antenna set, the antenna set comprising at least one (preferably) multiple directional antennas array as shown in FIG. 31A, where at least one of the antenna is connected to the receiver. In order to locate the transmitter, at least two directional patterns are required as illustrated in FIG. 32A. The figure illustrates a typical antenna's pattern as a function of the signal's angle and of the intensity.

Alternatively, the transmitted signal may be modulated (in different embodiments of the invention, either (a) frequency modulation or (b) amplitude modulation or (c) both FM and AM simultaneously). Thus, in order to identify the arm from which the transmission is being received, each transmitter has a different modulation frequency. Hence an easier detection of the arm is enabled. In general once the correct transmitter has been identified, the following mathematical analysis is performed:

The direction of each transmitter (and hence the desired instrument) is calculated by using a single receiver having at least 3 directional antennas.

The received signal strength (RSS) is a function of the distance (d) between the receiver and the transmitter (i.e., the instrument); the strength of the transmitted signal (P); the path loss exponent (11); and the antenna's gain (Gr).

Since all the antennae are co-located, the ratio of the RSS will be the ratio between the antennas' gain.

Therefore, by knowing how the gain ratio varies with the angle—one can calculate the angle from which the signal has been transmitted.

The above mentioned mathematical analysis id performed based on the following facts:

The method uses several directional antenna that are co-located as a set of receiving antenna; and the transmitter is assumed to be located somewhere around the receiving antenna set.

As described, the method is adapted to find only the direction of the transmit antenna by comparing the received power from all antenna in the set. As commonly known, the received power depend on the transmit power (PT), the distance from receiving to transmit antenna (d) and on the receiving antenna gain (Gr(i)) in the direction of the transmitter. Since the set of antenna are co-located (the transmit power (PT), the distance from receiving to transmit antenna (d) et cetera are eliminated) and the ratio of the receiving signal strength (RSS) is as follows:

$$RSS(\text{antenna}(i)) - RSS(\text{antenna}(k)) = Gr(\text{antenna}(i)) - Gr(\text{antenna}(k))$$

As can be seen, the difference in the RSS does not depend upon the transmit power PT (since the PT received by each antenna is the same), and it does not depend upon the distance (since the received antenna are co-located).

From the difference set of RSS, the difference in the gain between the receiving antennas is known.

Figure 27B:
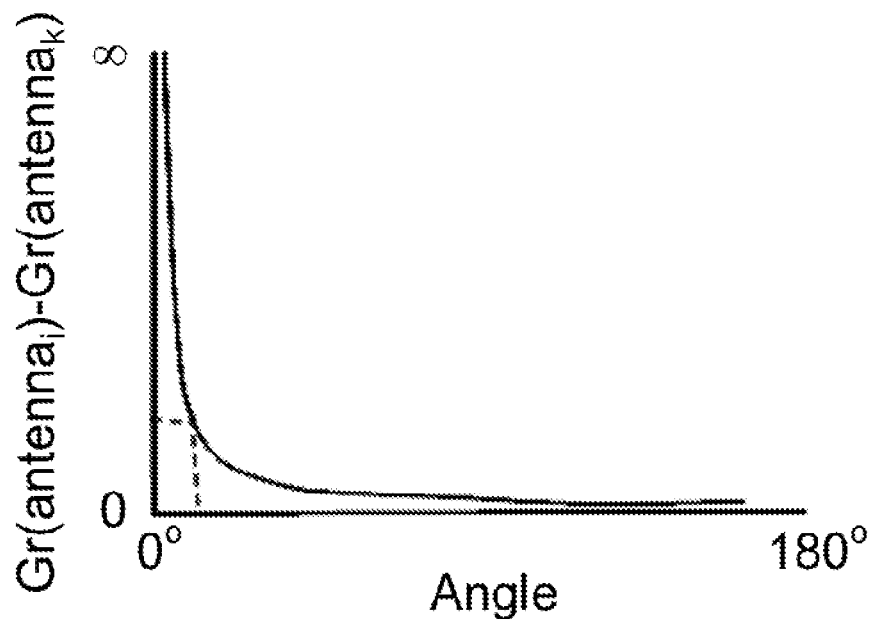

Since the receiving antennas are directional, the gain pattern is dependent only upon the angular positioning of the transmitter (and hence the instrument). Therefore, the angular position and hence the direction can be resolved unambiguously from the gain difference, and it is therefore possible to calculated the angle from which the signal has been transmitted from a measurement of how the gain ratio varies with the angle (see FIG. 27B). As illustrated in FIG. 27B, once the RSS difference is known, the angle from which the signal is being sent (i.e., the angular location of the transmitter and hence the instrument) can be calculated.

It should be noted that the above mentioned calculation is much less sensitive to multipath environment found whilst applying the methods in laparoscopic surgeries.

Figure 31B:
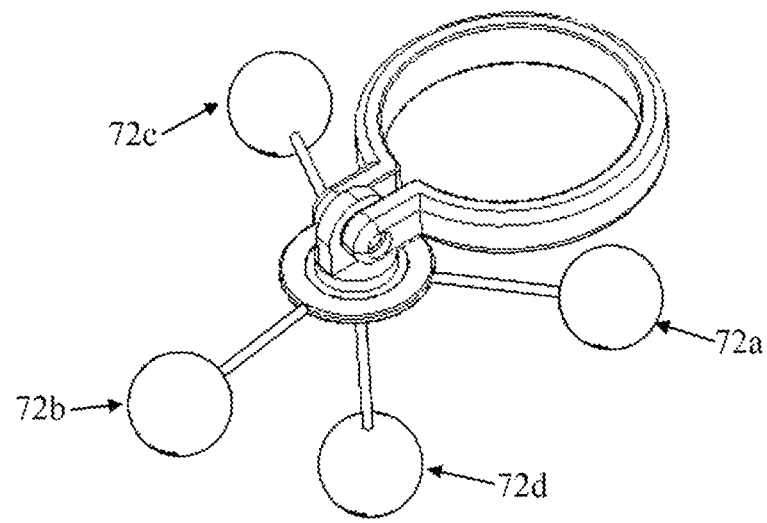

According to another embodiment of the invention, the antenna array has more than two patterns, allowing the system to identify the direction of the tool with a finer resolution. Reference is now made to FIG. 31B, in which a non-limiting example of an additional embodiment is illustrated, in which the antenna array comprises four directional patterns: left, right, forward and aft. From the direction from which the strongest reception is received, the system is able to identify the sector in space in which the tool is located. Moreover, from interpolation of the received power from all antenna patterns, even finer directional resolution is possible.

Figure 28A:
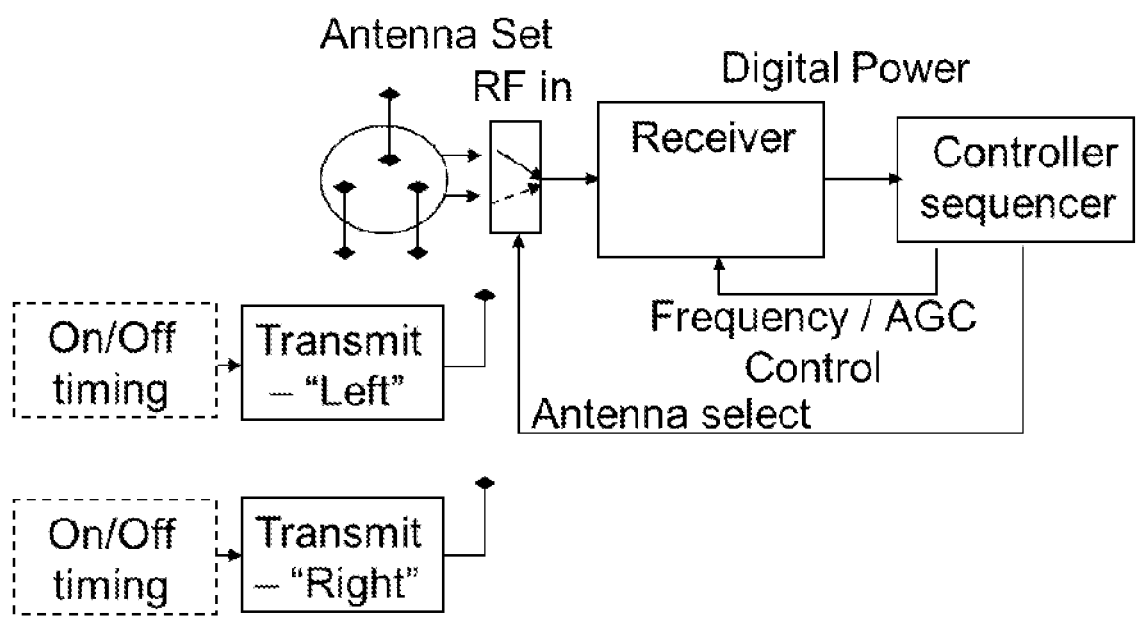
FIGS. 28A-D shows block diagrams, with FIG. 28A being a block diagram of the location system, FIG. 28B being a block diagram of an antenna set, FIG. 28C being a block diagram of the internal receiver and FIG. 28D being a block diagram of the controller/sequencer.

The receiver detects the received signal power for each antenna in the array and reports it to the controller. The controller then resolves the directions of the two tools relative to antenna 31. Transmitters 11 and 21 shown in FIG. 28A may transmit in a wide range of frequencies; a typical frequency is the ISM band of 430 MHz. Transmission is done at very low power, generally below about 1 mW. The transmitted signal is modulated (in different embodiments of the invention, either (a) frequency modulation or (b) amplitude modulation or (c) both FM and AM simultaneously). In a preferred embodiment, the modulation is performed at an audio rate of about 1.5 kHz. The transmitter uses a built-in antenna. In order to identify the arm from which the transmission is being received, each transmitter has a different modulation frequency. In a preferred embodiment of the invention, the frequencies are located within the band encompassing the range of from about 1.0 kHz to about 1.5 kHz.

Figure 28B:
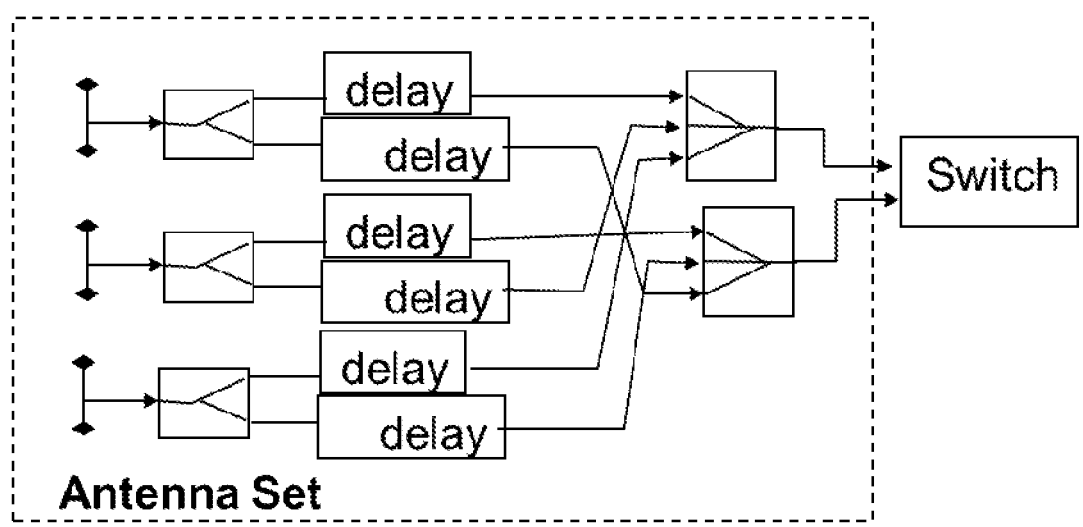

The signal for each transmitter is received by all antennas in the array (see FIG. 28B above). The antennas in the array typically comprise three very short dipoles mounted on the edge of an equal edge three-legged star or circle, as shown in FIGS. 31A and 31B. The diameter of the circle or three-legged star is about 8 to 12 cm for operation at about 430 MHz. The use of the antenna array to identify the beam pattern is illustrated schematically in FIG. 28B. The antenna pattern is formed by combining the signal received by each antenna with different delays and signal weights. In order to set the pattern, in a typical embodiment, each antenna output is split into several equal power signals and a sample of each antenna signal is combined into one directional output. Which output is being measured is selected by an external switch.

The receiver receives the signal in sequence from each directional pattern and detects the signal power in any pattern for the signals from both tools; from the power ratio the signal direction is calculated. For example, for a two pattern antenna (left and right) if the signal from left antenna is much stronger than from right one, then the signal must have arrived from the left and vice versa. In parallel, the signal modulation as transmitted is detected and the modulation frequency is measured. Since each transmitter has a different modulation frequency, identification of the transmitter from which a particular signal originates is straightforward.

Figure 28C:
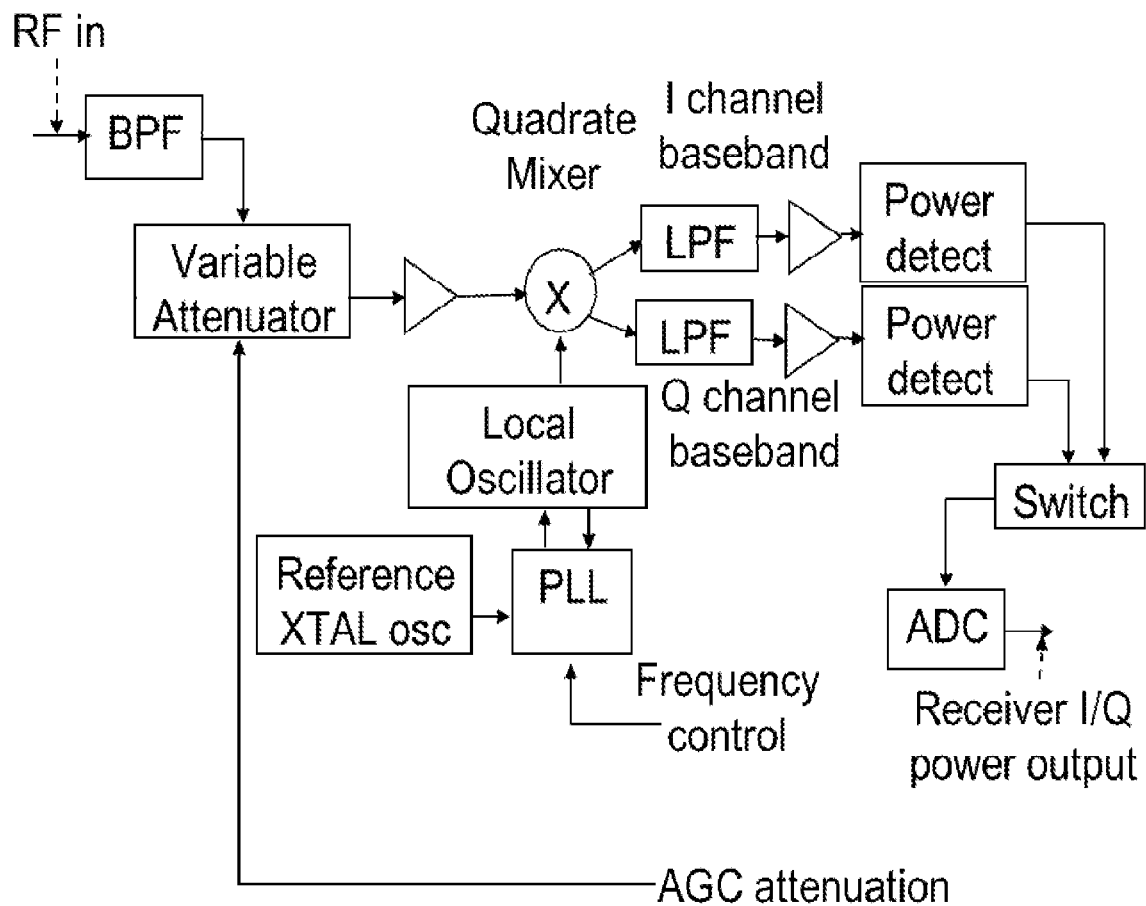

The receiver may be of any type, but in order to reduce the cost, size and power consumption, in a preferred embodiment, the receiver is a single conversion receiver that converts the input signal to base band. The receiver block diagram is shown in FIG. 28C. The receiver operation is as follows: the RF input is filtered around the transmitter frequency band then passed through a variable attenuator controlled by the system controller. Next, it is then amplified and then down converted using a Quadrate mixer and a local oscillator. The mixer outputs are the IF baseband: I (in phase) and Q (Quadrate) outputs, which are filtered by two low pass filters (e.g., about 30 kHz) then amplified. The base band signal powers are then detected. The DC power relative to the signal power is selected in sequence. The analog signal is then passed to an analog to digital converter (ADC), following which the total received power is computed digitally.

Figure 28D:
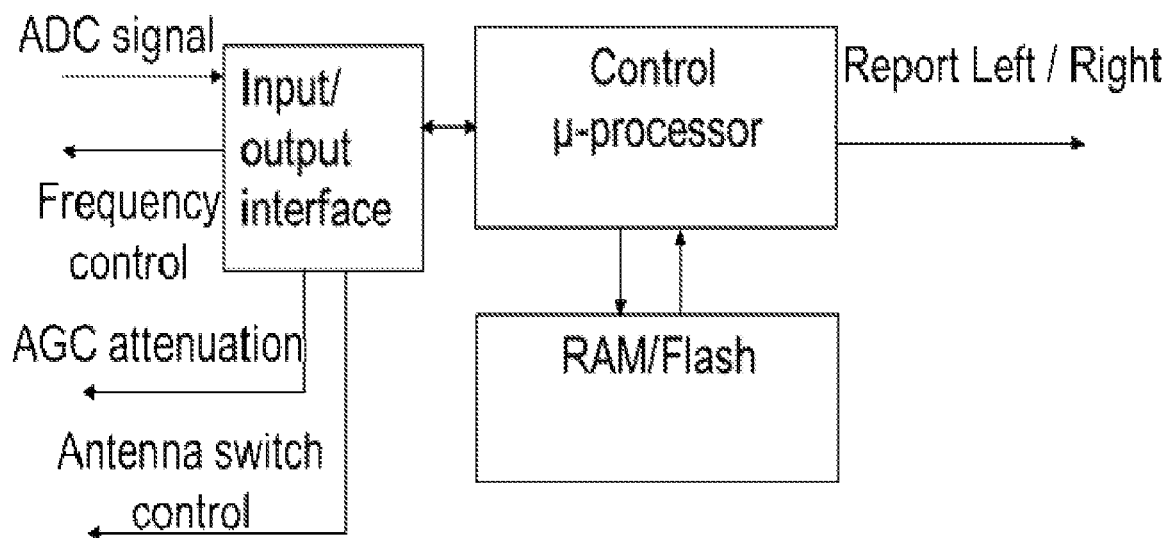

In an additional embodiment of the invention (not illustrated), the base band signal is analog to digital converted, so that the power of both the I and the Q channel is converted to a digital value. The local oscillator frequency is locked by the PLL to the XTAL reference oscillator, controlled by the system controller. In order to ensure that received signal is within a limited range the receiver gain is adjusted automatically (AGC). Finally, as shown in FIG. 28d, the digital signal power is transferred to the system controller, where the controller calculates from the time of reception from which tool it is received and from which antenna pattern, using the power the controller compute the tool direction for each of the two tools.

Figure 29:
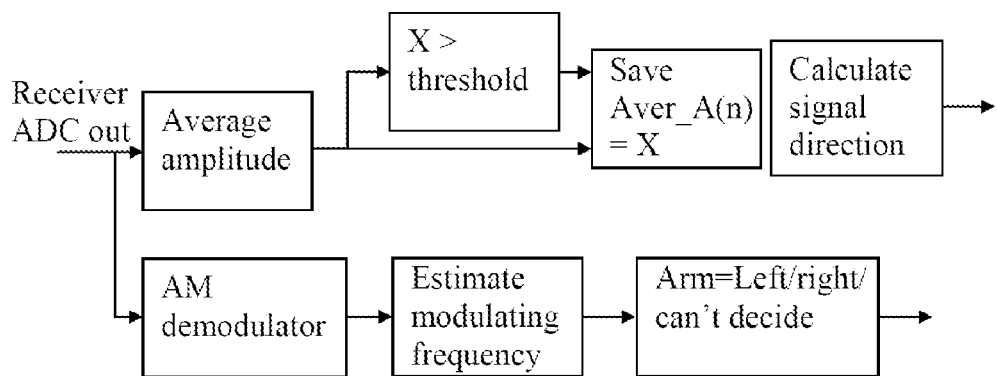
FIG. 29 shows system control software operation flow.

The controller includes a timer based sequencer, preferably built into the microprocessor timing unit, that switches the receiver antenna, and in case of multiple frequency transmission, sets the receiver frequency sequentially. The operation sequence of the system is illustrated schematically in FIG. 29, which shows the system control software operation flow:

[1] The AD signal is averaged to detect the average amplitude, averaging being done over one dwell duration ("X" indicates the output after averaging);
[2] Signal presence is detected when X is above a predetermined threshold;
[3] Average amplitude X is saved in a vector array (Aver_A (n), n={1, 2, . . . N}) if signal is present, the storage being done on the appropriate antenna number place in the array;
[4] If for a given antenna, signal is present on N successive dwell durations, the signal direction is calculated;
[5] The modulation (in the particular embodiment illustrated, AM) is detected from the signal power input;
[6] The modulation frequency is measured; and,
[7] From the measured frequency, the arm type is detected; in the case of weak signal or simultaneous transmission, the module reports "can't decide," indicating a garbage signal.

In embodiments in which the transmitter operates periodically, both transmitters operate for a fraction of the time then switch off, then switch on again and so on with a constant or random cycle periodicity, each transmitter transmitting with a different transmission pulse cycle time in order to ensure that transmissions will not overlap at all times but only at times separated by t1•t2, where ti and t2 are the pulse cycle times of the two transmitters. In parallel, the receiver sequentially switches the receiver channel among the different antennas and dwells on each antenna for a fixed dwell time. From the level of signal received, the system determines whether or not a signal is present. If a single signal is present either from the right arm or left arm transmitter, the direction of the signal is calculated from the signal strength received from different antennas, and the arm is identified from the internal modulation frequency. In case of coincident simultaneous transmit the receiver cannot identify the signal modulation therefore the measurement is rejected. In an additional embodiment, the system tracks the transmission period cycle of each arm and predicts the simultaneous transmission times in order better to identify which arm's signal is being detected.

Figure 30A:
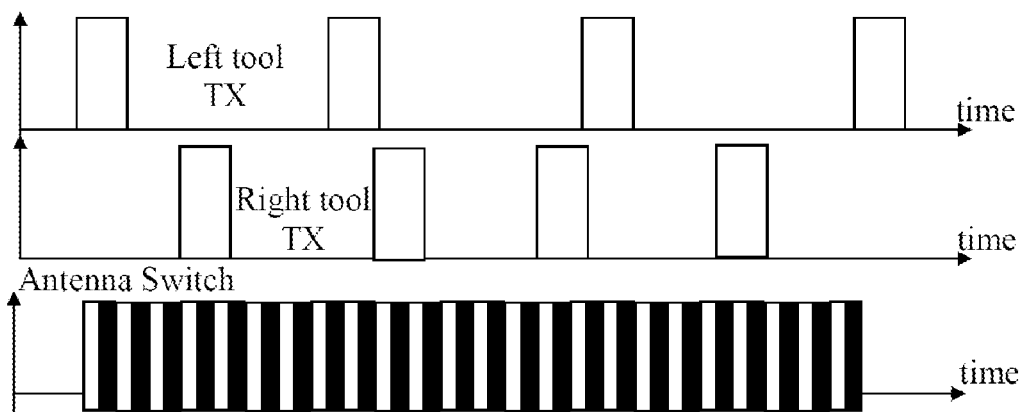
FIGS. 30A-B shows the antenna switching pattern, with FIG. 30A schematically illustrating the antenna switching pattern during periodic transmit operation and FIG. 30B schematically illustrating the antenna switching pattern during sequential transmit operation.

In order to ensure that the direction of a single transmission can be calculated (if only a single transmission is received), the "transmit on" duration is at least (N+1) X dwell intervals, where N is the number of antenna outputs. This ensures that the transmission is received during at least N successive dwell times, allowing the system to calculate its direction. For example if the receiver antenna is switched in sequence staying on for 10 ms (i.e., a 10 ms antenna dwell time) in each pattern out of two patterns, then the total antenna switch time cycle is 20 ms, and the transmitter switch on time is required to last for at least 30 msec. For example, in one embodiment of the invention, the transmit on/off cycle times are 120 ms and 150 ms for the left and right arm transmitter respectively. Each transmitter is on for 30 ms and off for the rest of the time. The antenna switch versus transmit periodic operation is shown in FIG. 30A.

Figure 30B:
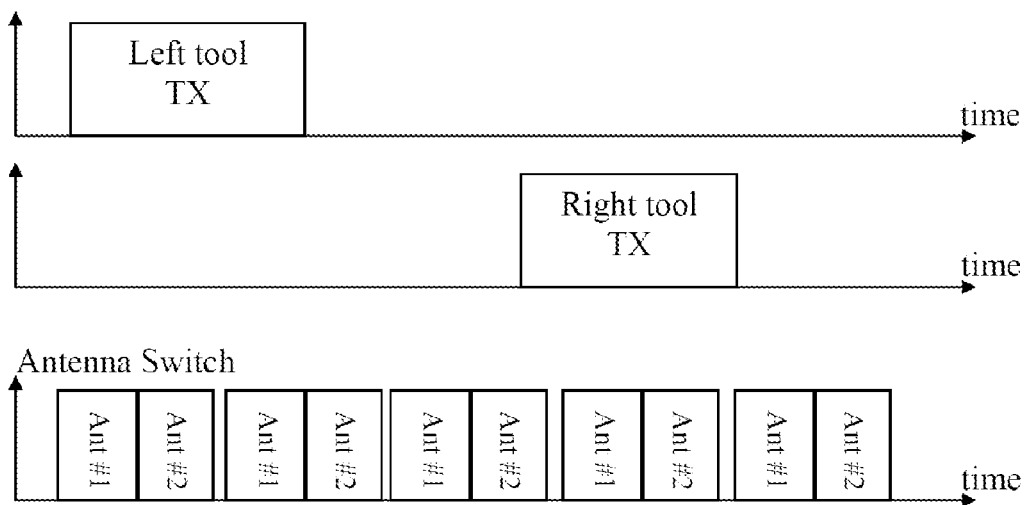

In the case of sequential transmission, each transmitter should be on for at least (N+1) X dwell intervals (receiver antenna dwell time). The antenna switch versus transmit sequential operation is shown in FIG. 30B.

In embodiments in which the two transmitters operate at different frequencies, the receiver scans all antenna patterns at the first frequency, then switches to the second frequency and scans all antenna patterns again, then returns to the first frequency, and so on.

Reference is now made to FIG. 31A, which illustrates an embodiment of the invention in which the directional antenna array has a planar structure. The short dipoles at each segment 72*a,b,c* are covered to protect the wires and the circuits from humidity and mechanical fractures. The arms 73*a,b,c* are made of any appropriate flexible material.

Reference is now made to FIG. 31B, which illustrates an embodiment of the invention in which the directional antenna array has a non-planar spatial structure. The fourth short dipole at segment 72*d* is not located in the plane that contains segments 72*a,b,c*. This arrangement allows the system to compute the spatial direction of the RF transmitter.

Figure 31C:
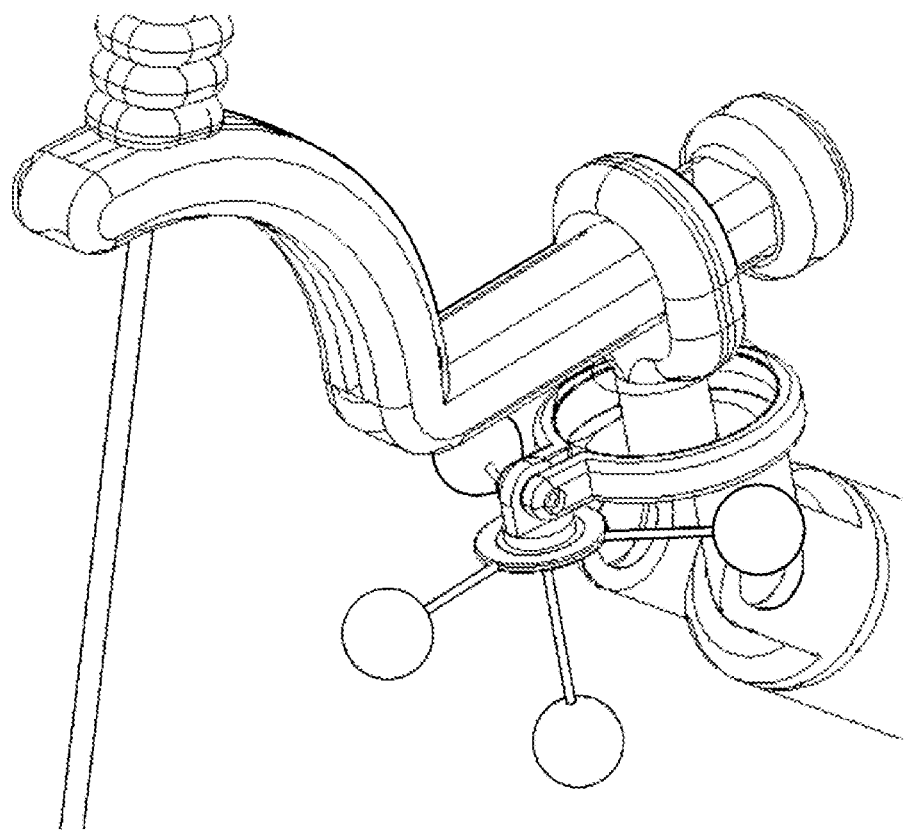

Reference is now made to FIG. 31C, which shows the antenna located on an automated assistant maneuvering system according to one embodiment of the invention.

Reference is now made to FIGS. 32A, B, C, which illustrate in a non-limiting manner some types of surgeries in which the location system disclosed in the present invention can be utilized.

FIG. 32A shows an example of using the location system in abdominal laparoscopic surgery.

Figure 32B:
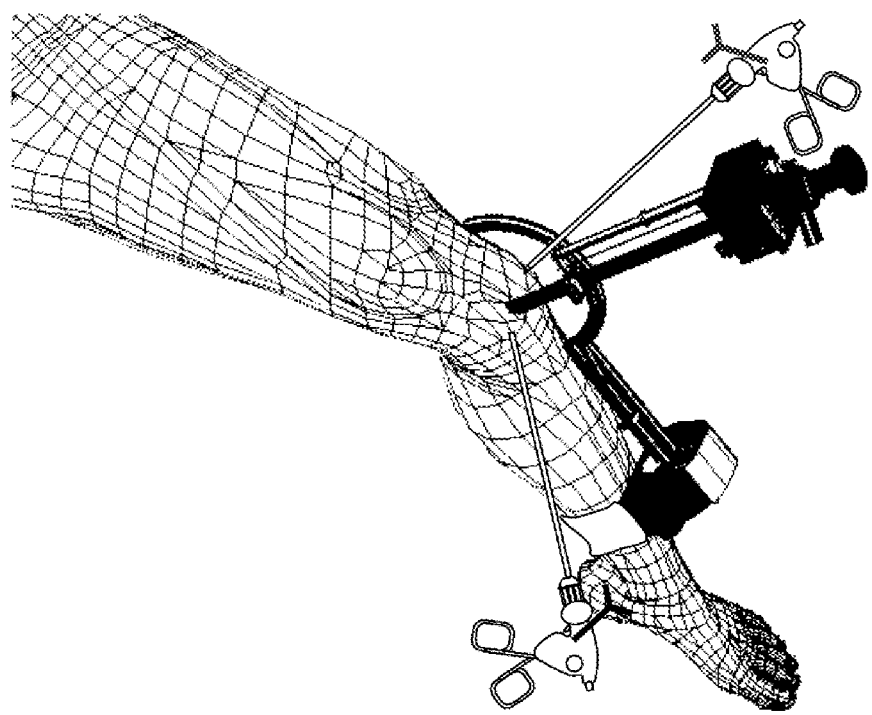

FIG. 32B shows an example of using the location system in knee endoscopic surgery.

Figure 33A:
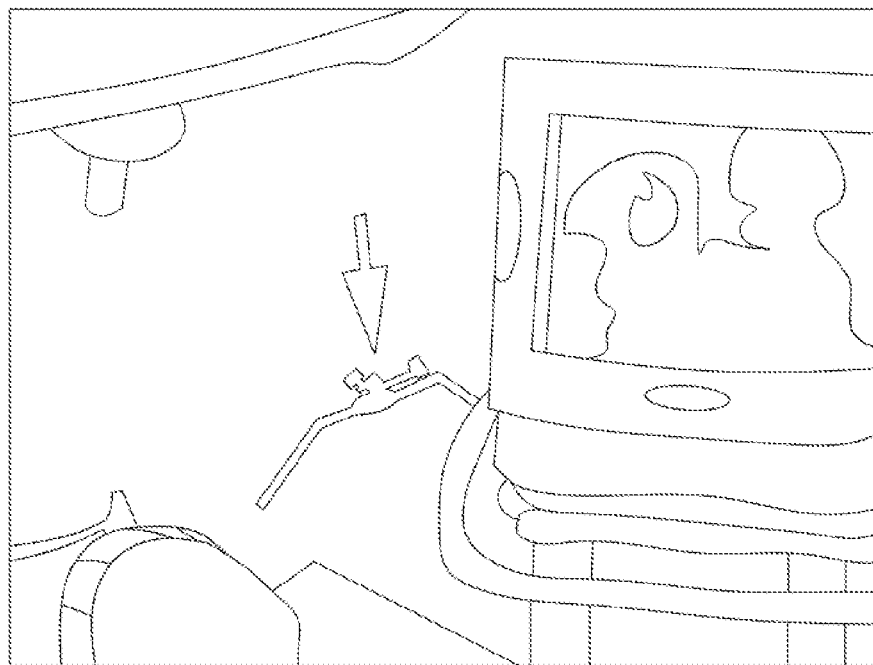
FIGS. 33A-C shows aspects of the invention particularly suited for sinus surgery.
Figure 33B:
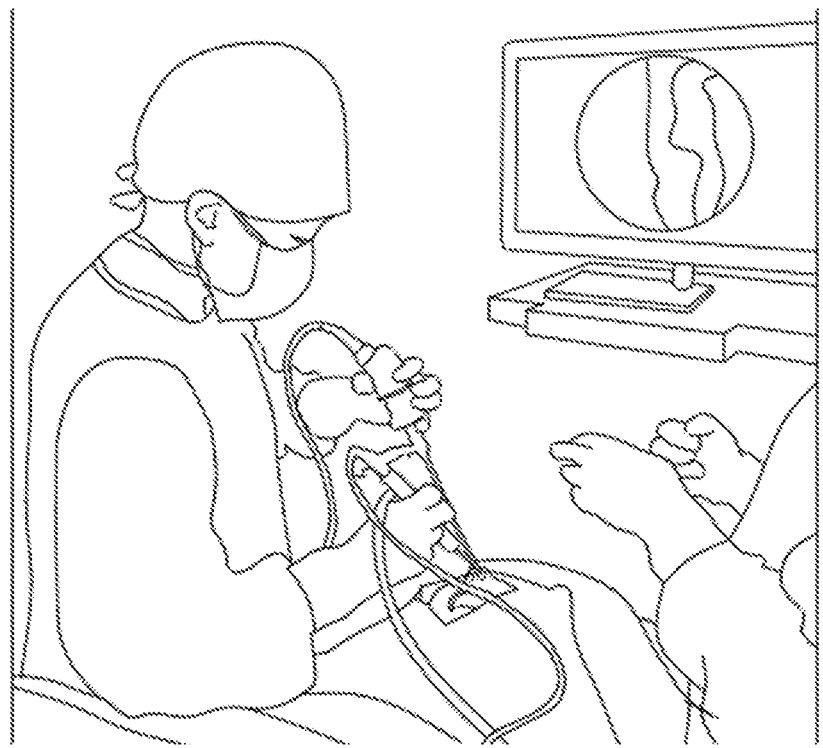
Figure 33C:
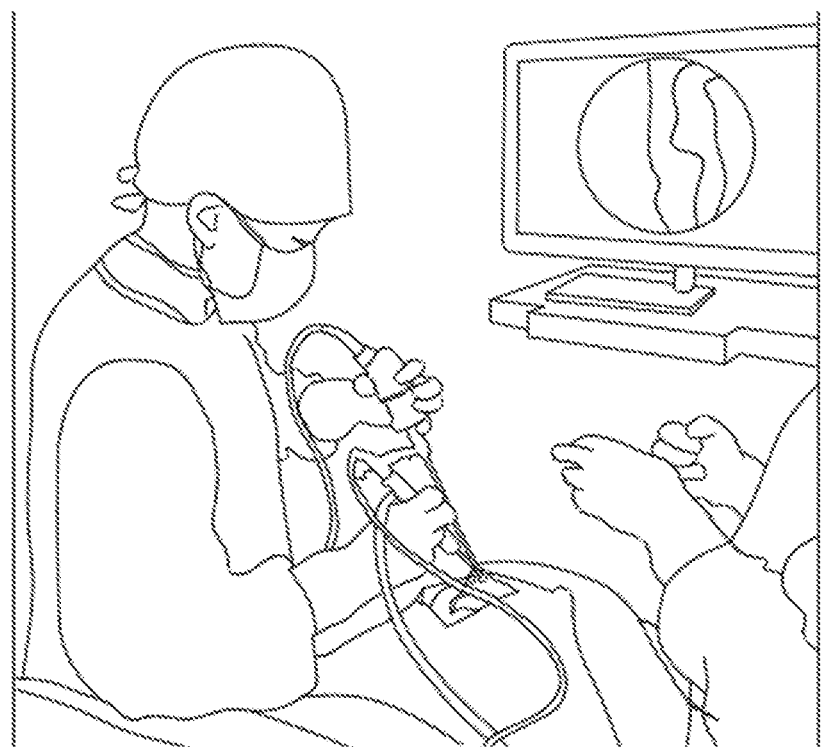
Figure 34A:
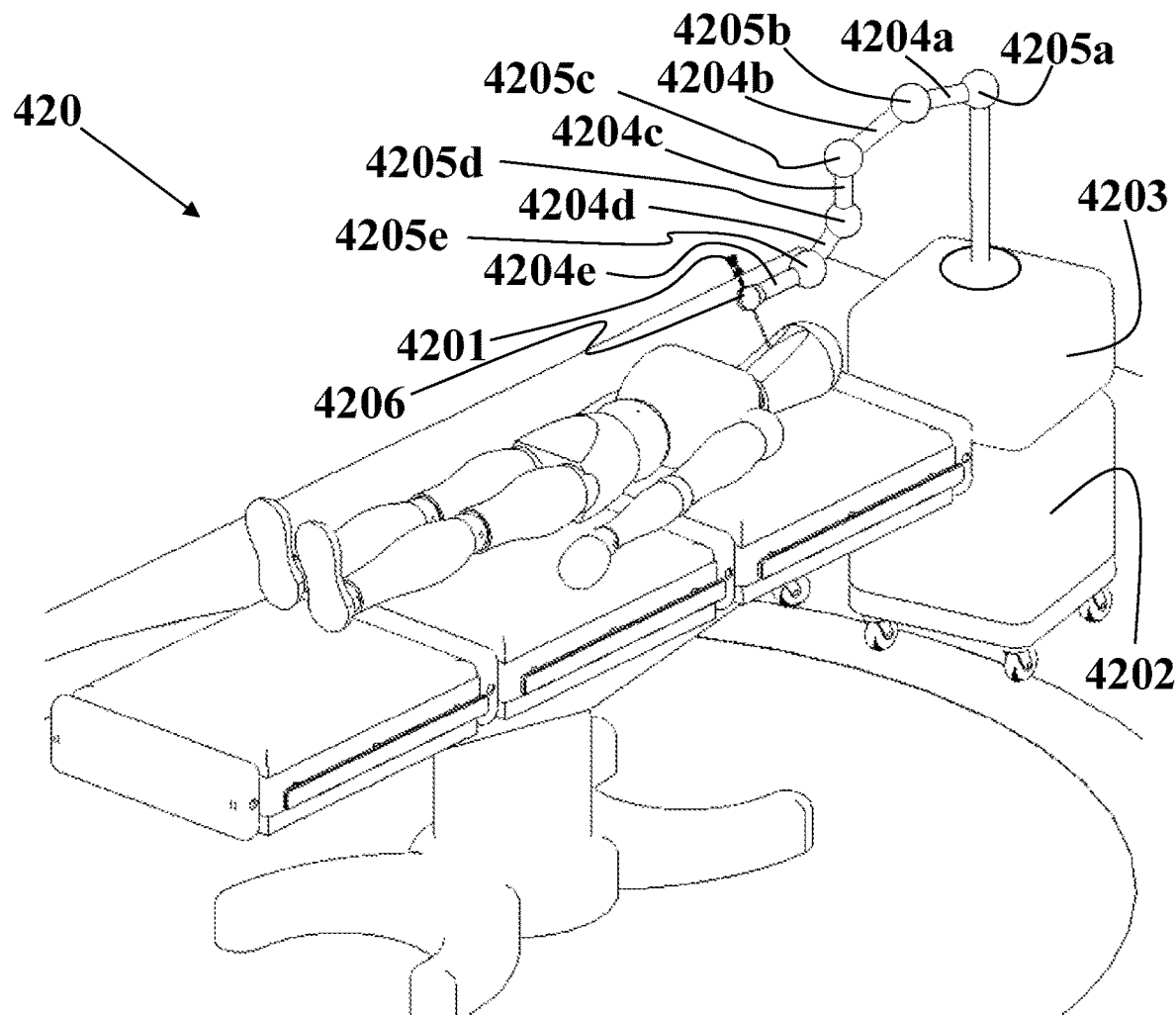
FIGS. 34A-B illustrates an embodiment of a system using the coupling of the instant invention.
Figure 34B:
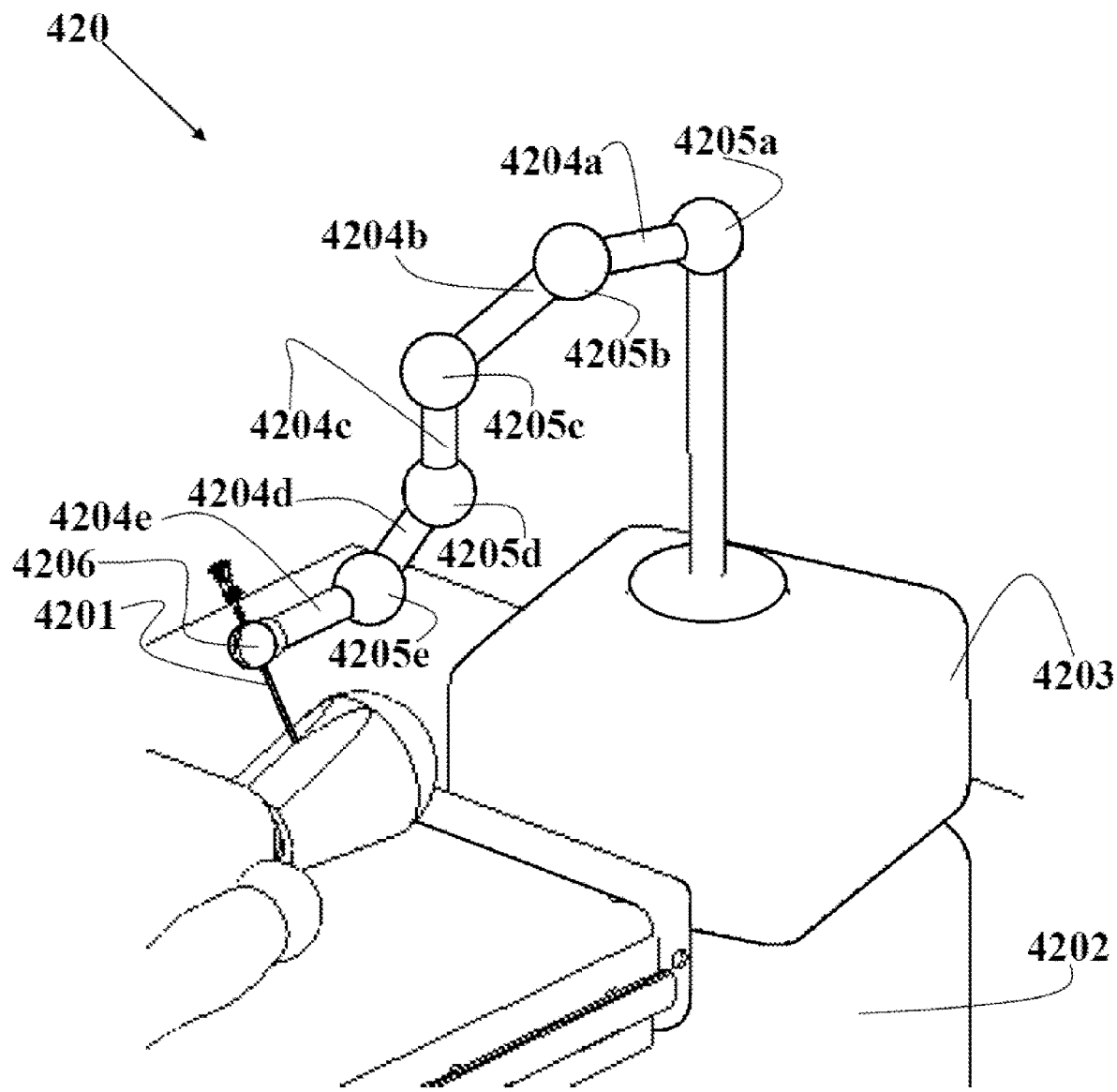

In FIG. 33A-C another aspect of the invention is shown particularly suited for sinus surgery. Reference is now made to FIG. 34, which illustrates an additional embodiment 420 of the invention herein disclosed. Surgical device 4201 is held in position by robot end effector, which comprises a plurality of shaft tubes 4204 (in the embodiment illustrated, there are 5 shaft tubes 4204*a*-4204*e*) connected in series by a set of joints 4205. One of said joints (in the embodiment shown, 4205*a*) connects the first shaft tube 4204*a* to the body of the instrument, while another (in the embodiment shown, 4206) is attached the final shaft tube (in the embodiment shown, 4204*e*) and comprises means (e.g. a closeable slot or hole) to hold the surgical device in a position fixed relative to the final shaft tube. Motor means for effecting movement of the shaft tubes is contained within motor box 4202, and the controller mechanisms are contained with controller box 4203.

Figure 35A:
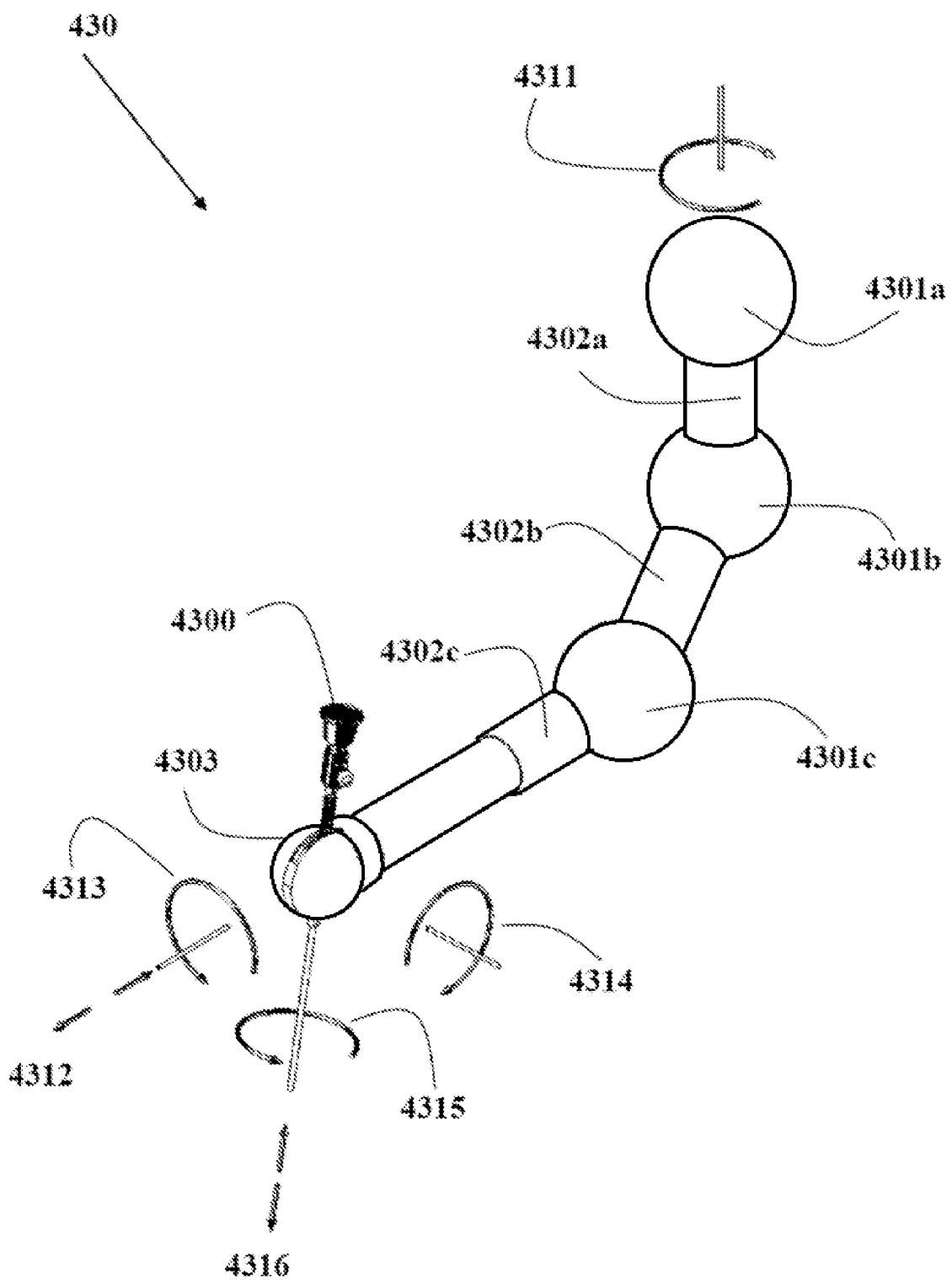
FIGS. 35A-D illustrates modeling of the motion of a surgical device attached to the invention as the motion of a bead rotating in space.
Figure 35B:
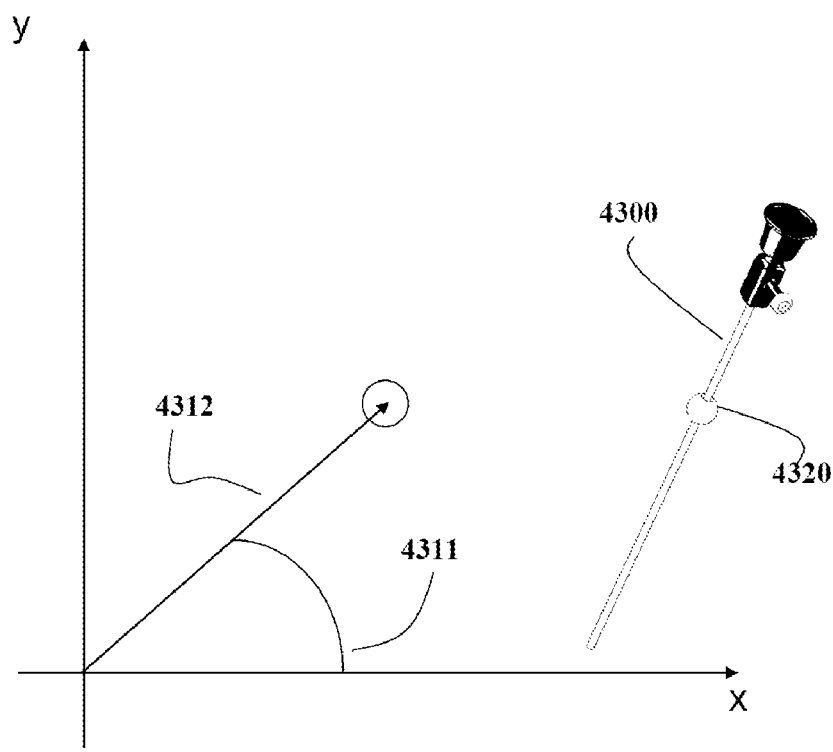
Figure 35C:
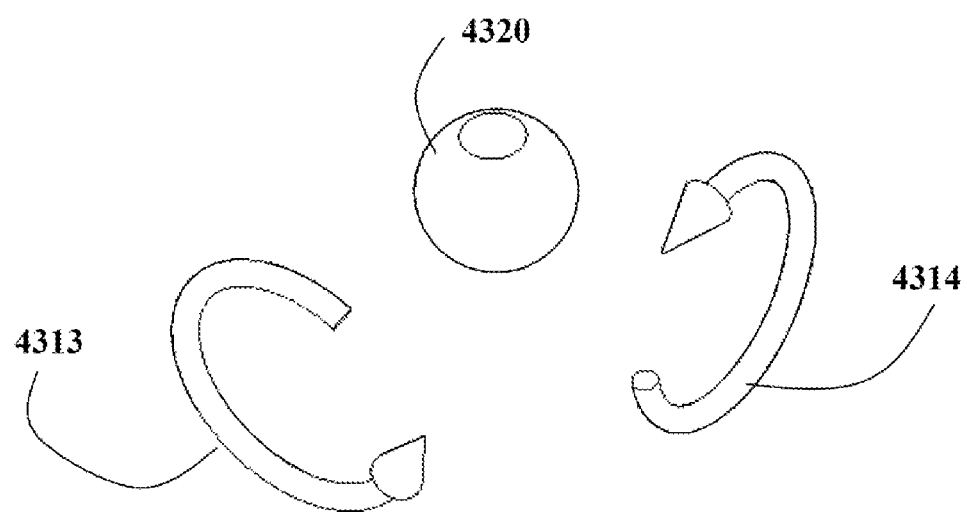
Figure 35D:
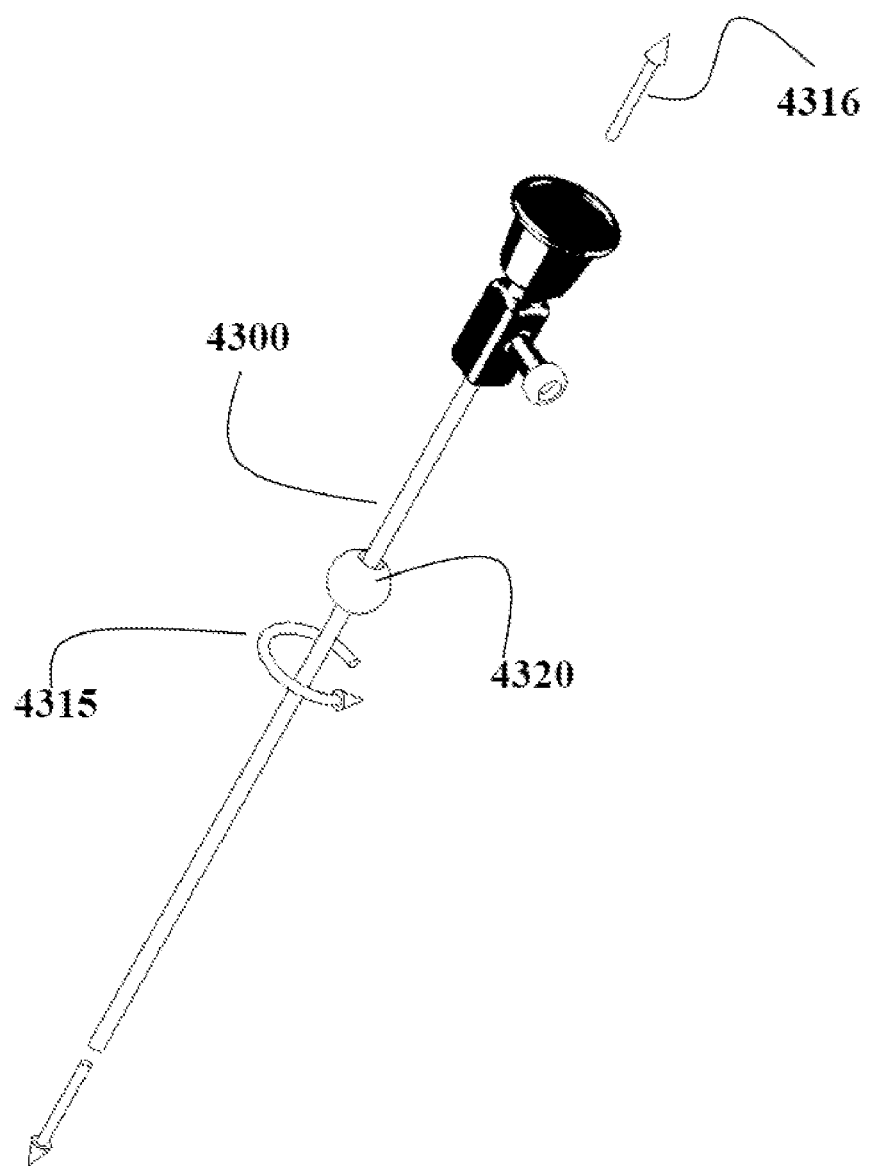

Reference is now made to FIG. 35A, which illustrates the various DOF and an external view of the means for connecting medical device 4300 to the control unit according to an embodiment 430 of the invention. According to this embodiment, 6 independent DOF are available to the medical device (FIG. 35A): (1) rotation 4311 of the entire connecting means about the z-axis; (2) translation 4312 of the medical device along a predetermined axis within the x-y plane; (3) rotation 4313 of the medical device about the axis defined by 4312; (4) rotation 4314 of the medical device about an axis perpendicular to that defined by 4312; (5) rotation 4315 of the medical device about the z-axis; and (6) translation 4316 of the instrument along the z-axis. Motion about DOF 4312—4316 is accomplished without gross movement of the entire connecting means. As described in detail below, independent motions along these DOF are enabled by a system of n joints 4301 (in the embodiment shown, n=3; in other embodiments, n may be any positive integer) terminating in end joint 4303 and connected by a series of n shafts 4302. As illustrated in FIG. 35B, 4311 and 4312 can be considered a vector in the x-y plane and an angle in the x-y plane relative to the x-axis, respectively. Thus, 4311 and 4312 define the location of a point in space through which the longitudinal axis of the medical device (which is located parallel to the z-axis) passes. This point in space can be thought of alternatively as the center of a bead 4320 through which the medical device passes. As shown in FIG. 35C, rotations 4313 and 4314 can be considered rotations of the bead about two mutually perpendicular axes in the x-y plane. FIG. 35D illustrates how translation 4315 and rotation 4316 are defined relative to the point 4320.

Figures 36A, 36B:
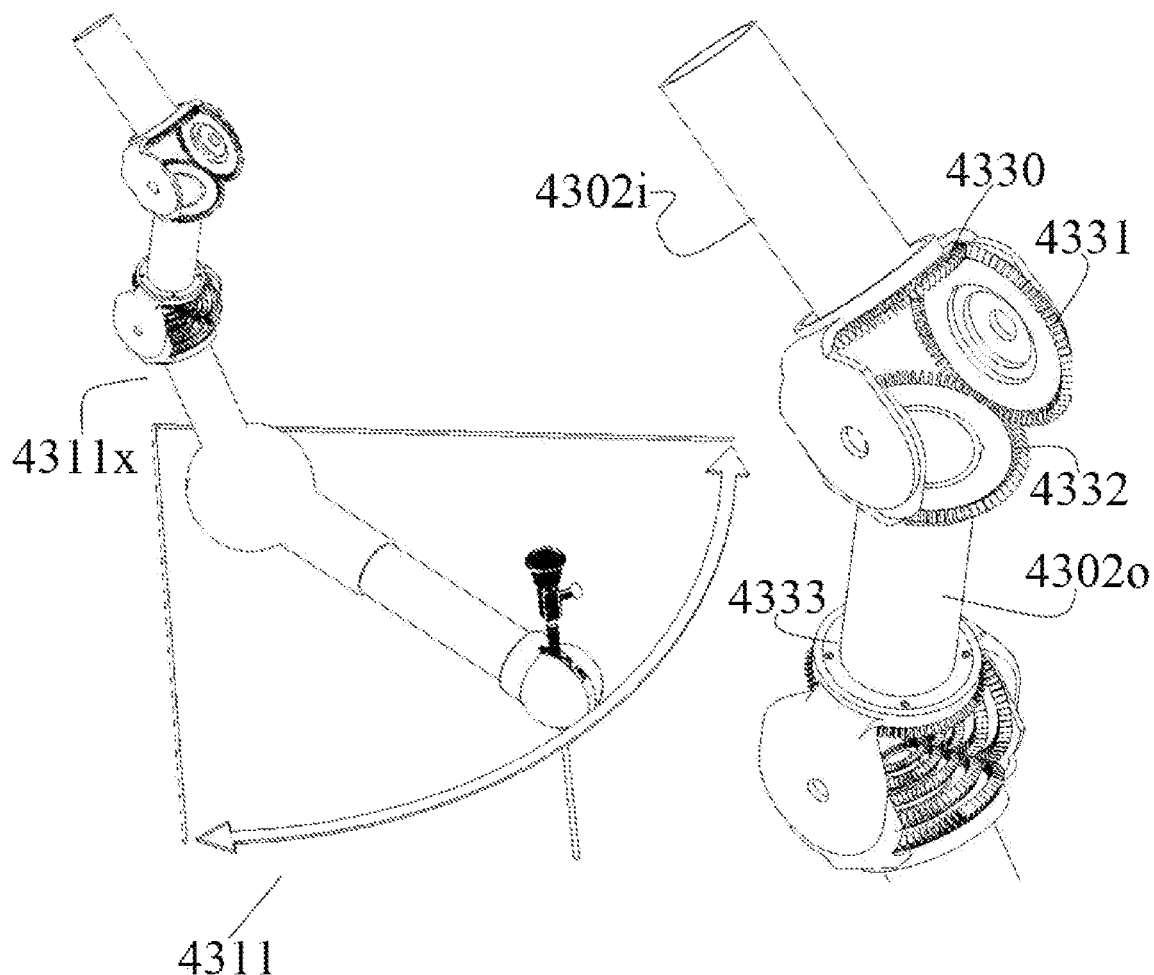
FIGS. 36A-B illustrates means for rotating an end effector in a plane about the long axis of the output shaft ($DOF_1$)

Reference is now made to FIG. 36A, which illustrates means by which motion about DOF 4311 are accomplished according to one embodiment of the invention. Rotation is possible through any arbitrary angle 4311 about rotation axis 4311*x*, as illustrated schematically in FIG. 36A. The motions are enabled by a system of gears, as illustrated schematically in FIG. 36B. The first gear 4330 is mated to input shaft 4302*i*. Intermediate gear 4331 is mated to first gear 4330 and which in turn mated to a second gear 4332 that is rigidly connected to one end of output shaft 4302*o* and rotates around an axis substantially coincident with the longitudinal axis of the output shaft. A plurality of bolts 4333 fix output shaft 4302*o* to joint 4301*a*.

Figure 37A:
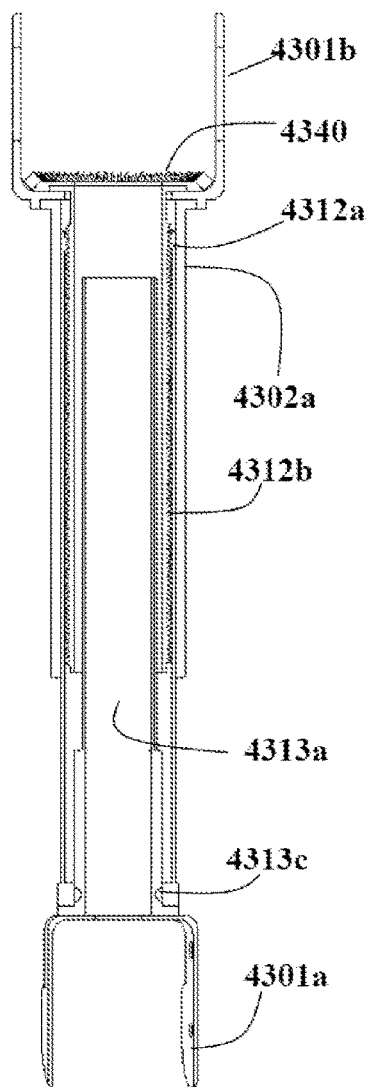
FIGS. 37A-E illustrates means for effecting motion about degree of freedom $DOF_2$ and the bearing that allows motion about degree of freedom $DOF_3$ independent of motion about degree of freedom $DOF_2$.
Figure 37B:
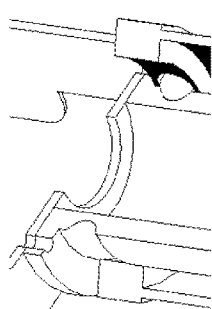
Figure 37C:
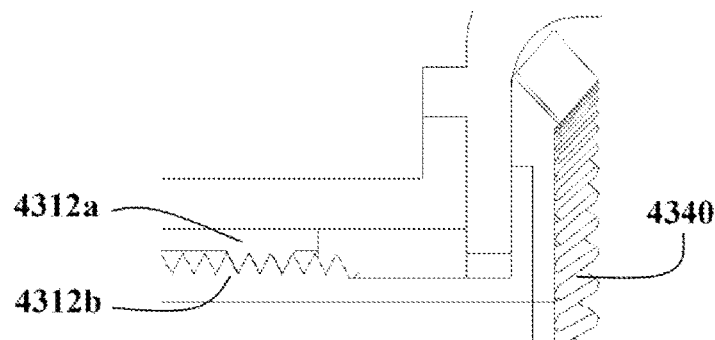
Figure 37D:
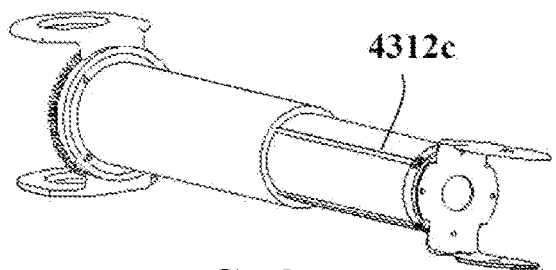
Figure 37E:
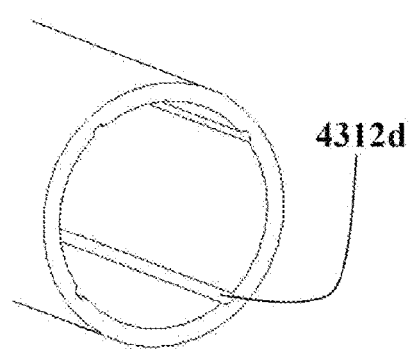

Reference is now made to FIG. 37A, which illustrates means for enabling motion about DOF 4312 and 4313. Illustrated in FIG. 37A is shaft 4302*a*, which connects joints 4301*a* and 4301*b*. Also illustrated is internal tube 4313*a* which contacts shaft 4302*a* via bearing 4313*c*. As illustrated in FIG. 37B, this bearing allows joint 4301*a* to rotate freely about the longitudinal axis of external tube 4313*b* (see FIG. 38). Disposed about at least part of the outer surface of tube 4313*a* is a threaded portion 4312*b*, while a threaded portion 4312*a* is disposed about at least part of the inner surface of shaft 4302*a*; the two threaded regions are in contact such that controlled rotational motion of 4302*a* relative to 4313*a* is possible. The threaded regions are shown in more detail in FIG. 37C. When output gear 4332, which is rigidly connected to one end of tube 4313*a*, rotates, threaded portion 4312*a* necessarily rotates as well. A plurality of protrusions 4312*c* disposed about the outer surface of tube 4313*a* and substantially parallel to its longitudinal axis fit into matching grooves 4312*d* disposed about the inner surface of shaft 4301*a* (the protrusions and grooves are shown in detail in FIGS. 37D and 37E). Because of this protrusion/slot interface, rotation of output gear 4340 cannot lead to rotation of tube 4301*a*.

Figure 38A:
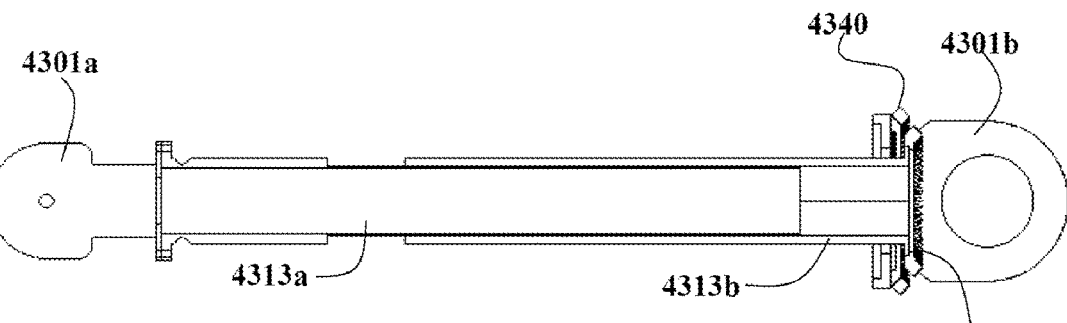
FIGS. 38A-E illustrates the relationships between means for effecting motion about degree of freedom $DOF_2$ and means for effecting motion about degree of freedom $DOF_3$.
Figure 38B:
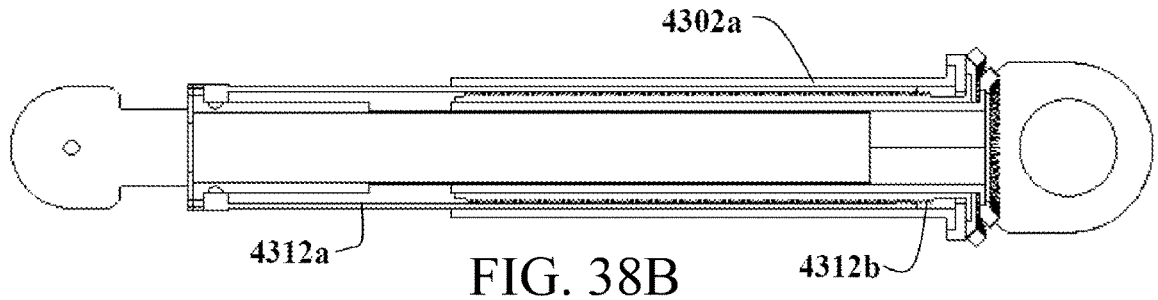
Figure 38C:
Figure 38D:
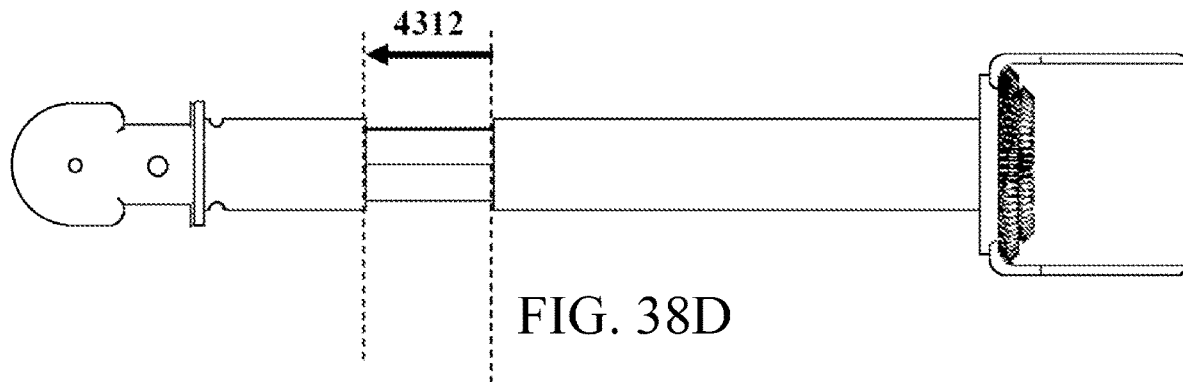
Figure 38E:
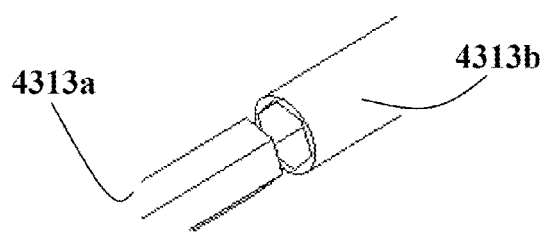

Reference is now made to FIG. 38A, which illustrates means for enabling motion about rotational DOF 4313 and the spatial relationships between the components responsible for this motion and those responsible for independent motion about DOF 4312. Once again, the portion connecting joints 4301*a* and 4301*b* is illustrated. Output gear 4350 is rigidly connected to one end of external tube 4313*b* (FIG. 38A) and rotates about an axis substantially coincident with the longitudinal axis of the tube. As illustrated in FIG. 38B, tubes 4313*a* and 4313*b* are located within shaft 4302*a*, with longitudinal axes substantially coincident. FIGS. 38C and 38D illustrate translation along 4312 and the consequent motions of tubes 4313*a* and 4313*b*. As illustrated in FIG. 38E, the outer surface of internal tube 4313*a* and inner surface of external tube 4313*b* are not circular, but are rather designed to prevent free rotation of the inner tube with respect to the outer tube. In a preferred embodiment, the outer surface of inner tube 4313*a* has a substantially polygonal cross-section, and the inner surface of outer tube 4313*b* is machined substantially to match the shape of 4313*a*. In a more preferred embodiment, the substantially polygonal cross-section is substantially hexagonal. Other shapes are possible, e.g. facing off a portion of a substantially circular cross-section to provide a single planar surface, with the planar surfaces of the inner and outer tubes corresponding to prevent the possibility of free rotation of the inner tube. By this means, rotation of 4313b through an angle θ necessarily leads to rotation of 4313a through the same angle. As illustrated in the figure, rotation through any arbitrary angle θ is possible for any value of the translational extension 4312.

Figure 39A:
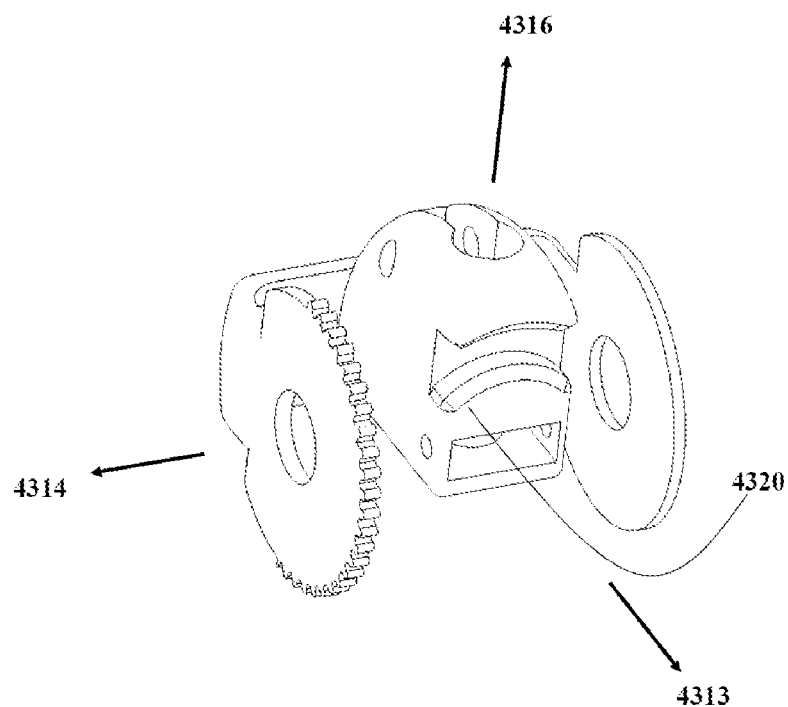
FIGS. 39A-B illustrates means for effecting motion about degrees of freedom $DOF_3$-$DOF_6$.
Figure 39B:
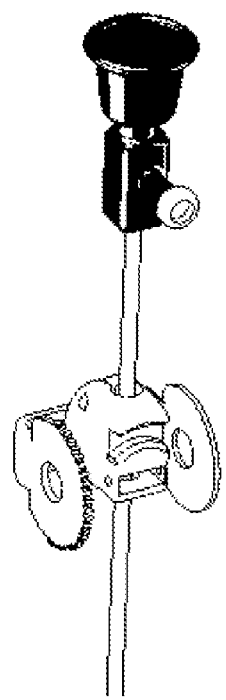

Reference is now made to FIG. 39A, which illustrates the relative motions of DOF 4313-4316. As shown in FIG. 39A, all of the axes of rotation of the distal link meet at point 4320. The rotation axes relative to the long axis of medical device 4300 are illustrated in FIG. 39B.

Figure 40:
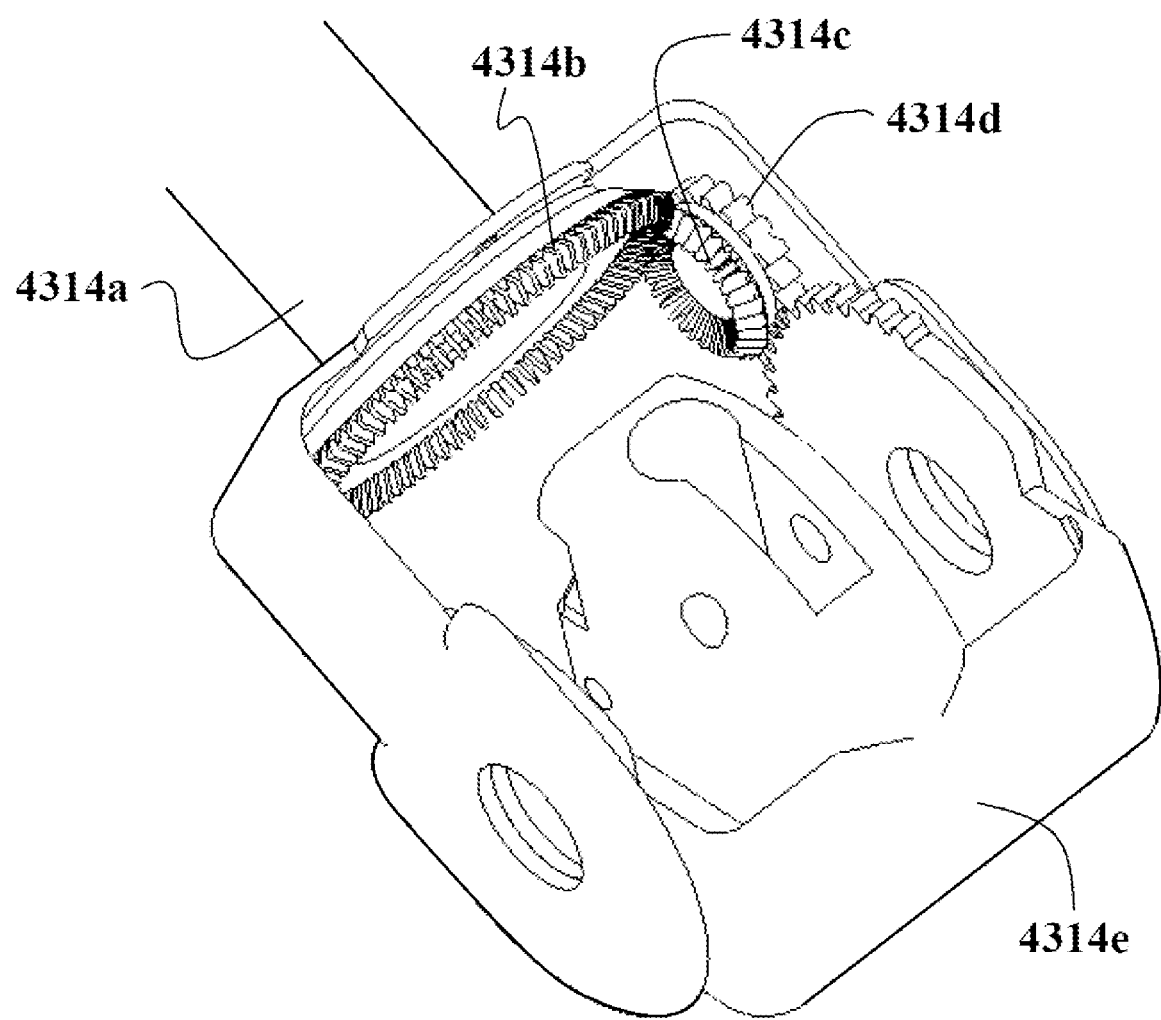
FIG. 40 presents an illustration of the drive means for effecting motion about degree of freedom $DOF_4$.

Reference is now made to FIG. 40, which illustrates means for enabling independent motion about DOF 4314. Input gear 4314b is rigidly connected to one end of internal tube 4314a, with its axis of rotation substantially coincident with the longitudinal axis of 4314a. Input gear 4314b is mated to intermediate bevel gear 4314c, which in general is not in the same plane. In the preferred embodiment illustrated in the figure, the two gears rotate about axes that are substantially perpendicular. Intermediate spur gear 4314d is substantially rigidly connected to, and rotates about substantially the same axis as, 4314c, although, as illustrated in the figure, the ratio between the two gears is not necessarily equal to 1. Intermediate spur gear 4314d is mated to distal link 4314e via interaction with a toothed portion of said distal link. Thus, rotation of internal tube 4314a causes rotation of input gear 4314b, leading to rotation of intermediate bevel gear 4314c and hence rotation of intermediate spur gear 4314d, causing rotation of distal link 4314e.

Figure 41A:
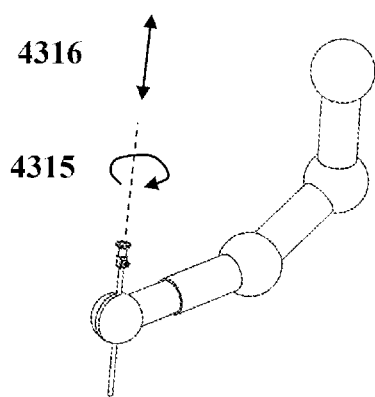
FIGS. 41A-E presents an illustration of the drive means for effecting motion about degrees of freedom $DOF_5$ and $DOF_6$.
Figure 41C:
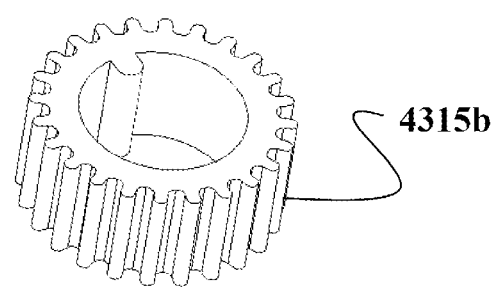
Figure 41B:
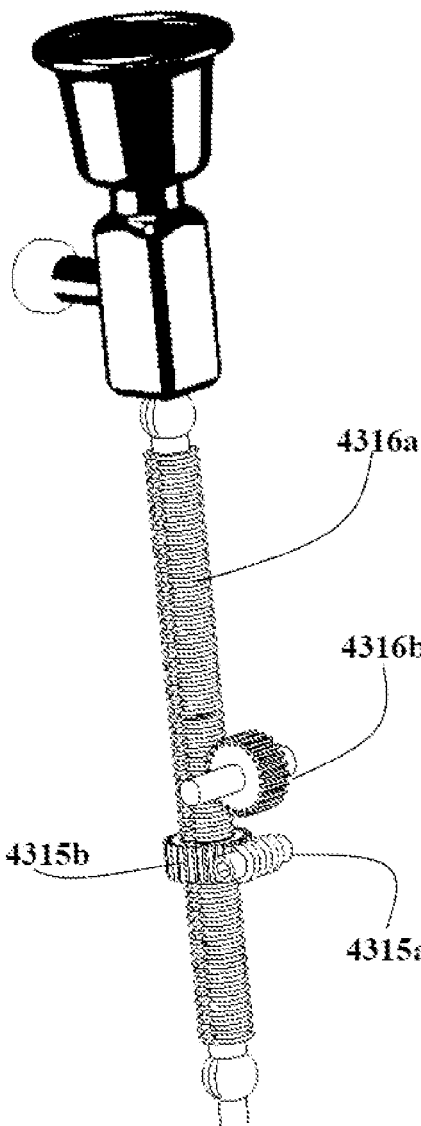
Figure 41D:
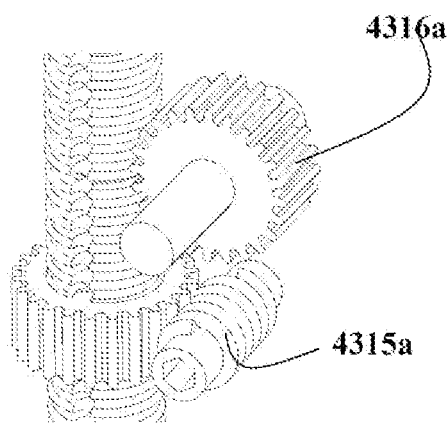
Figure 41E:
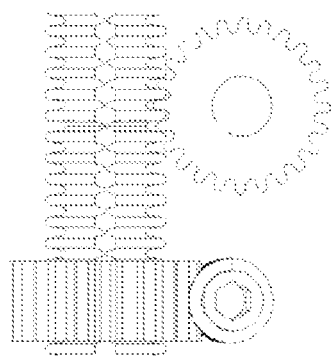

Reference is now made to FIGS. 41A-41E, which present a general illustration of means for effecting motion about DOF 4315 and 4316. The motions relative to the connection means are shown in FIG. 41A, and the means for effecting motion of the medical device are illustrated in FIG. 41B. Means for effecting motion about DOF 4315 comprise worm drive 4315a and worm gear 4315b. As illustrated in FIG. 41C, worm gear 4315b is substantially ring-like in design, with the gear teeth disposed about the outer circumference of the ring. The inner circumference of the ring comprises a protrusion that is adapted to fit into a matching slot in the outer circumference of, and substantially parallel to the longitudinal axis of, rack 4316a. Rack 4316a is adapted to hold medical device 4300. Means for effecting such holding are well known in the art; as a non-limiting example, rack 4316a may comprise a bore along its longitudinal axis, wherein said bore is of the proper diameter (possibly with stopping down) to provide a snug fit to medical device 4300. Rotation of worm drive 4315a about its axis leads to rotation of worm gear 4315b about its longitudinal axis, causing rotation of rack 4316a about its longitudinal axis, and thus causing medical device 4300 within to rotate in proportion to the amount of rotation of the worm drive. Translational motion about DOF 4316 is effected by rack-and-pinion means 4316a and 4316b. When pinion gear 4316b rotates, the rack translates along its longitudinal axis in proportion to the amount of rotation of the pinion gear, causing medical device 4300 to translate with it.

Figure 42:
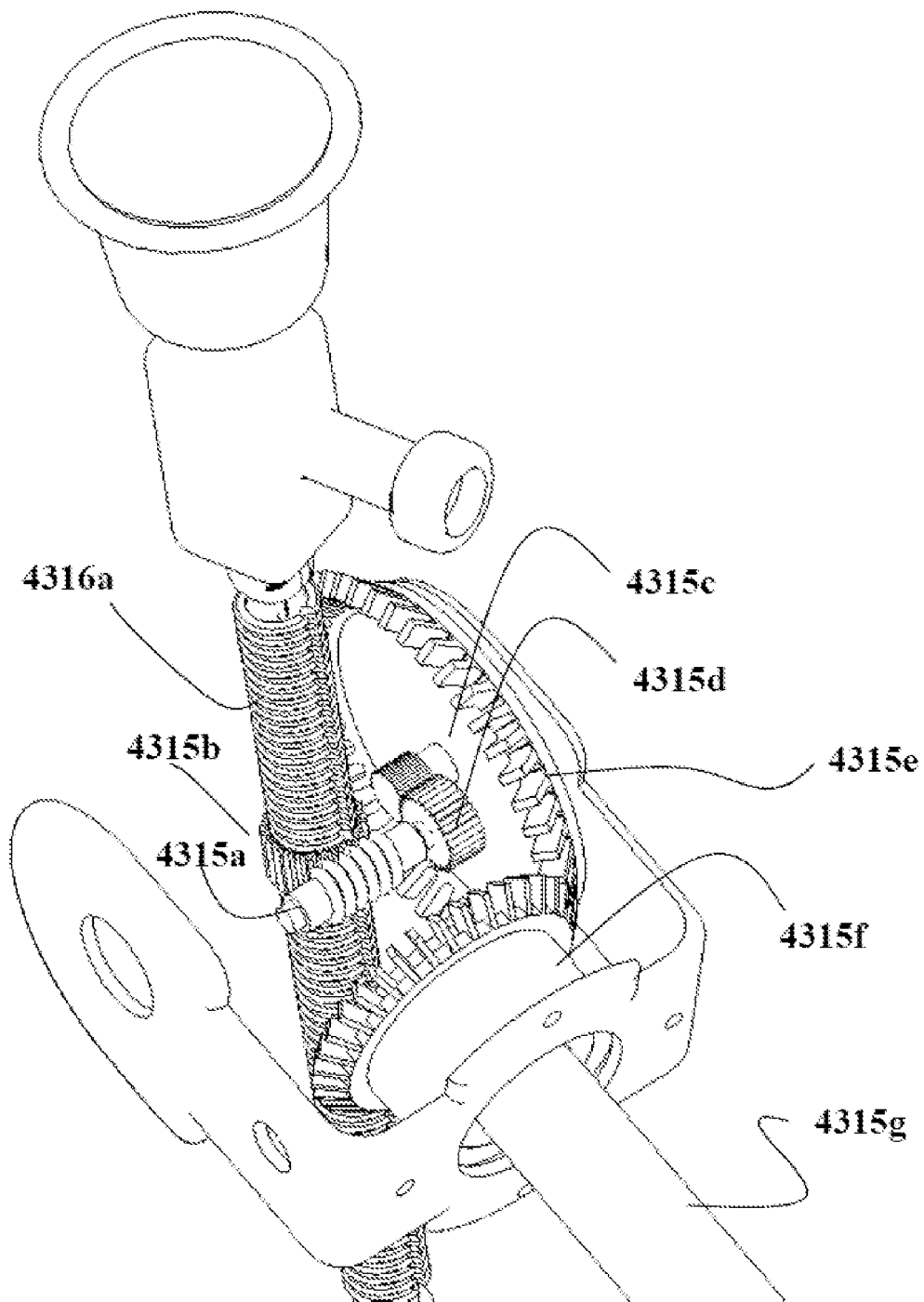
FIG. 42 presents a detailed illustration of means for effecting translational motion about degree of freedom $DOF_5$.

Reference is now made to FIG. 42, which presents a more detailed illustration of means for effecting rotational motion about DOF 4315. Worm gear and drive 4315a and 4315b are mated to rack 4316a as described above. Worm gear 4315a is rigidly connected to spur gear 4315d. Spur gear 4315d is mated to a second spur gear 4315c; in preferred embodiments of the invention, the axes of rotation of gears 4315d and 4315c are substantially parallel. Spur gear 4315c is rigidly connected to, and turns about substantially the same axis as, intermediate gear 4315e. Intermediate gear 4315e is mated to input gear 4315f; as illustrated in the figure, input gear 4315f is disposed such that it may rotate in a plane different from the plane of rotation of intermediate gear 4315e. In preferred embodiments of the invention, the rotation axes of gears 4315e and 4315f are substantially perpendicular. Input gear 4315f is rigidly connected to one end of internal tube 4315g and rotates about an axis substantially coincident with the longitudinal axis of 4315g. The sequence of steps that leads to rotational motion about DOF 4315 is thus as follows: rotation of internal tube 4315g drives rotation of input gear 4315f, which drives simultaneous rotation of intermediate gear 4315e and spur gear 4315c. Rotation of spur gear 4315c drives rotation of spur gear 4315d and hence of worm drive 4315a. Rotation of worm drive 4315a drives rotation of worm gear 4315b, which due to its inability to rotate relative to rack 4316a, causes rotation of rack 4316a and hence of medical device 4300 located within. This rotational motion is thus independent of any other motion of the device or of the connecting means as a whole.

Figure 43A:
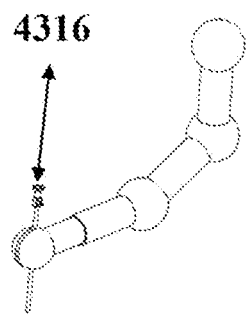
FIGS. 43A-B presents a detailed illustration of means for effecting translational motion about degree of freedom $DOF_6$.
Figure 43B:
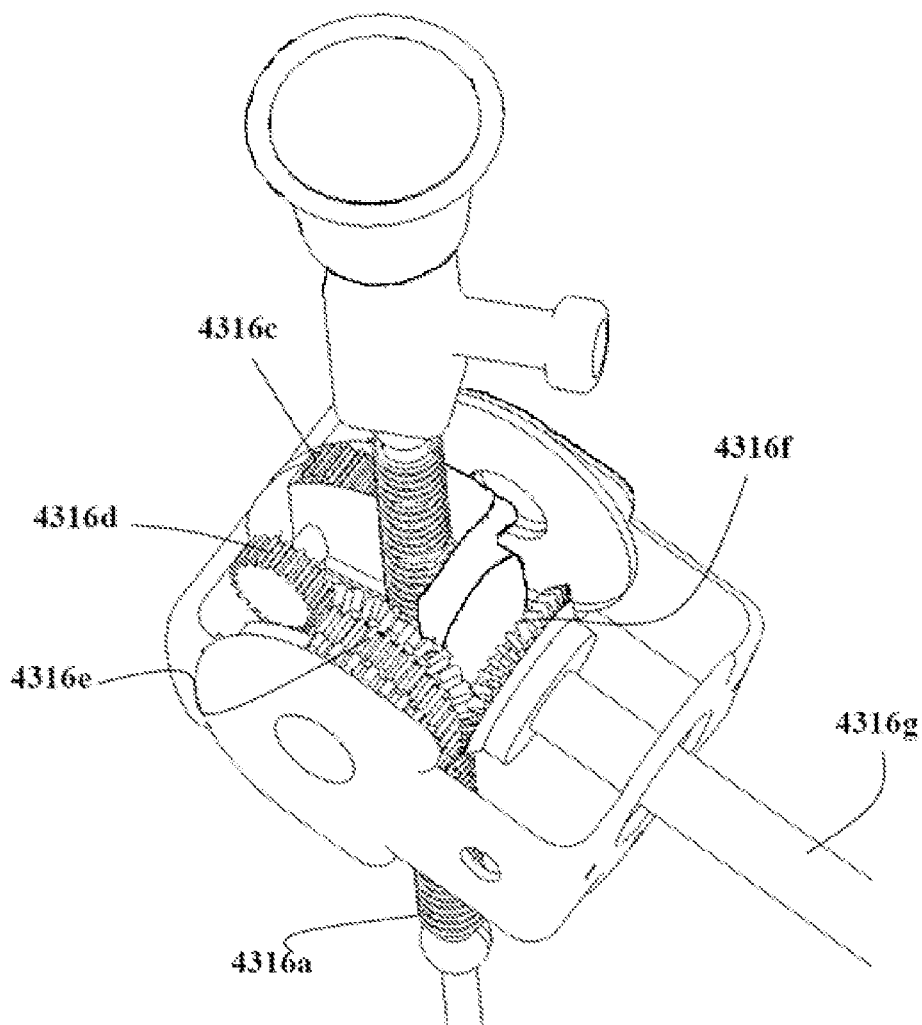

Reference is now made to FIG. 43B, which illustrates in more detail means for effecting translational motion about DOF 4316. Pinion 4315b (the pinion is not visible in this view) is fixed in place relative to the gear assembly, but is free to rotated about its principal axis, and is mated to spur gear 4316c. Spur gear 4316c is connected by a fixed axle to a second spur gear 4316d such that the two gears rotate in tandem. The second spur gear 4316d is mated to intermediate gear 4316e. In preferred embodiments of the invention, the axis of rotation of intermediate gear 4316e is substantially parallel to the axle connecting spur gears 4316c and 4316d. In some embodiments of the invention, intermediate gear 4316e is rigidly connected to, and turns in tandem with, a second intermediate gear with a gear ratio other than 1:1. Intermediate gear 4316e (or the second intermediate gear in those embodiments that comprise it) is mated to input gear 4316f. In preferred embodiments of the invention, the axis of rotation of input gear 4316f is substantially perpendicular to that of intermediate gear 4316e. Input gear 4316f is rigidly connected to internal tube 4316g and rotates about an axis substantially coincident with the longitudinal axis of internal tube 4316g. Thus, translational motion of medical device 4300 is effected as follows: rotation of internal tube 4316g and hence of input gear 4316f drives rotation of intermediate gear 4316e. Rotation of intermediate gear 4316e then drives rotation of spur gear 4316d. Since spur gear 4316c is physically connected to spur gear 4316d, rotation of the latter necessarily causes rotation of the former at the same angular velocity. Rotation of spur gear 4316c then drives rotation of pinion 4316b, which forces translational motion of rack 4316a and hence of the medical device contained within.

The invention claimed is:

1. A two-part robotic device for positioning of a medical instrument, comprising:
   a. a rigidly mountable fixed base unit attachable to a fixed point in space; and
   b. a detachable body unit reversibly coupleable to said fixed base unit, coupleable to said current medical instrument,
   wherein said fixed base unit is adapted to provide independent movement to said medical instrument, said independent movement selected from a group consisting of rotation and translation, and said detachable body unit is removable and replaceable from said fixed base unit such that upon exchange of said medical instrument for a second medical instrument, said second medical instrument is placed in substantially the same location as the location of said medical instrument prior to said exchange, wherein said detachable body unit is an endoscope positioning device comprising means for providing to an endoscope at least 7 degrees of freedom (DOF) selected from a group consisting of at least 6 rotation movements (1007, 1009, 1010, 1011, 1012, 1013, 1601, 1602), at least 1 translation movement (1008) and any combination thereof;

wherein said detachable body unit comprises k consecutive arm sections, where k is a positive integer, and k-1 joints; an sth joint coupling an sth arm section to an (s+1)st arm section, s being between 1 and k-1;

wherein at least one said joint comprises locking means; said locking means are adapted to lock at least one of said k-1 joints in a desired direction; said locking means having at least two states, a locked state and an unlocked state;

wherein at least one joint is adapted to rotate said current medical instrument about two mutually perpendicular axes in the x-y plane; and wherein said detachable body unit is an endoscope positioning device comprising means for providing to said endoscope at least 7 degrees of freedom (DOF) selected from a group consisting of at least 6 rotation movements (1007, 1009, 1010, 1011, 1012, 1013, 1601, 1602), at least 1 translation movement (1008) and any combination thereof; further wherein: each of said k consecutive arm sections comprises n coaxial input shafts adapted to be rotated around an input axis of rotation by m sources of torque, wherein n, m, and k are positive integers, and further wherein said endoscope is coupled to one of said k consecutive arm sections; and a. each of said joints being a constant velocity coupler comprising:
  i. n coaxial input transmission means, each of which is coupled to one of said n input shafts, said input transmission means defining a first plane substantially perpendicular to said input axis of rotation;
  ii. n coaxial second transmission means rotatably connected to said n input transmission means, said second transmission means rotating in a second plane, said second plane substantially perpendicular to said first plane;
  iii. n coaxial output transmission means rotatably connected to said n second transmission means, said output transmission means rotating in a third plane; said third plane being substantially perpendicular to said second plane; and,
  iv. n coaxial output shafts, each of which is coupled to one of said n output transmission means, said n output shafts being adapted to rotate around an output axis of rotation such that (i) turning a given input shaft at a constant velocity will provide a constant velocity at the corresponding output shaft; and (ii) the angle between said input axis of rotation and said output axis of rotation varies in said second plane in an angular range of about 0 to about 360 degrees.

2. The two-part robotic device according to claim 1, wherein said fixed point in space is selected from a group consisting of a floor, a ceiling, or a surgical table.

3. The two-part robotic device according to claim 1, wherein, in said locked state, either said sth joint and said (s+1)st arm section rotate as a unit about a main longitudinal axis of said sth arm section or said sth joint and said sth arm section is rotateable as a unit about a main longitudinal axis of said (s+1)st arm section; and, in said unlocked state, the angle between said sth arm section (s+1)st arm section is changeable.

4. The two-part robotic device according to claim 1, wherein at least one joint is adapted to rotate said current medical instrument about two mutually perpendicular axes in the x-y plane.

5. The two-part robotic device according to claim 1 wherein said input transmission means, second transmission means, and said output transmission means are selected from a group consisting of gearwheels, wheels, crown gears, bevel gears, spur gears, belts, and any combination thereof.

6. The two-part robotic device according to claim 1 additionally comprising:
  a. an axial support member (601) adapted to provide axial support to said n output shafts in said third plane; and
  b. a circular track (618) centered on the axis of rotation of said second transmission means, said axial support member being adapted to fit into said track and slide within it.

7. The two-part robotic device according to claim 1, wherein said fixed base unit comprises h consecutive arm sections and h-1 joints, h being a positive integer, such that different arm sections of said fixed base unit are removable and replaceable.

8. A two-part robotic device for positioning of a medical instrument, comprising:
  a. a rigidly mountable fixed base unit attachable to a fixed point in space; and
  b. a detachable body unit reversibly coupleable to said fixed base unit, coupleable to said current medical instrument,
  wherein said fixed base unit is adapted to provide independent movement to said medical instrument, said independent movement selected from a group consisting of rotation and translation, and said detachable body unit is removable and replaceable from said fixed base unit such that upon exchange of said medical instrument for a second medical instrument, said second medical instrument is placed in substantially the same location as the location of said medical instrument prior to said exchange,
  wherein said detachable body unit is an endoscope positioning device comprising means for providing to an endoscope at least 7 degrees of freedom (DOF) selected from a group consisting of at least 6 rotation movements (1007, 1009, 1010, 1011, 1012, 1013, 1601, 1602), at least 1 translation movement (1008) and any combination thereof;
  wherein said detachable body unit comprises k consecutive arm sections, where k is a positive integer, and k-1 joints; an sth joint coupling an sth arm section to an (s+1)st arm section, s being between 1 and k-1;
  wherein at least one said joint comprises locking means; said locking means are adapted to lock at least one of said k-1 joints in a desired direction; said locking means having at least two states, a locked state and an unlocked state;

wherein at least one joint is adapted to rotate said current medical instrument about two mutually perpendicular axes in the x-y plane;

wherein said fixed base unit comprises h consecutive arm sections and h-1 joints, h being a positive integer, such that different arm sections of said fixed base unit are removable and replaceable; and wherein:
a. each of said h consecutive arm sections of said fixed base unit comprises q coaxial input shafts adapted to be rotated around an input axis of rotation by p sources of torque, where q, p, and h are positive integers, wherein either said current instrument or said detachable body unit is coupleable to one of said h consecutive arm sections;
b. said fixed base unit further comprises at least h-1 constant velocity couplers coupling each pair of said h consecutive arm sections together, each of said constant velocity couplers comprising:
  i. q coaxial input transmission means, each of which is coupled to one of said q input shafts, wherein said input transmission means define a first plane substantially perpendicular to said input axis of rotation;
  ii. q coaxial second transmission means rotatably connected to said q input transmission means, said second transmission means rotating in a second plane substantially perpendicular to said first plane;
  iii. q coaxial output transmission means rotatably connected to said q second transmission means, said output transmission means rotating in a third plane substantially perpendicular to said second plane;
a. q coaxial output shafts, each of which is coupled to one of said q output transmission means, said q output shafts adapted to rotate around an output axis of rotation; such that (i) turning a given input shaft at a constant velocity will provide a constant velocity at the corresponding output shaft and (ii) the angle between said input axis of rotation and said output axis of rotation varies in said second plane in an angular range of about 0 to about 360 degrees.

9. The two-part robotic device according to claim 8, wherein said input transmission means, second transmission means, and said output transmission means are selected from a group consisting of gearwheels, wheels, crown gears, bevel gears, spur gears, belts, and any combination thereof.

10. The two-part robotic device according to claim 8, additionally comprising:
a. an axial support member (601) adapted to provide axial support to said q output shafts in said third plane; and,
b. a circular track (618) centered on the axis of rotation of said second transmission means, said axial support member being adapted to fit into said track and slide within it.

11. The two-part robotic device according to claim 8, additionally comprising a radial support member (604) adapted to provide radial support to said q output shafts, said radial support member being adapted to rotate in said second plane.

12. The two-part robotic device according to claim 8, wherein the gear ratio between said input and output shafts is between about 10 and about 0.1.

13. The two-part robotic device according to claim 8, additionally comprising q coaxial auxiliary shafts in rotating communication with said q second transmission means, said q coaxial auxiliary shafts rotating in said second plane, and said q coaxial auxiliary shafts capable of either being driven by said input shafts or driving said input shafts.

14. The two-part robotic device according to claim 8, wherein said locking means is adapted for preventing relative movement between one or more of said input axis shafts and said constant velocity joint, wherein said constant velocity joint is caused to rotate as a body with said locked input axis shafts.

15. The two-part robotic device according to claim 8, wherein said locking means is adapted for preventing relative movement between one or more of said output axis shafts and said constant velocity joint, wherein said constant velocity joint is caused to rotate as a body with said locked output axis shafts.

16. A two-part robotic device for positioning of a medical instrument, comprising:
a. a rigidly mountable fixed base unit attachable to a fixed point in space; and
b. a detachable body unit reversibly coupleable to said fixed base unit, coupleable to said current medical instrument, wherein said fixed base unit is adapted to provide independent movement to said medical instrument, said independent movement selected from a group consisting of rotation and translation, and said detachable body unit is removable and replaceable from said fixed base unit such that upon exchange of said medical instrument for a second medical instrument, said second medical instrument is placed in substantially the same location as the location of said medical instrument prior to said exchange, wherein said detachable body unit is an endoscope positioning device comprising means for providing to an endoscope at least 7 degrees of freedom (DOF) selected from a group consisting of at least 6 rotation movements (1007, 1009, 1010, 1011, 1012, 1013, 1601, 1602), at least 1 translation movement (1008) and any combination thereof;

wherein said detachable body unit comprises k consecutive arm sections, where k is a positive integer, and k-1 joints; an sth joint coupling an sth arm section to an (s+1)st arm section, s being between 1 and k-1, wherein at least one said joint comprises locking means; said locking means are adapted to lock at least one of said k-1 joints in a desired direction; said locking means having at least two states, a locked state and an unlocked state;

wherein, in said locked state, either said sth joint and said (s+1)st arm section rotate as a unit about a main longitudinal axis of said sth arm section or said sth joint and said sth arm section is rotateable as a unit about a main longitudinal axis of said (s+1)st arm section; and, in said unlocked state, the angle between said sth arm section (s+1)st arm section is changeable; and wherein said detachable body unit is an endoscope positioning device comprising means for providing to said endoscope at least 7 degrees of freedom (DOF) selected from a group consisting of at least 6 rotation movements (1007, 1009, 1010, 1011, 1012, 1013, 1601, 1602), at least 1 translation movement (1008) and any combination thereof; further wherein: each of said k consecutive arm sections comprises n coaxial input shafts adapted to be rotated around an input axis of rotation by m sources of torque, wherein n, m, and k are positive integers, and further wherein said endoscope is coupled to one of said k consecutive arm sections; and
a. each of said joints being a constant velocity coupler comprising:

i. n coaxial input transmission means, each of which is coupled to one of said n input shafts, said input transmission means defining a first plane substantially perpendicular to said input axis of rotation;
ii. n coaxial second transmission means rotatably connected to said n input transmission means, said second transmission means rotating in a second plane, said second plane substantially perpendicular to said first plane;
iii. n coaxial output transmission means rotatably connected to said n second transmission means, said output transmission means rotating in a third plane; said third plane being substantially perpendicular to said second plane; and,
iv. n coaxial output shafts, each of which is coupled to one of said n output transmission means, said n output shafts being adapted to rotate around an output axis of rotation such that (i) turning a given input shaft at a constant velocity will provide a constant velocity at the corresponding output shaft; and (ii) the angle between said input axis of rotation and said output axis of rotation varies in said second plane in an angular range of about 0 to about 360 degrees.

17. The two-part robotic device according to claim 16, wherein said fixed point in space is selected from a group consisting of a floor, a ceiling, or a surgical table.

18. The two-part robotic device according to claim 16, wherein at least one joint is adapted to rotate said current medical instrument about two mutually perpendicular axes in the x-y plane.

* * * * *